United States Patent
Musuku et al.

(10) Patent No.: US 10,596,339 B2
(45) Date of Patent: Mar. 24, 2020

(54) INTUBATION DEVICES AND METHODS OF USE

(71) Applicants: Sridhar R. Musuku, Watervliet, NY (US); Divya Cherukupalli, Watervliet, NY (US)

(72) Inventors: Sridhar R. Musuku, Watervliet, NY (US); Divya Cherukupalli, Watervliet, NY (US)

( * ) Notice: Subject to any disclaimer, the term of this patent is extended or adjusted under 35 U.S.C. 154(b) by 0 days.

(21) Appl. No.: 16/255,983

(22) Filed: Jan. 24, 2019

(65) Prior Publication Data

US 2019/0351167 A1    Nov. 21, 2019

Related U.S. Application Data

(60) Provisional application No. 62/674,255, filed on May 21, 2018, provisional application No. 62/769,467, filed on Nov. 19, 2018.

(51) Int. Cl.
*A61M 16/04*    (2006.01)

(52) U.S. Cl.
CPC ...... *A61M 16/0497* (2013.01); *A61M 16/049* (2014.02); *A61M 16/0434* (2013.01); *A61M 16/0409* (2014.02)

(58) Field of Classification Search
CPC .............. A61M 16/04; A61M 16/0402; A61M 16/0409; A61M 16/0411; A61M 16/0415;
(Continued)

(56) References Cited

U.S. PATENT DOCUMENTS

| 3,913,568 A | 10/1975 | Carpenter |
| 4,742,819 A | 5/1988 | George |

(Continued)

FOREIGN PATENT DOCUMENTS

| CN | 203235108 U | 10/2013 |
| CN | 103463719 A | 12/2013 |

(Continued)

OTHER PUBLICATIONS

English translation of WO2014127548 accessed on Aug. 9, 2019 (Year: 2019).*

(Continued)

*Primary Examiner* — Kendra D Carter
*Assistant Examiner* — Elliot S Ruddie
(74) *Attorney, Agent, or Firm* — Tech Valley Patent, LLC; John Pietrangelo

(57) ABSTRACT

Intubation devices and methods of intubating a patient are provided. The intubation devices include a laryngeal mask airway (LMA) component having a mask portion and a tube portion and an endotracheal tube (ETT) component positioned in the laryngeal mask airway (LMA) component having a translatable and/or rotatable endotracheal tube. The endotracheal tube can be translated and/or rotated by a manipulation rod extending through the laryngeal mask airway (LMA) component and mounted to the endotracheal tube (ETT). The intubation devices may include inflatable cuffs adapted to manipulate the positioning or orientation of the endotracheal tube and/or to seal openings about the endotracheal tubes. Various ports, passages, and conduits are provided to enhance the use and manipulation of the intubation device.

35 Claims, 28 Drawing Sheets

(58) Field of Classification Search
CPC .......... A61M 16/0418; A61M 16/0427; A61M 16/0429; A61M 16/0434; A61M 16/0465; A61M 16/0486; A61M 16/0497
USPC .................................................. 128/200.23
See application file for complete search history.

(56) References Cited

U.S. PATENT DOCUMENTS

| | | | | |
|---|---|---|---|---|
| 5,038,766 | A * | 8/1991 | Parker | A61M 16/0488 128/200.26 |
| 5,303,697 | A * | 4/1994 | Brain | A61M 16/04 128/200.26 |
| 5,337,735 | A | 8/1994 | Salerno | |
| 5,584,290 | A | 12/1996 | Brain | |
| 5,623,921 | A | 4/1997 | Kinsinger et al. | |
| 5,682,880 | A | 11/1997 | Brain | |
| 5,896,858 | A | 4/1999 | Brain | |
| D410,286 | S | 5/1999 | Tamirisa | |
| 6,079,409 | A | 6/2000 | Brain | |
| 6,792,948 | B2 | 9/2004 | Brain | |
| D497,428 | S | 10/2004 | Hayamizu | |
| 7,040,322 | B2 | 5/2006 | Fortuna | |
| D530,818 | S | 10/2006 | Lin | |
| D580,549 | S | 11/2008 | Schwartz | |
| D603,958 | S | 11/2009 | Schwartz | |
| D603,959 | S | 11/2009 | Schwartz | |
| D611,138 | S | 3/2010 | Nasir | |
| D615,188 | S | 5/2010 | Nasir | |
| 7,762,261 | B1 | 7/2010 | Fortuna | |
| 8,215,307 | B2 | 7/2012 | Nasir | |
| D695,401 | S | 12/2013 | Huels | |
| 10,182,712 | B2 | 1/2019 | Mathes | |
| 2001/0050082 | A1 | 12/2001 | Christopher | |
| 2004/0079364 | A1 | 4/2004 | Christopher | |
| 2005/0081861 | A1 * | 4/2005 | Nasir | A61M 16/04 128/207.14 |
| 2005/0268917 | A1 | 12/2005 | Boedeker et al. | |
| 2006/0180155 | A1 | 8/2006 | Glassenberg et al. | |
| 2008/0060655 | A1 | 3/2008 | Brain | |
| 2008/0308098 | A1 | 12/2008 | Schwartz | |
| 2009/0090356 | A1 | 4/2009 | Cook | |
| 2013/0220332 | A1 * | 8/2013 | Baska | A61M 16/04 128/207.15 |
| 2013/0269689 | A1 | 10/2013 | Brain | |
| 2013/0324798 | A1 | 12/2013 | Molnar et al. | |
| 2014/0041673 | A1 | 2/2014 | Walters | |
| 2015/0128946 | A1 | 5/2015 | Stix | |
| 2015/0268917 | A1 | 9/2015 | Leppanen et al. | |
| 2015/0283346 | A1 | 10/2015 | Breslauer et al. | |
| 2017/0216544 | A1 * | 8/2017 | Baska | A61M 16/0488 |
| 2017/0232216 | A1 | 8/2017 | Nave et al. | |

FOREIGN PATENT DOCUMENTS

| | | | |
|---|---|---|---|
| CN | 203620024 U | 6/2014 | |
| CN | 10400125 A * | 8/2014 | A61M 16/04 |
| CN | 203861713 U | 10/2014 | |
| CN | 104800941 A | 7/2015 | |
| CN | 204468927 U | 7/2015 | |
| CN | 204972582 U | 1/2016 | |
| WO | 2014127548 A1 | 8/2014 | |
| WO | WO-2014127548 A1 * | 8/2014 | A61M 16/04 |
| WO | 2015113338 A1 | 8/2015 | |

OTHER PUBLICATIONS

LMA Supreme Airway, Chinook Medical Gear Inc, Product No. #01621PA, [https://www.chinookmed.com/01621pa/lma-supreme-airway.html], accessed Jan. 21, 2019.
Invitation to Pay Fees and Partial Search Report issued for corresponding PCT application PCT/US2019/029702, 12 pages, dated Jul. 22, 2019.
Office Action for related design U.S. Appl. No. 29/681,831, dated Apr. 18, 2019, 13 pages.
Written Opinion issued by European Patent Office for corresponding PCT application PCT/US2019/029702, 10 pages, dated Sep. 30, 2019.
International Search Report issued by European Patent Office for corresponding PCT application PCT/US2019/029702, 7 pages dated Sep. 30, 2019.

* cited by examiner

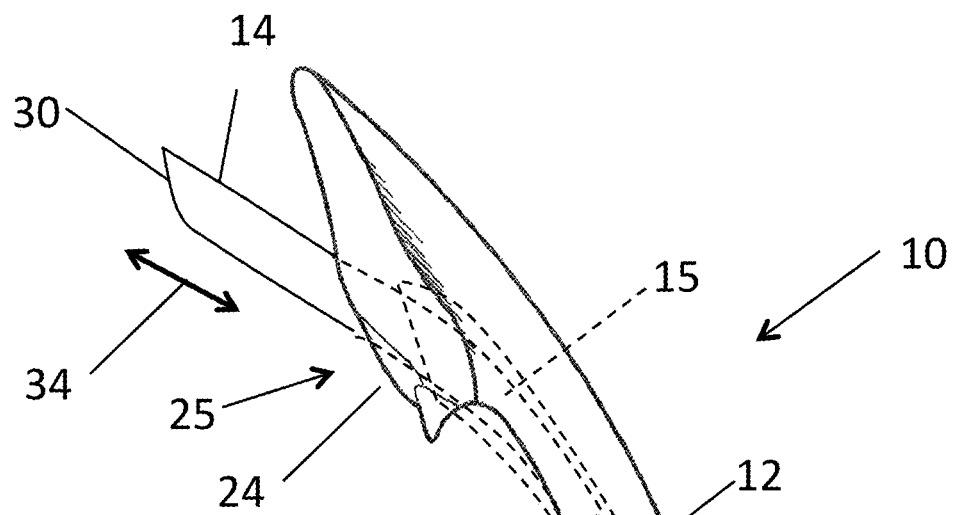
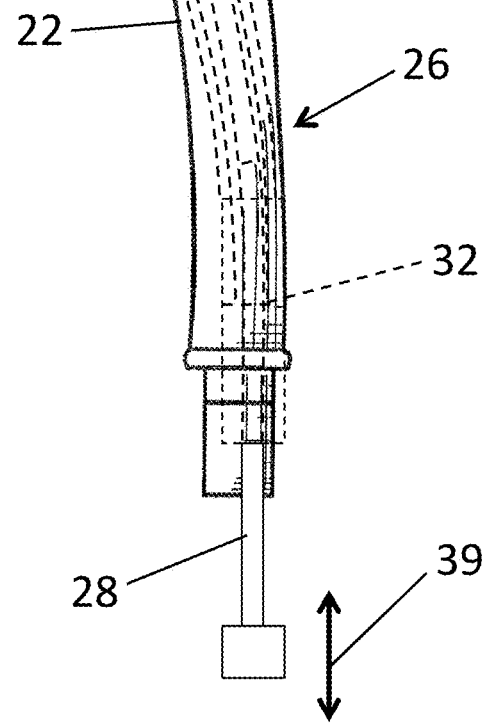
Figure 2

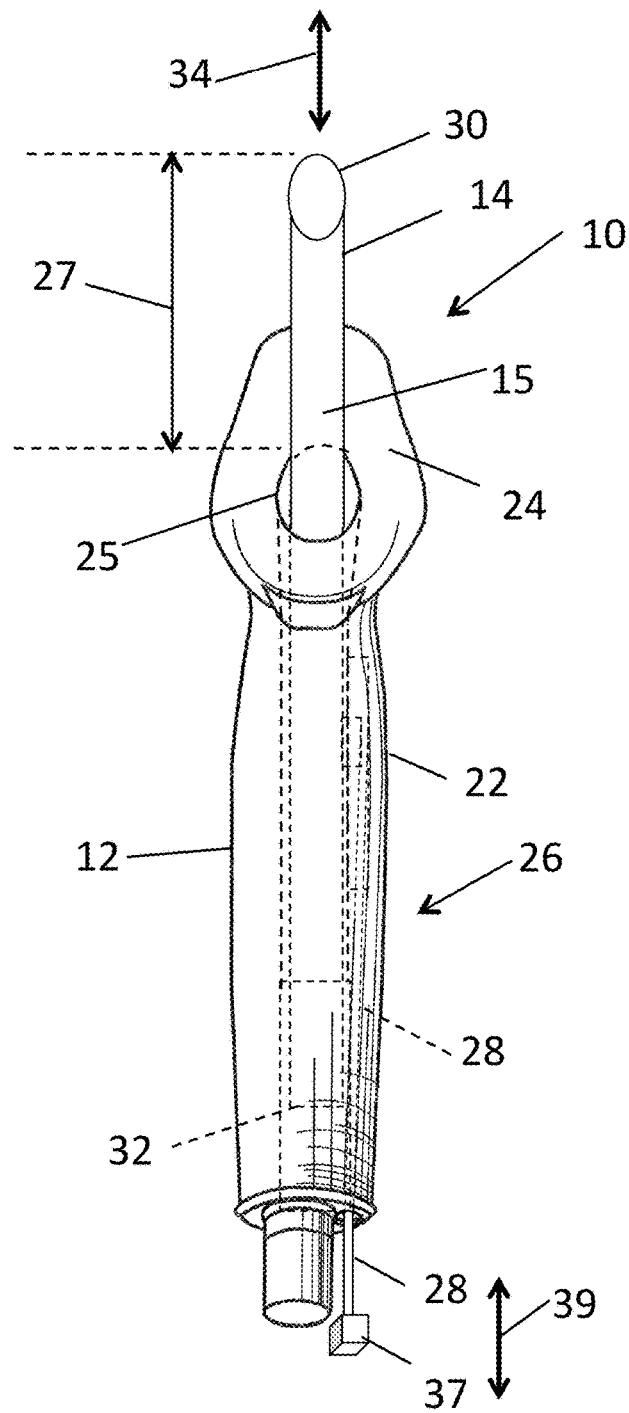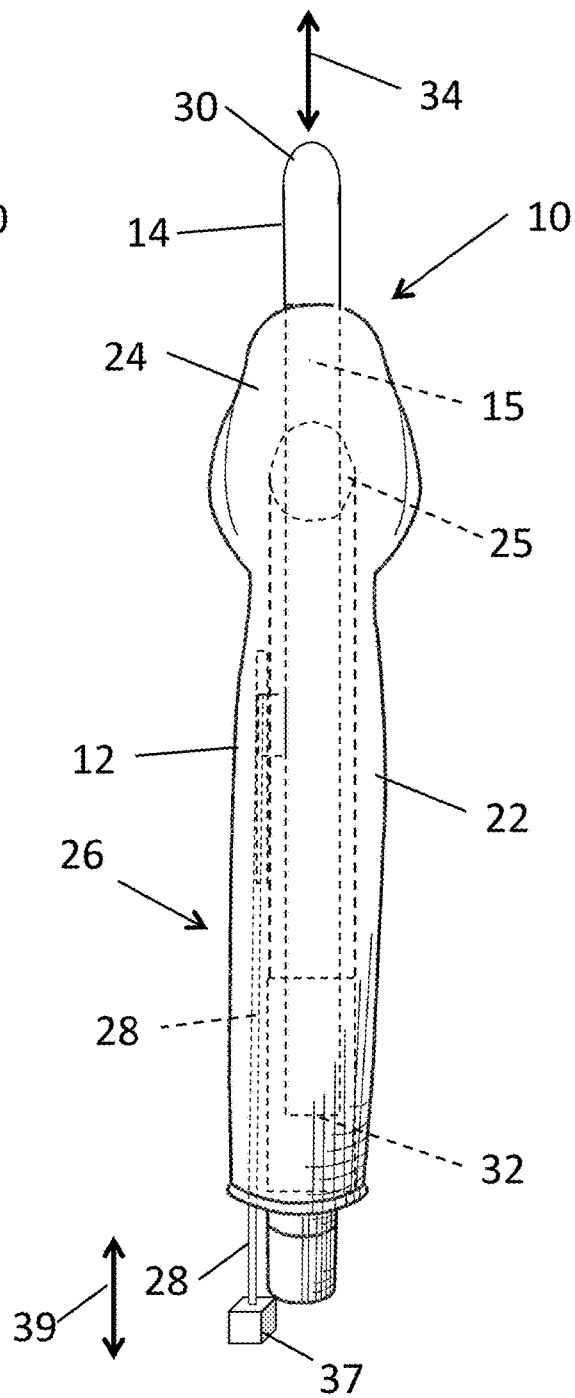
Figure 3
Figure 4

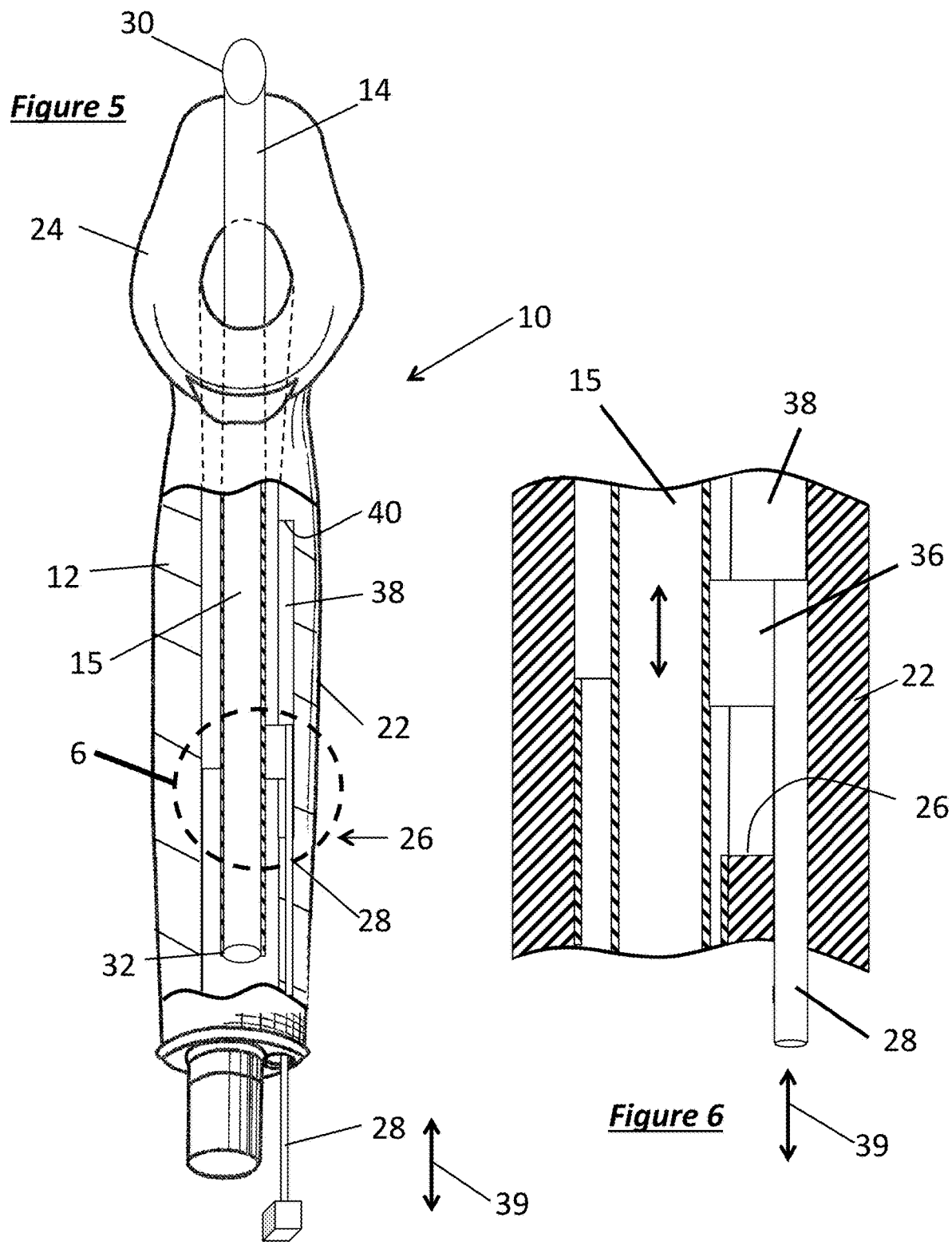

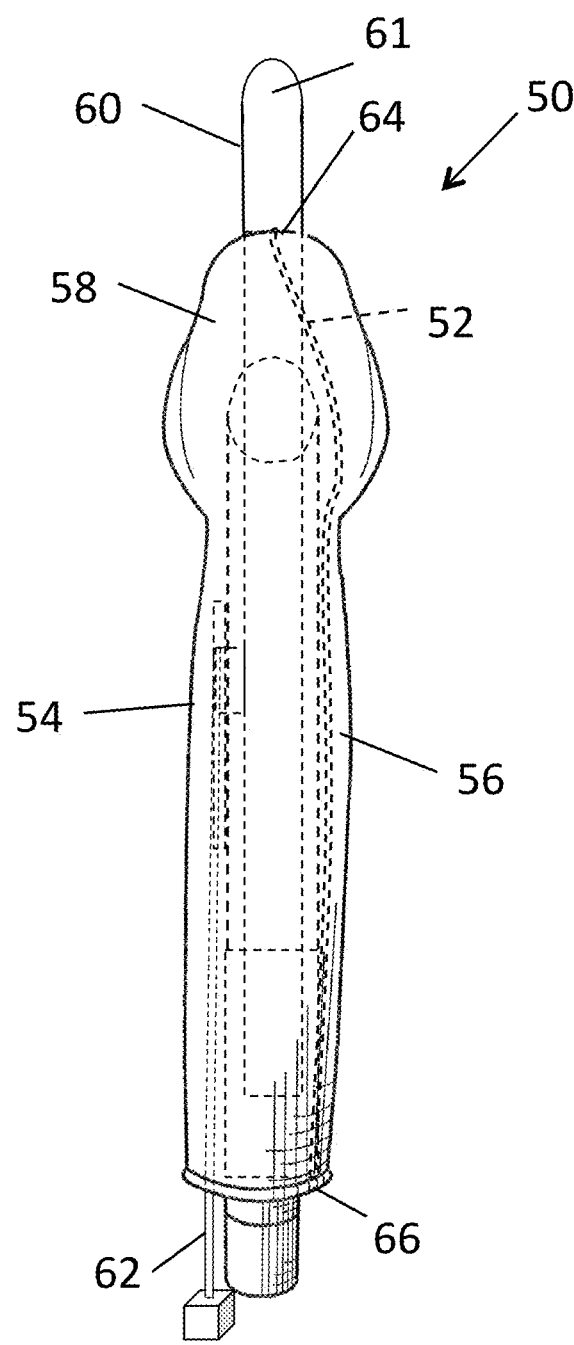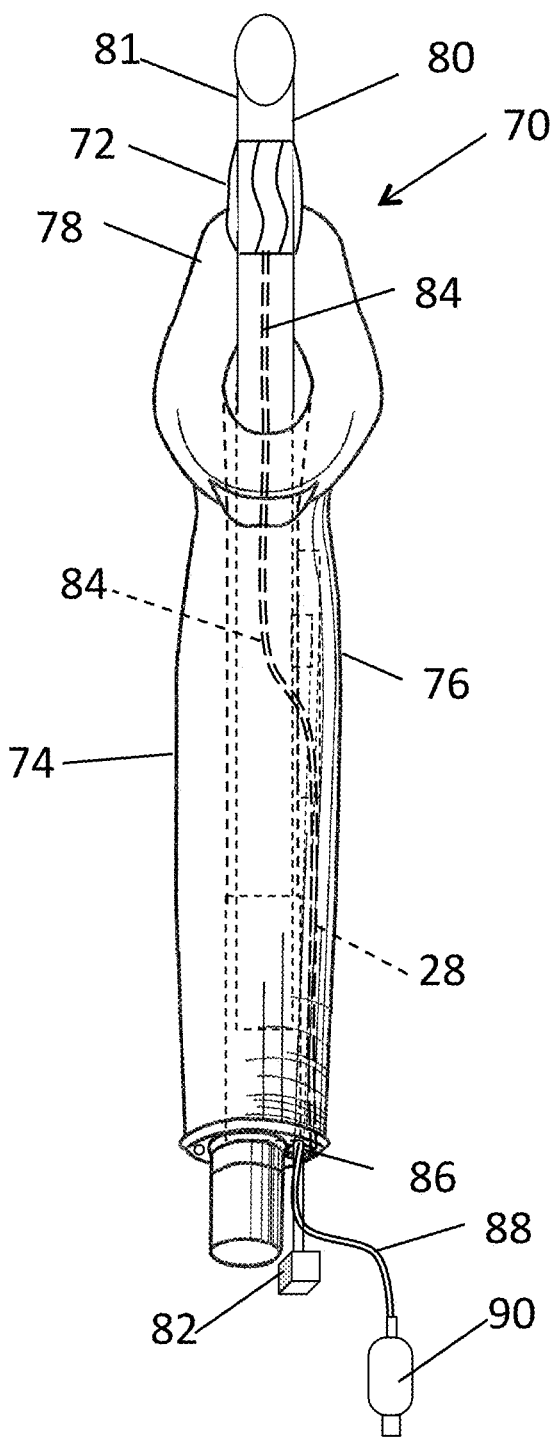
*Figure 7*
*Figure 8*

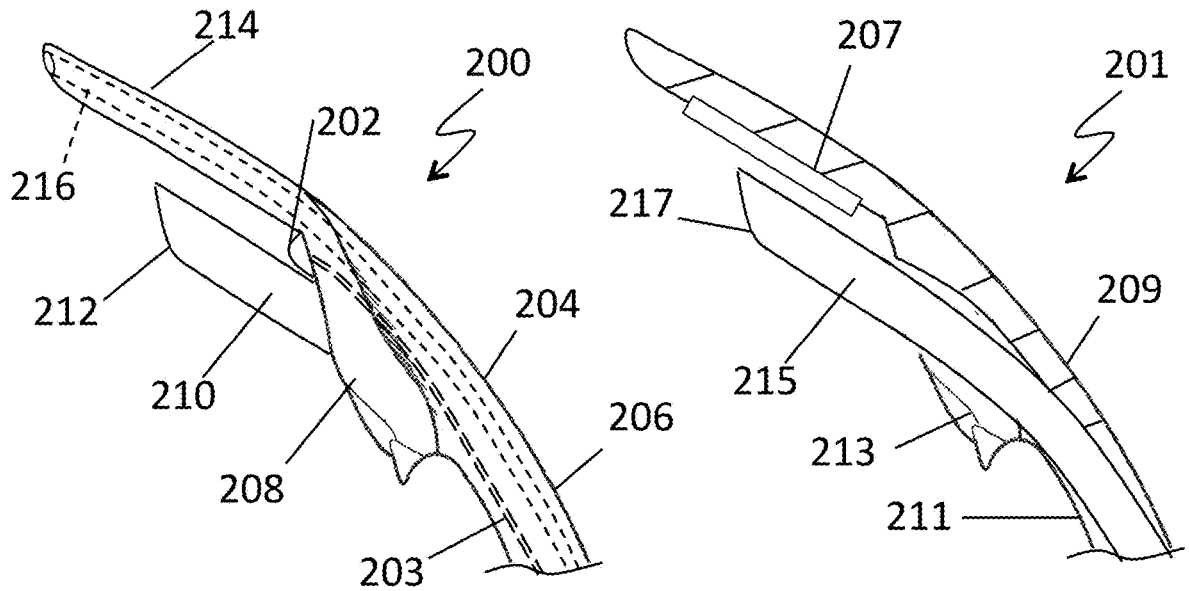
*Figure 16*  *Figure 16A*
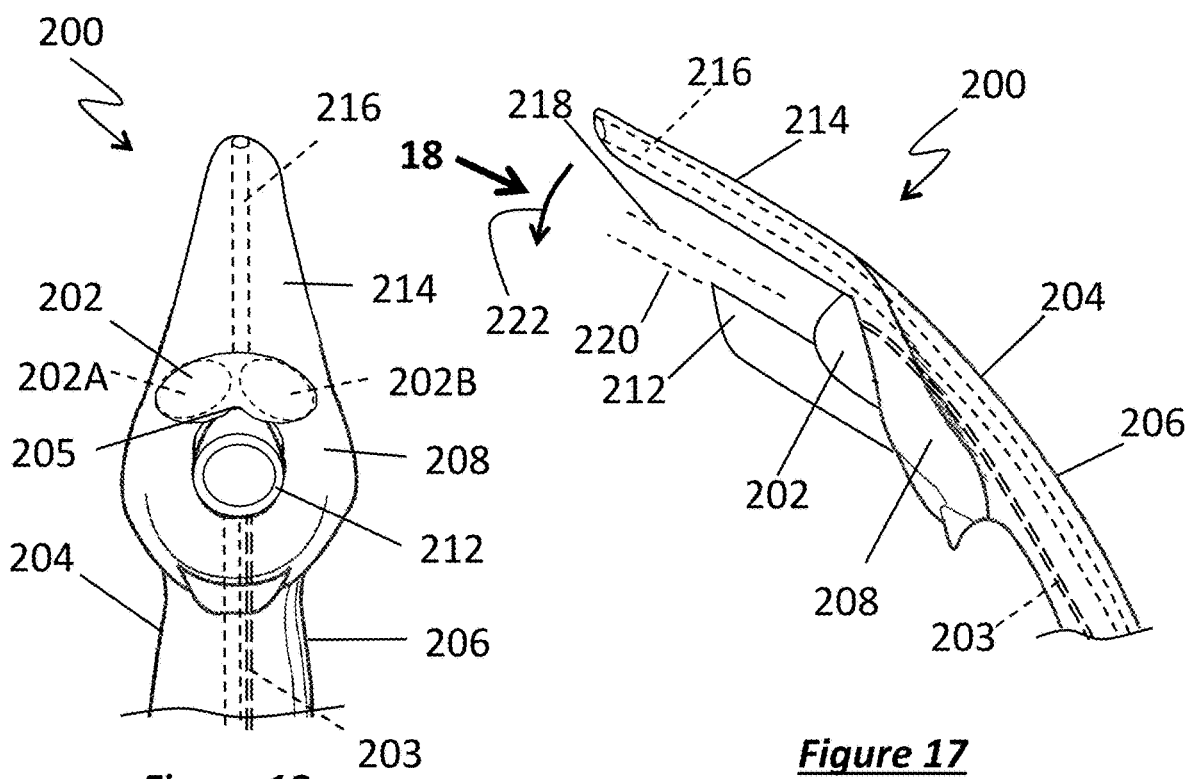
*Figure 18*  *Figure 17*

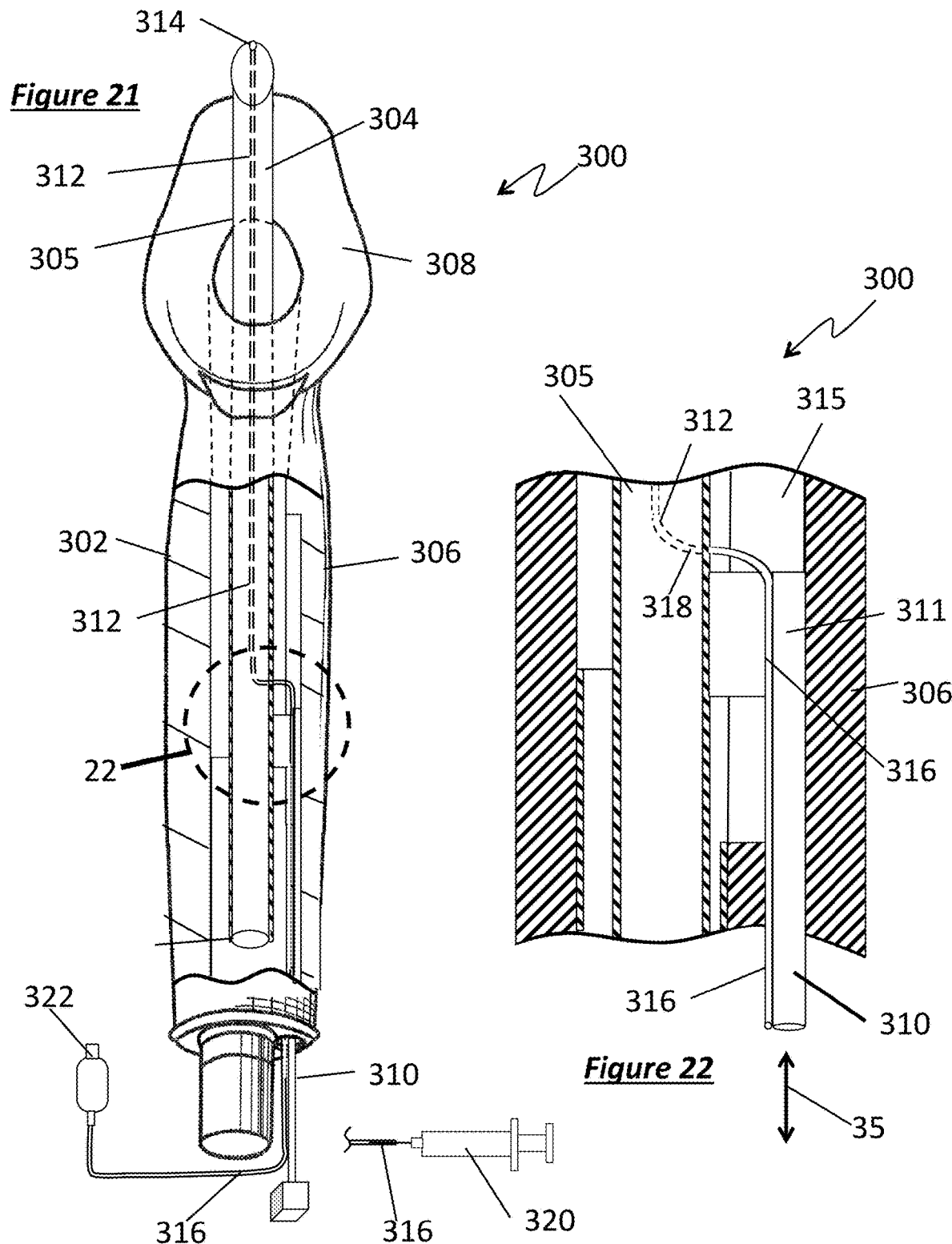

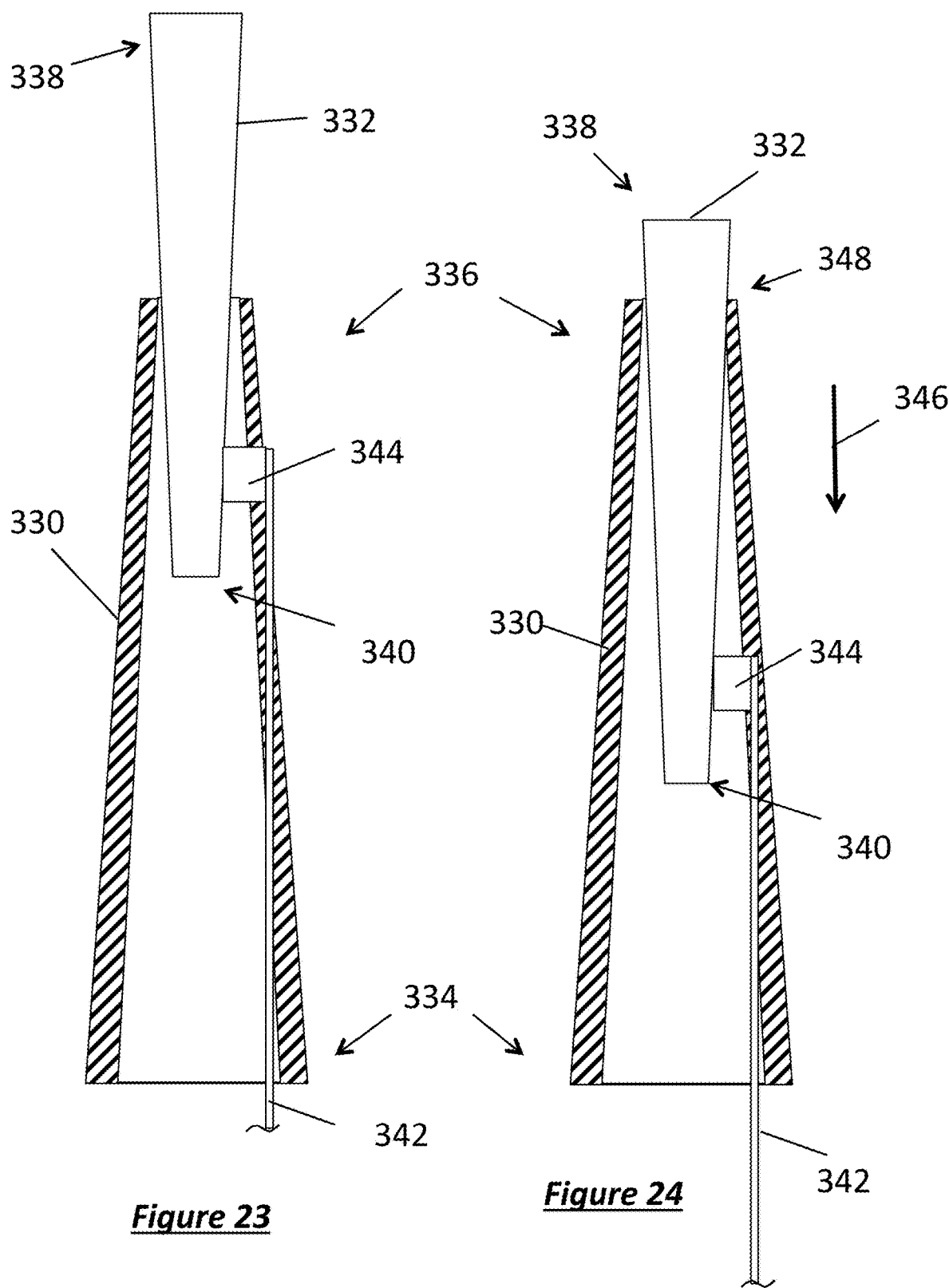
*Figure 23*     *Figure 24*

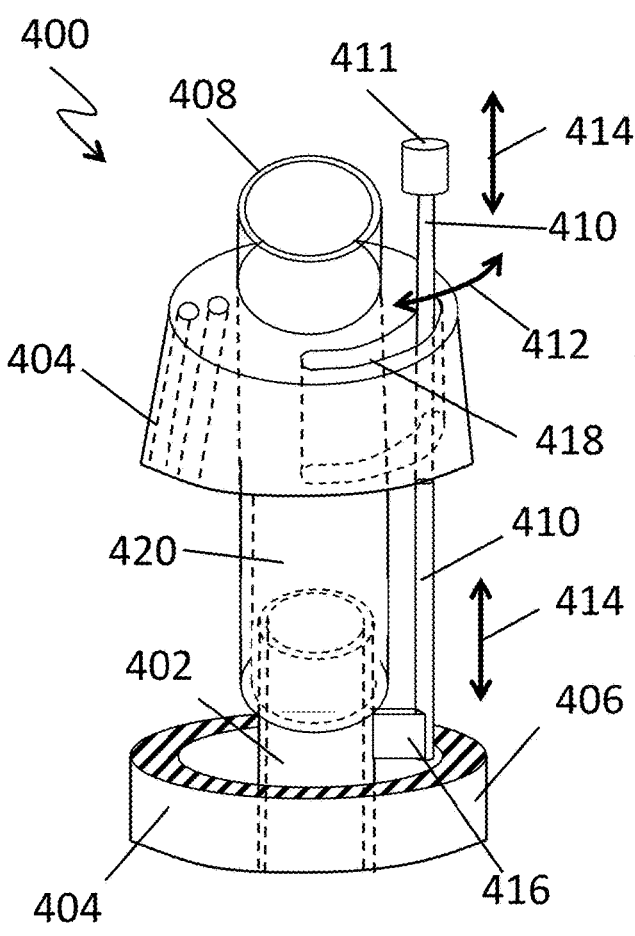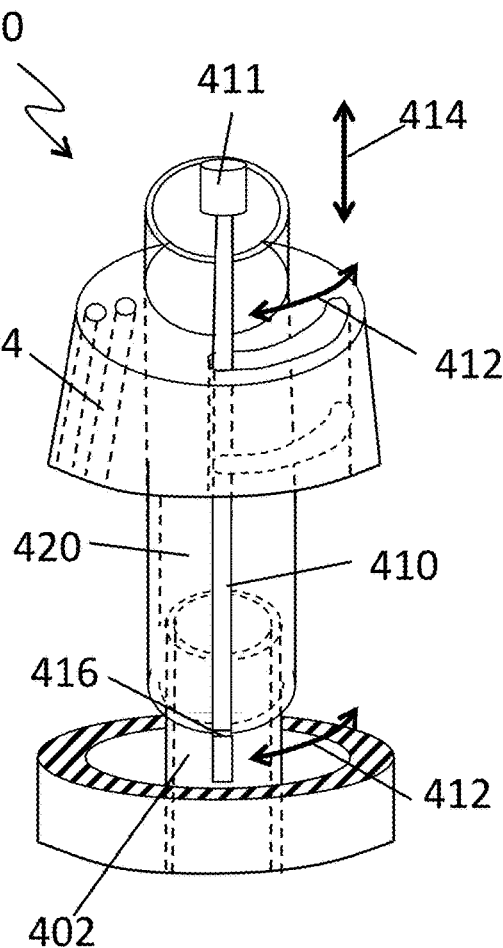
*Figure 25*
*Figure 26*

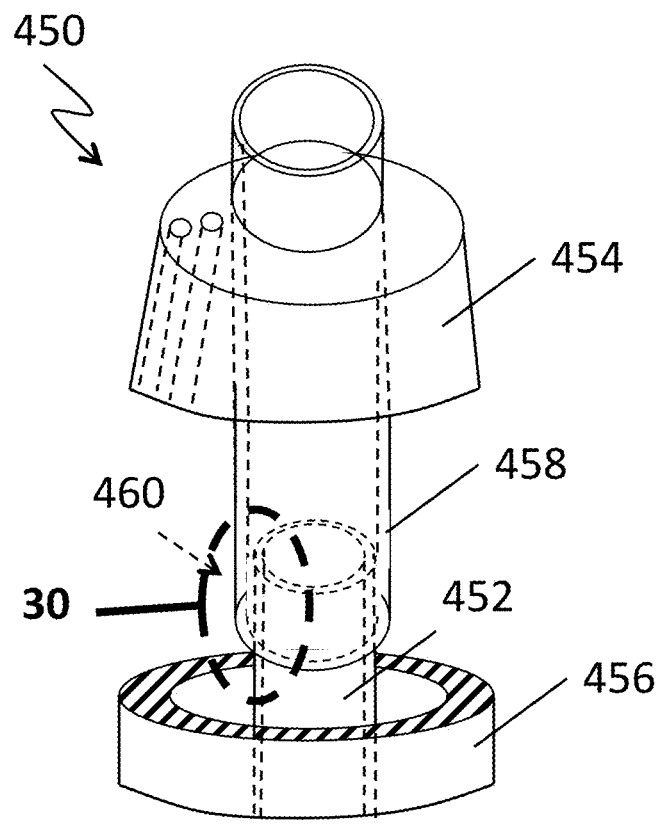
*Figure 29*
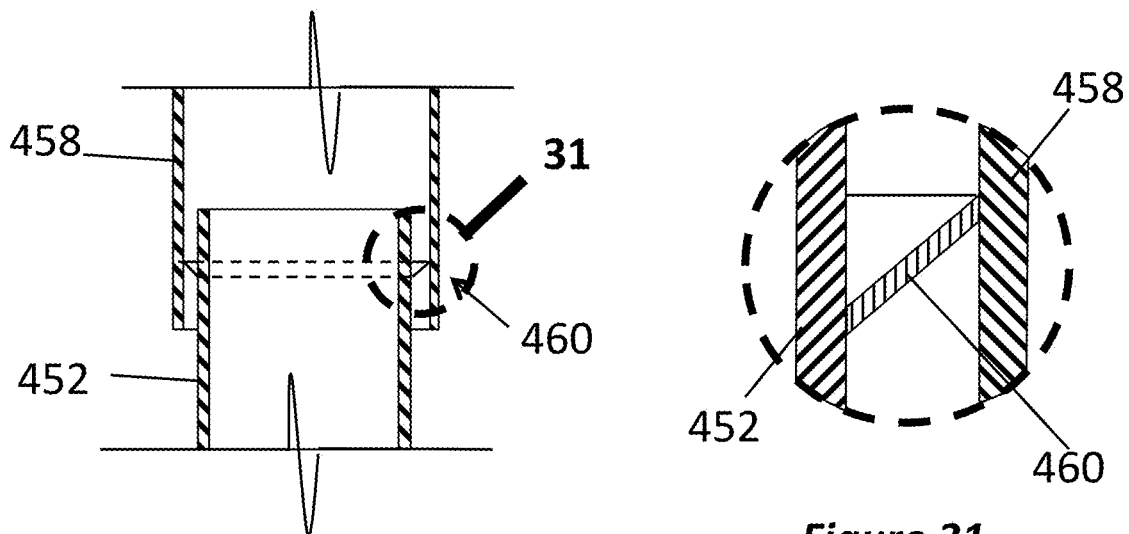
*Figure 30*
*Figure 31*

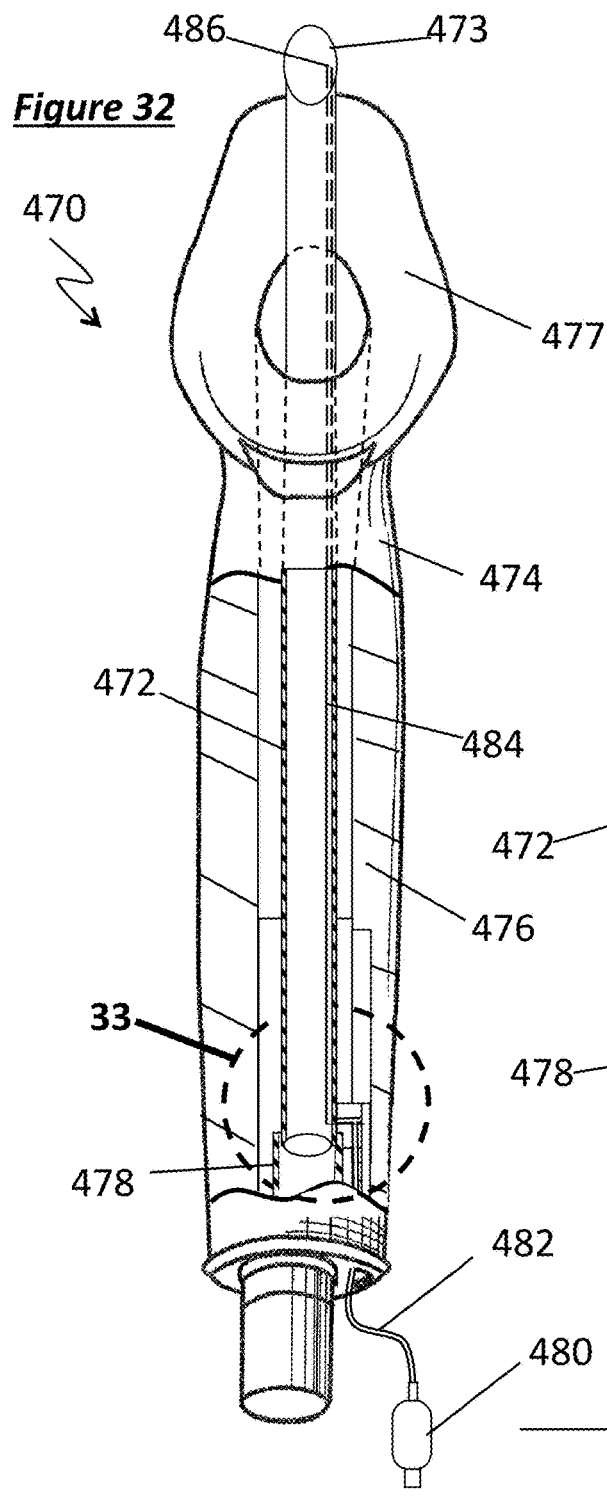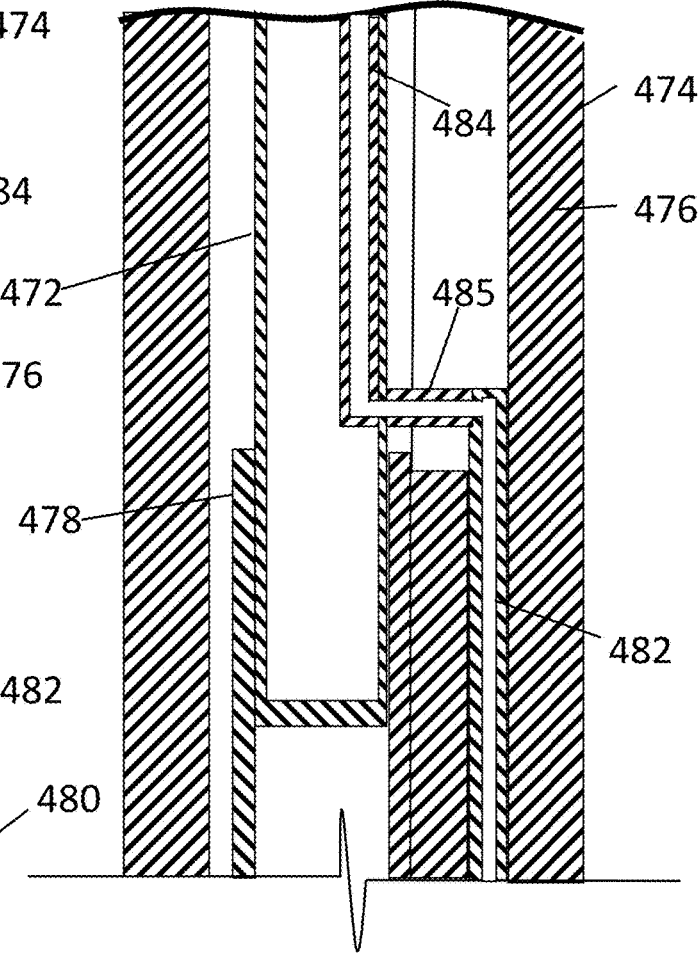

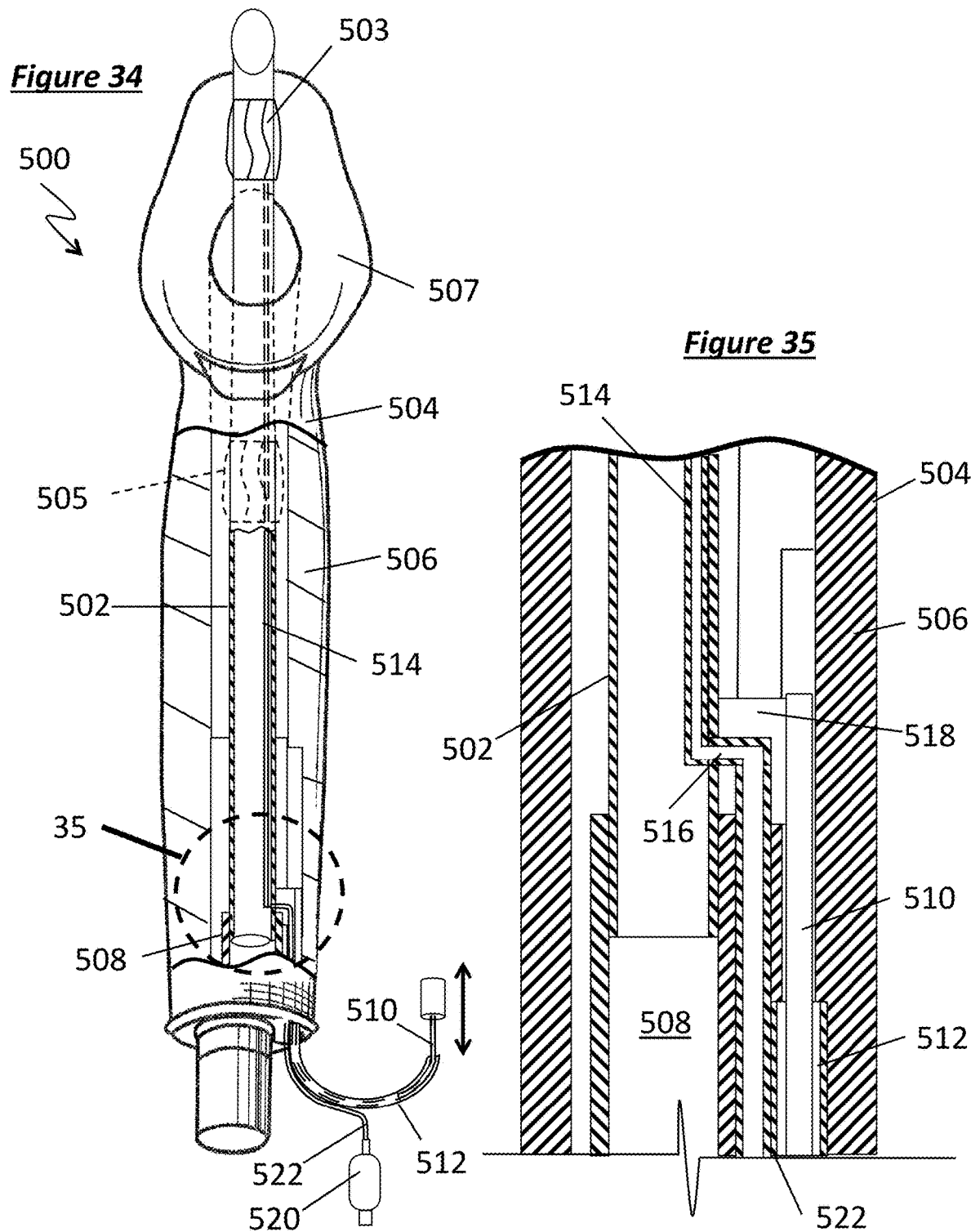

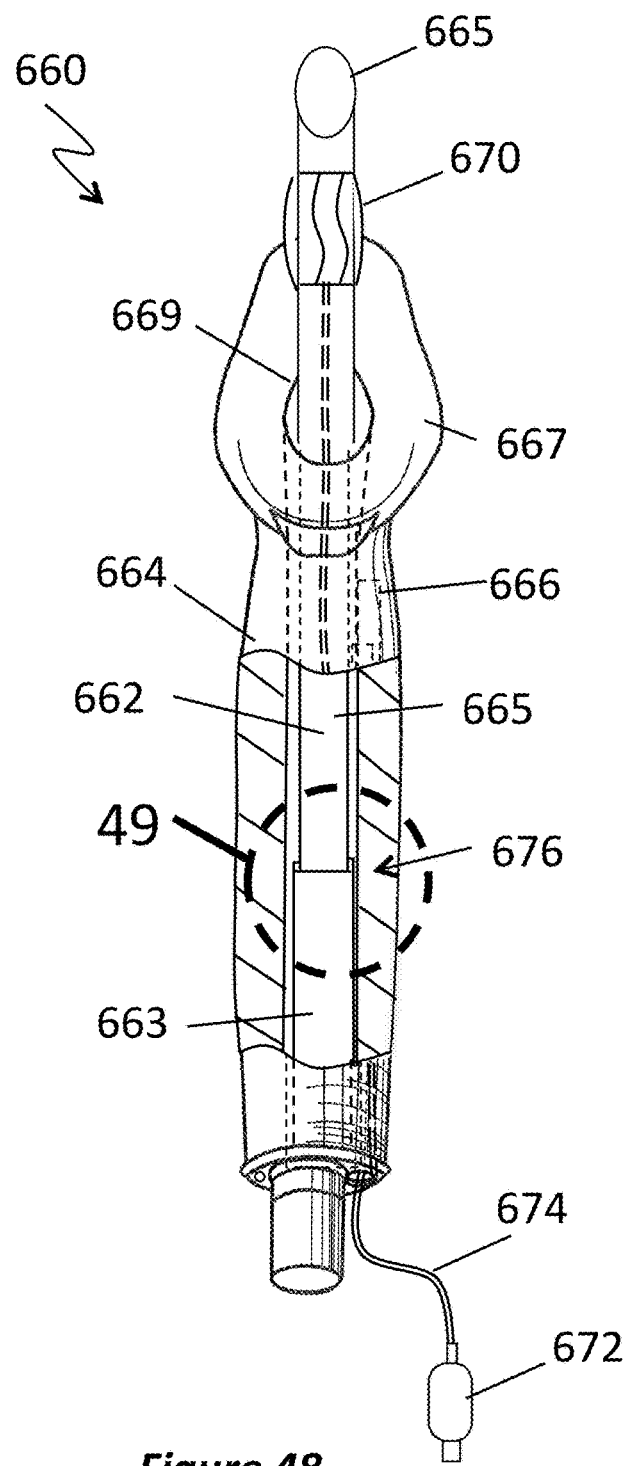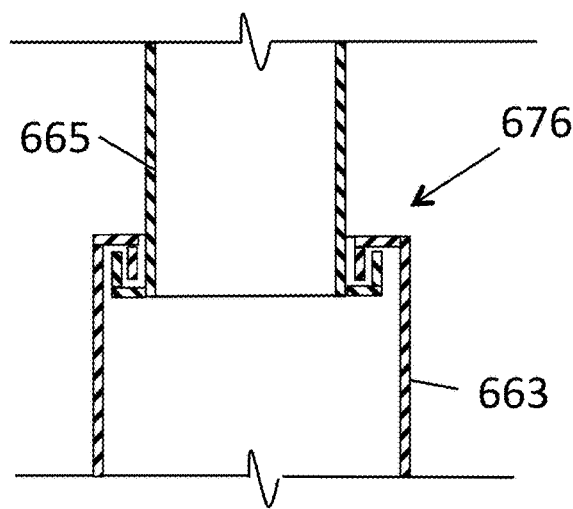
Figure 48
Figure 49

INTUBATION DEVICES AND METHODS OF USE

CROSS-REFERENCE TO RELATED APPLICATION

This application claims priority from U.S. Provisional Patent Application 62/674,255, filed on May 21, 2018, and from U.S. Provisional Patent Application 62/769,467, filed on Nov. 19, 2018, the disclosures of which are included by reference herein in their entirety.

BACKGROUND OF THE INVENTION

Technical Field

This invention is generally related to intubation devices and the use of intubation devices, for example, in operating rooms, emergency rooms, and by first responders. Specifically, aspects of the invention include devices having a laryngeal mask airway (LMA) component and an endotracheal tube (ETT) component that translates and/or rotates within the laryngeal mask airway (LMA) component, the translation and/or rotation of which is externally controlled.

Description of Related Art

Laryngeal mask airways (LMAs) are conventional supraglottic (that is, above the glottic or laryngeal opening) devices used, for example, during surgery, to maintain access to the trachea of the patient. Endotracheal tubes (ETTs) are also conventional tubes specially designed with inflatable cuffs to seal the trachea and effectively support oxygenation and ventilation, for example, during surgery.

Combination LMAs and ETT's, refereed to as "intubating laryngeal mask airways" (ILMAs) are also known in the art. ILMAs are devices that include an LMA component and an ETT component where the LMA is used as a conduit for passing the ETT into the trachea of the patient. This passage of the ETT through the LMA is typically cumbersome and difficult, and thus is often referred to as "railroading" the ETT through the LMA. In the conventional art, once the ETT of the ILMA is positioned within the patient, the LMA is removed—very carefully to prevent dislodging the ETT—and the ETT is then left in place to intubate the patient, for example, during surgery.

However, it is well recognized in the art that the manipulation and use of ILMAs, including the "railroading" of the ETT, the connecting and disconnecting of the appropriate hoses and fixtures, and the delicate removal of the LMA while not dislodging the ETT, can be difficult and time consuming. Of course, these prior art devices and practices are being performed on patients, where misstep or error can be harmful, if not life threatening.

Aspects of the invention address these and other disadvantages of the prior art by providing a unique combination of LMA and ETT that not only avoids the inconvenience and complications of the prior art, but also can provide unique opportunities for improved techniques and improved patient treatment and outcome.

SUMMARY OF THE INVENTION

According to one embodiment of the invention, a intubation device is provided comprising or including a laryngeal mask airway (LMA) component comprising a mask portion having an internal opening, and an elongated tube mounted to the mask portion, the elongated tube having an internal passageway in fluid communication with the internal opening of the mask portion; a movable endotracheal tube (ETT) component comprising an elongated tube positioned and movable within the elongated tube of the laryngeal mask airway component; and a manipulation rod operatively mounted to the ETT component, the manipulation rod adapted to allow an operator to move the ETT component within the LMA component. The manipulation rod may be adapted to allow the operator to translate and/or rotate the ETT component within the LMA component.

In one aspect, the device further comprises at least one inflatable cuff mounted to the elongated tube of the ETT component and at least one cuff inflation device operatively connected to the at least one inflatable cuff, wherein when at least partially inflated, the at least one inflatable cuff at least partially restricts fluid flow about the elongated tube of the ETT component.

In another aspect, the mask portion of the laryngeal mask airway (LMA) component may include a plurality of projections adapted to contact mating tissue, for example, a plurality of surface corrugations.

In another aspect, the intubation device may further include a sealing device adapted to minimize fluid leakage about the manipulation rod, for example, an elastomeric sealing device.

In another aspect, the intubation device may include a mask portion of the laryngeal mask airway (LMA) component having a distal end with an orogastric orifice. The laryngeal mask airway (LMA) may include a distal extension and the orogastric orifice may be located in the distal extension, and a conduit may be connected to the orogastric orifice.

In another aspect, the mask portion of the laryngeal mask airway (LMA) may include a structure adapted to receive and orient the passage of the elongated tube of the endotracheal tube (ETT) component, for example, an incline or a ramp.

According to another embodiment, an intubation device is provided. The intubation device comprises or includes a laryngeal mask airway (LMA) component comprising a mask portion having an internal opening and an elongated tube mounted to the mask portion, the elongated tube having an internal passageway in fluid communication with the internal opening of the mask portion; an endotracheal tube (ETT) component comprising an elongated tube positioned and moveable, for example, translatable and/or rotatable, within the elongated tube of the laryngeal mask airway component; and an extraction stop preventing extraction of the endotracheal tube from the internal passageway of the laryngeal mask airway component. In one aspect of this embodiment, the extraction stop may be an obstruction within the internal passageway of the laryngeal mask airway component.

In another aspect, the device may further include means for translating the endotracheal tube component within the internal passageway of the laryngeal mask airway component. For example, in one aspect, the extraction stop may be an obstruction associated with the means for translating the endotracheal tube component. In another aspect, the means for translating the endotracheal tube may be an elongated rod mounted to the endotracheal tube component, for example, mounted by a projection or "tab" to the elongated tube to the endotracheal tube component.

In another aspect, the device may further include a penetration stop preventing penetration of the endotracheal tube beyond a predetermined penetration along the internal passageway of the laryngeal mask airway component. For example, in one aspect, the penetration stop may be an obstruction within the internal passageway of the laryngeal mask airway component. In another aspect, the laryngeal mask airway component may include a slot adapted to guide translation of the endotracheal tube.

In another aspect of this embodiment of the invention, the intubation device may further include a conduit having a first opening at the distal end of the laryngeal mask airway component and a second opening at the proximal end of the laryngeal mask airway component. For example, this conduit may be a gastric fluid extraction conduit. In one aspect, for this and any other embodiment disclosed herein, the first opening at the distal end of the laryngeal mask airway component may be an orogastric orifice, as known in the art.

In another aspect, the device the device may include an endotracheal tube having one or more inflatable cuffs, for example, an inflatable cuff positioned at the distal end of the endotracheal tube.

In another aspect, the mask portion of the laryngeal mask airway component of the device, for this and any other embodiment disclosed herein, may have an extension having an opening at a distal end of the extension and an internal lumen in fluid communication with the opening, for example, an orogastric orifice. In one aspect, the extension may be a tapering extension.

In a further aspect, the mask portion of the laryngeal mask airway component of the intubation device may have a surface have projections or corrugations, for example, projections or corrugations adapted to enhance blood flow in the mating tissue.

In a still further aspect, the device may further include an inflatable balloon adapted to position the tube of the endotracheal tube component. In one aspect, the inflatable balloon may include a recess adapted to engage the tube during positioning of the tube.

Another embodiment of the invention is a method of intubating a patient, the method comprising or including: inserting an intubation device comprising or including: a laryngeal mask airway (LMA) component comprising a mask portion having an internal opening, and an elongated tube mounted to the mask portion, the elongated tube having an internal passageway in fluid communication with the internal opening of the mask portion; an endotracheal tube (ETT) component comprising an elongated tube positioned and movable (for example, translatable and/or rotatable) within the elongated tube of the laryngeal mask airway component; and an extraction stop preventing extraction of the endotracheal tube from the internal passageway of the laryngeal mask airway component; and translating the endotracheal tube (ETT) component within the laryngeal mask airway (LMA) component to insert an end of the elongated tube of the endotracheal tube (ETT) component into a trachea of a patient; translating the endotracheal tube (ETT) component to extract the end of the elongated tube of the endotracheal tube (ETT) component out of the trachea of the patient; and contacting the endotracheal tube (ETT) component against the extraction stop to prevent extraction of the endotracheal tube from the internal passageway of the laryngeal mask airway component.

In one aspect of this method, the intubation device may further comprise or include an elongated rod mounted to the endotracheal tube component; and wherein moving, for example, translating, the endotracheal tube may be practiced by moving, for example, translating, the elongated rod.

In another aspect of this method, the elongated tube of the endotracheal tube (ETT) component may comprise or include one or more inflatable cuffs; and wherein the method may further comprise inflating the one or more inflatable cuffs, for example, in the trachea of the patient.

In another aspect of this method, the mask portion of laryngeal mask airway (LMA) component may further comprise or include an inflatable balloon adapted to contact the elongated tube of the endotracheal tube (ETT) component; and wherein the method may further comprise or include inflating the inflatable balloon to deflect the elongated tube of the endotracheal tube (ETT) component.

In another aspect of this method, the mask portion of laryngeal mask airway (LMA) component may be an inflatable mask portion having at least a portion that can be inflated with a gas, such as, air, and deflated.

According to another embodiment, an intubation device is provided. The intubation device comprises or includes a laryngeal mask airway (LMA) component comprising a mask portion having an internal opening and an elongated tube mounted to the mask portion, the elongated tube having an internal passageway in fluid communication with the internal opening of the mask portion; an endotracheal tube (ETT) component comprising an elongated tube positioned within the elongated tube of the LMA component; and a manipulation rod operatively mounted to the ETT component, the manipulation rod adapted to allow an operator to move the ETT component within the LMA component. In one aspect, the manipulation rod is adapted to allow an operator to translate and/or rotate the ETT component within the LMA component.

In one aspect, the LMA component may further comprise a slot through which the manipulation rod passes, wherein movement of the manipulation rod within the slot rotates the ETT component within the LMA component.

In one aspect, the device may further comprise a projection connecting the manipulation rod to the ETT component.

In another aspect, the device may further comprise an elongated hole in the LMA component through which the manipulation devices passes. In another aspect, a sealing device may be provided in the elongated hole in the LMA component.

In another aspect, the LMA component may further comprise a conduit operatively connected to the ETT component, and wherein the device further comprises a sealing device between the conduit of the LMA component and the ETT component.

In another aspect, the device may further comprise a hollow sleeve for receiving the manipulation rod, for example, a flexible hollow sleeve.

In another aspect, the device may further comprise one or more inflatable cuffs mounted to the ETT component and a cuff inflation balloon operatively connected to the inflatable cuff. In another aspect, the device may further comprise an inflatable cuff mounted about the internal opening of the mask portion of the LMA and a cuff inflation balloon operatively connected to the inflatable cuff about the internal opening of the mask portion.

Another embodiment of the invention is a method of intubating a patient, the method comprising or including: inserting an intubation device comprising: a laryngeal mask airway (LMA) component comprising a mask portion having an internal opening and an elongated tube mounted to the mask portion, the elongated tube having an internal passageway in fluid communication with the internal opening of the mask portion; an endotracheal tube (ETT) component comprising an elongated tube positioned and movable (for example, translatable and/or rotatable) within the elongated tube of the LMA component; and a manipulation rod operatively mounted to the ETT component; and, with the manipulation rod, moving the ETT component within the LMA component to facilitate inserting the ETT component into a trachea of the patient. In one aspect of the invention, moving the ETT component may be practiced by translating the ETT component and/or rotating the ETT component.

In another aspect, the LMA component may further comprise a slot through which the manipulation rod passes, and wherein the method may further comprise moving the manipulation rod within the slot to rotate the ETT component within the LMA component.

In another aspect, the LMA component may further comprise an elongated hole through which the manipulation rod passes, and wherein the method may further comprise sealing the elongated hole to minimize fluid leakage. In another aspect, the LMA component may further comprise a conduit operatively connected to the ETT component, and wherein the method may further comprise sealing an interface between the conduit of the LMA component and the ETT component.

In one aspect, the intubation device may further comprise one or more inflatable cuffs mounted to the ETT component and one or more cuff inflation balloons operatively connected to the one or more inflatable cuff, and wherein the method may further comprise inflating the one or more inflatable cuffs on the ETT component with the one or more cuff inflation balloons.

In another aspect, the intubation device may further comprise an inflatable cuff mounted about the internal opening of the mask portion and a cuff inflation balloon operatively connected to the inflatable internal opening cuff, and wherein the method may further comprise inflating the inflatable cuff about the internal opening with the cuff inflation balloon.

These and other aspects, features, and advantages of the aspects of this invention will become apparent from the following detailed description of the various aspects of the invention taken in conjunction with the accompanying drawings

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

FIG. 2 is a right side elevation view of the intubation device shown in FIG. 1.

FIG. 3 is a top view of the intubation device shown in FIG. 2.

FIG. 4 is a bottom view of the intubation device shown in FIG. 2.

FIG. 5 is a top view of the intubation device shown in FIG. 2, partially shown in cross section to illustrate details of the intubation device.

FIG. 6 is a detail view of the intubation device shown in FIG. 5, as identified by Detail 6 shown in FIG. 5.

FIG. 7 is a bottom view of another intubation device having an internal passage according to one aspect of the invention.

FIG. 8 is a top view of another intubation device having a tube inflation cuff according to one aspect of the invention.

FIG. 16 is a partial right side elevation view of an intubation device having a tube deflecting balloon or cuff according to another aspect of the invention, the cuff shown uninflated.

FIG. 16A is a partial right side elevation view, partially in cross section, of an intubation device having a tube guide incline according to another aspect of the invention.

FIG. 17 is a partial right side elevation view of intubation device similar to FIG. 16 with the cuff shown inflated.

FIG. 18 is a partial bottom view of the intubation device shown in FIG. 17 as viewed along view line 18 in FIG. 17.

FIG. 21 is a top view of an intubation device partially shown in cross section to illustrate details of the intubation device having an ETT component with a conduit according to another aspect of the invention.

FIG. 22 is a detail view of the intubation device shown in FIG. 21, as identified by Detail 22 shown in FIG. 21.

FIGS. 23 and 24 are schematic illustrations of cross-section views of an LMA component tube portion and an ETT component tube illustrating restriction to removing the ETT component tube according to one aspect of the invention.

FIG. 25 is a partial perspective view, partially in cross section, of an intubation device having a rotatable endotracheal tube (ETT) component mounted for rotation within a laryngeal mask airway (LMA) component according to one aspect of the invention.

FIG. 26 is a partial perspective view, partially in cross section, similar to FIG. 25, where the rotatable ETT component is rotated from the position shown in FIG. 25, for example, a first position, to the position shown in FIG. 26, for example, one or more second positions, according to one aspect of the invention.

FIG. 29 is a partial perspective view, partially in cross section, of another intubation device having translatable and/or rotatable ETT component with a sealing device according to one aspect of the invention.

FIG. 30 is a cross-sectional view of the engagement of the translatable and/or rotatable ETT component with an LMA conduit having a sealing device as identified by Detail 30 in FIG. 29 according to one aspect of the invention.

FIG. 31 is a detailed cross-sectional view of the engagement of a translatable and/or rotatable ETT component with an LMA conduit having sealing device as identified by Detail 31 in FIG. 30.

FIG. 32 is a front elevation view, partially in cross section, of another intubation device having a translatable and/or rotatable ETT component having an indicator balloon according to one aspect of the invention.

FIG. 33 is a detailed cross-sectional view of a portion of the intubation device shown in FIG. 32 as identified by Detail 33 in FIG. 32.

FIG. 34 is a front elevation view, partially in cross section, of another intubation device having a translatable and/or rotatable ETT component having one or more inflatable cuffs, one or more manipulation bars or rods, and one or more cuff inflation balloons according to one aspect of the invention.

FIG. 35 is a detailed cross-sectional view of a portion of the intubation device shown in FIG. 34 as identified by Detail 35 in FIG. 34.

FIG. 48 is a front view of an intubation device having a multipart endotracheal tube (ETT) component, a balloon cuff, and balloon cuff inflation balloon according to another aspect of the invention.

FIG. 49 is a detailed cross-sectional view of the intubation device shown in FIG. 48 showing the engagement of portions of the multipart ETT component via an interlocking mechanism as identified by Detail 49 shown in FIG. 48.

DETAILED DESCRIPTION OF THE INVENTION

Figure 1:
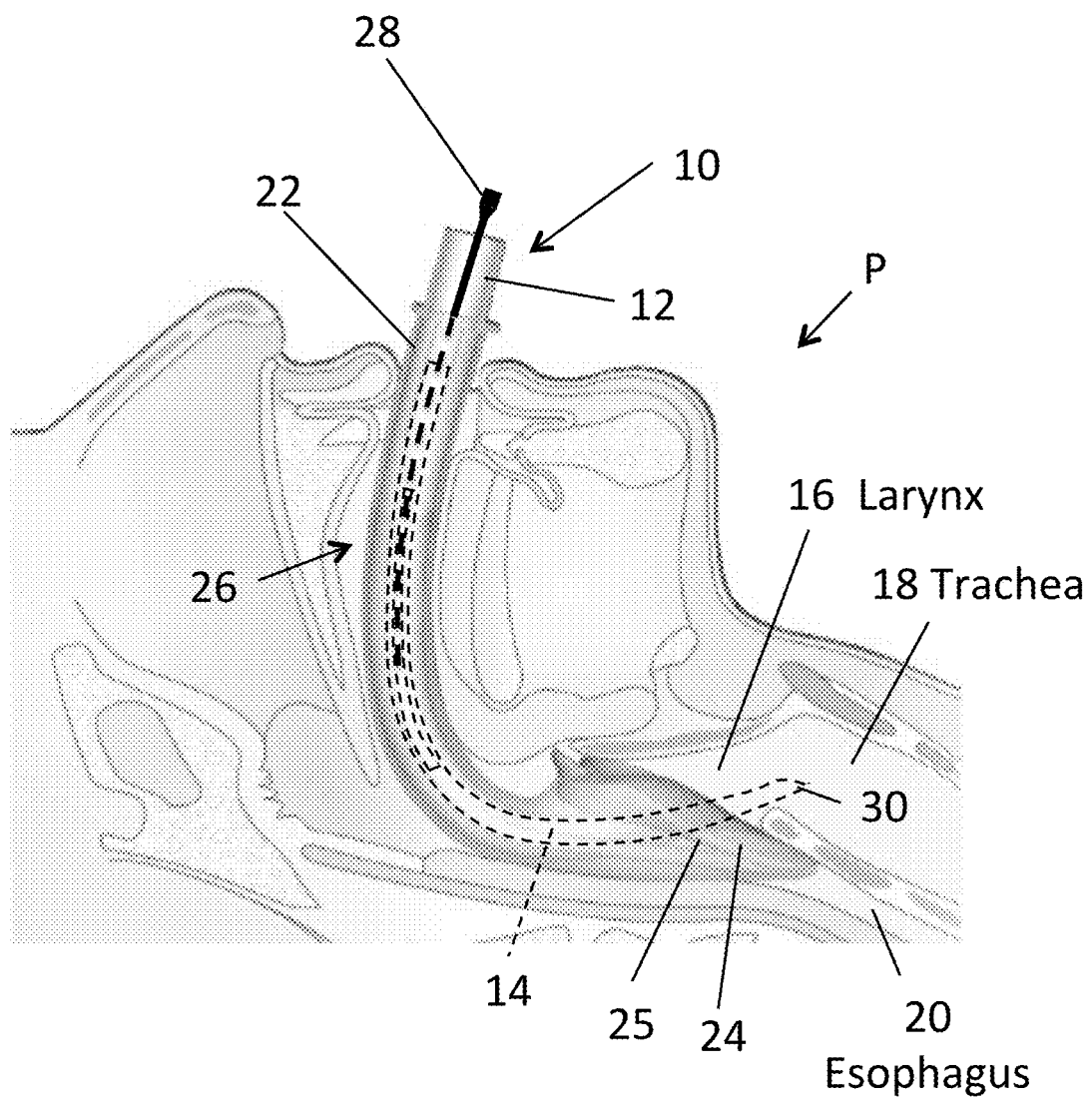
FIG. 1 is a side, cross-sectional view of the anatomy of head/neck of a patient shown by dashed line illustrating a typical positioning of the intubation device according to one aspect of the invention and its anatomical relationships as inserted in a patient.

FIG. 1 is a side view of a cross-section of the anatomy of the head/neck of a patient P illustrating a typical positioning of an intubation device 10 according to one aspect of the invention and the anatomical relationships of device 10 as inserted in patient P. As shown in FIG. 1, device 10 includes a laryngeal mask airway (LMA) component, or LMA, 12 and an endotracheal tube (ETT) component, or ETT, 14 shown in dashed line in FIG. 1. As is typical of the art, the laryngeal mask air way (LMA) component 12 is adapted to be inserted into the patient P and "mask" the larynx 16 (or path to the trachea 18) of the patient P to isolate the trachea 18. The isolation of the trachea (or "windpipe") 18 then permits the ETT component 14 to pass into the trachea 18, and, for example, avoid the esophagus 20. The LMA component 12 may typically include a tube portion 22 and a mask portion 24 having an opening, or internal opening, 25, through which the ETT component 14 passes.

According to aspects of the invention, the ETT component 14 of device 10 is mounted for translation and/or rotation within the LMA component 12 of device 10, and may be prevented, for example, substantially prevented during use, from being removed or extracted from the LMA component 12. As disclosed herein, though many different means may be provided for translating and substantially preventing extraction or removal of ETT component 14, in one aspect, device 10 includes at least one extraction stop, generally indicated by arrow 26 in FIG. 1, which substantially prevents extraction or removal of the endotracheal tube component 14 from the internal passageway of the laryngeal mask airway component 12.

As also shown in FIG. 1, the translation of ETT component 14 within LMA component 12 may be practiced by withdrawing or inserting one or more bars or rods 28 into LMA component 12, where the bar or rod 28 is operatively connected to the ETT component 14. According to one aspect of the invention, one or more rods 28, or "manipulation rods," may be mounted to ETT component 14 and when rod 28 is moved or translated, for example, by an attending anesthesiologist, the ETT component 14 may be translated along LMA component 12, for example, to extend the distal end 30 of ETT component 14 into or extract the distal end 30 of ETT component 14 from or out of the larynx 16 and/or trachea 18 of patient P. In one aspect, bar or rod 28 may be manipulated by an automated manipulator, for example, by an actuator or a robotic arm end, and the like.

FIG. 2 is a right side elevation view of intubation device 10 shown in FIG. 1. FIG. 3 is a top plan view of intubation device 10 shown in FIG. 2. FIG. 4 is a bottom view of intubation device 10 shown in FIG. 2. Though the intubation device shown in FIGS. 1 through 4 is presented as a modification to an existing LMA device provided by Intersurgical Ltd. of Berkshire, UK, aspects of the present invention may be provided by any form of LMA device, for example, a modified existing LMA device or an LMA component specially designed and fabricated to implement aspects of the present invention.

As shown in FIGS. 2 through 4, intubation device 10 includes an LMA component 12 and an ETT component 14, and LMA component 12 includes a body or tube portion 22 and a mask portion 24. ETT component 14 includes an elongated hollow tube 15 having a distal end 30 and a proximal end 32.

According to aspects of the invention, the ETT component 14 of device 10 is mounted for translation within the LMA component 12 of device 10, for example, as indicated by double arrows 34 in FIGS. 2 through 4. As shown in FIGS. 2 through 4, according to one aspect, withdrawing or inserting one or more bars or rods 28 into LMA component 12 may effect the translation of ETT component 14 within LMA component 12. According to one aspect of the invention, the one or more rods 28 are mounted to ETT component 14 and when rod 28 is moved or translated, for example, as indicated by double arrow 34, the ETT component 14 may be moved or translated along LMA component 12. As shown in FIGS. 2 through 4, rod or bar 28 may include a knob or handle 37 to facilitate handling of rod 28 while translating ETT component 14 within LMA component 12.

As shown in FIG. 3, according to one aspect of the invention, tube 15 of ETT component 14 may typically extend beyond the LMA component 12 a distance 27. For example, in one aspect, the distance 27 from the opening 25 in the mask portion 24 of LMA component 12, for instance, from the distal end of opening 25, may range from about 5 centimeters [cm] to about 30 cm. In one aspect, the distance 27 may range from 10 cm to 22 cm, for example, between 15 cm and 20 cm.

The opening 25 in the mask portion 24 may be circular, elliptical, rounded rectangular, or pear-shaped (as shown). In one aspect, opening 25 may be elliptical or rounded rectangular and have a narrower width (that is, a narrower medial to lateral dimension) than height (that is, the antero-posterior dimension). According to one aspect, the narrower width of opening 25 may function as a guide for tube 15 and facilitate the passage of the distal end 30 of tube 15 into the trachea (or other cavity) of the patient. In one aspect, the aspect ratio (that is, height-to-width ratio) of opening 25 may range from about 1.25 to 4.0, but is typically between about 1.5 and 2.0.

According to one aspect, the translation of ETT component 14 within LMA component 12 may be limited or substantially prevented by one or more obstructions or "stops" or "extraction stops" 26, generally identified by arrow 26 in FIG. 2 through 4. An example of one obstruction or stop 26 that may be used to limit or prevent translation of ETT component 14 within LMA component 12 is shown and described with respect to FIGS. 5 and 6.

FIG. 5 is a top view of intubation device 10 shown in FIG. 2, partially shown in cross section to illustrate details of an aspect of the invention. FIG. 6 is a detail view of intubation device 10 shown in FIG. 5, as identified by Detail 6 shown in FIG. 5. As shown in FIGS. 5 and 6, rod or bar 28 may be mounted to an extension, ring, projection, bracket, clamp, or "tab" 36 that projects from rod 28 and engages ETT component 14, for example, engages hollow tube 15 of ETT component 14. Typically, projection 36 may be rigidly mounted to rod 28 and projection 36 may be rigidly mounted to ETT component 14, for example, with an appropriate adhesive and/or mechanical fastener. In one aspect, projection 36 may be formed integrally with rod 28 and/or formed integrally with tube 15, for example, integrally molded during fabrication, and then, as appropriate, mounted to rod 28 or tube 15, respectively, for example, with an adhesive or fastener.

According to one aspect of the invention, a recess, cavity, or slot 38 may be provided in tube portion 22 of LMA component 12 and adapted to receive projection 36 and/or rod 28. In one aspect, the walls of recess or slot 38 may function to guide the movement or translation of projection 36 and/or rod 28. As shown most clearly in FIG. 6, in one aspect, the obstruction or stop 26 may comprise an end wall of recess or slot 38, where a surface of projection 36 contacts the end wall or stop 26 to prevent further movement or transition of projection 36, and thus prevents further movement or translation of rod 28 and tube portion 15 of ETT component 14.

According to one aspect of the invention, the translation of ETT component 14 within LMA component 12 may be limited or substantially prevented by one or more obstructions or "stops" or "insertion stops" 40, shown in FIG. 5. For example, insertion stop 40 may comprise an end wall of recess or slot 38, where a surface of projection 36 contacts the end wall or stop 40 to prevent further movement or transition of projection 36, and also of rod 28 and tube portion 15 of ETT component 14.

Figure 6A:
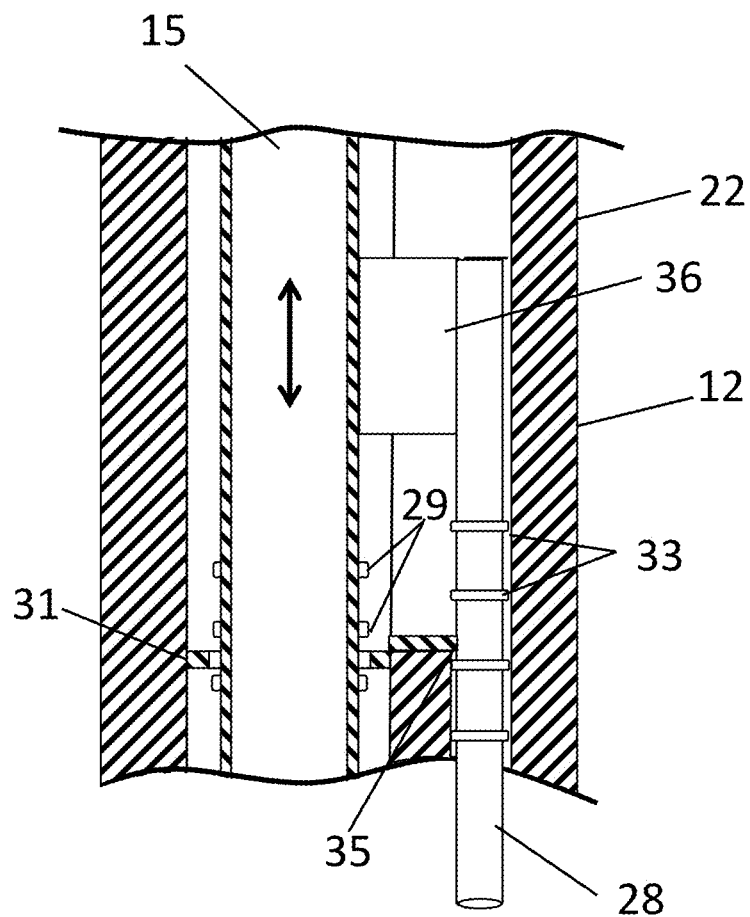
FIG. 6A is a detail view similar to FIG. 6 illustrating another aspect of the invention.

FIG. 6A is a detail view, similar to FIG. 6, illustrating another aspect of the invention. As shown in FIG. 6A, aspects of the invention may provide a tactile feedback mechanism when moving or translating ETT component 14 within LMA component 12. In one aspect, rod or bar 28 and/or ETT component 14 may include structures that contact or interact with other structures, for example, one or more detents, in tube portion 22 of LMA component 12 that indicate to the user when a predetermined deflection or translation of ETT component 14 within LMA component 12 occurs. For example, in on aspect, tube 15 of ETT component 14 may include projections or ribs 29, for example, external annular projections or ribs 29, that contact one or more projections or ribs 31, for example, internal annular projections or ribs 31, on LMA component 12, for example, along the internal surface of tube portion 22. For instance, in one aspect, one or both of projections 29 on tube 15 and/or projections 31 on LMA component 14 may be flexible, for example, elastomeric, and provide at least some resistance to the passage of projections 29 passed projection 31. In one aspect, the inside dimension of projections or ribs 31 may be substantially equal to or smaller than the outside dimension of projections or ribs 29, wherein at least some contact or interference occurs when tube 15 is translated relative to tube portion 22. The predetermined spacing between projections 29, and thus the predetermined deflection or translation of ETT component 14, may vary from 5 mm to 5 cm, but is typically about 10 mm (that is, about 1 cm).

In another aspect, as shown in FIG. 6A, rod or bar 28 may include projections or ribs 33, for example, external annular projections or ribs 33, that contact one or more projections or ribs 35, for example, internal annular projections or ribs 35, in LMA component 12, for example, along the hole through which rod 28 passes. For instance, in one aspect, one or both of projections 33 on bar 28 and/or projections 35 on LMA component 12 may be flexible, for example, elastomeric, and provide at least some resistance to the passage of projections 33 passed projection 35. In one aspect, the inside dimension of projections or ribs 35 may be substantially equal to or smaller than the outside dimension of projections or ribs 33, wherein at least some contact or interference occurs when rod 28 is translated relative to tube portion 22. The predetermined spacing between projections 33, and thus the predetermined deflection or translation of rod 28, may vary from 5 mm to 5 cm, but is typically about 10 mm (that is, about 1 cm). Other tactile feedback mechanisms or detents that may be used with aspects of the invention will be apparent to those of skill in the art.

Figure 6B:
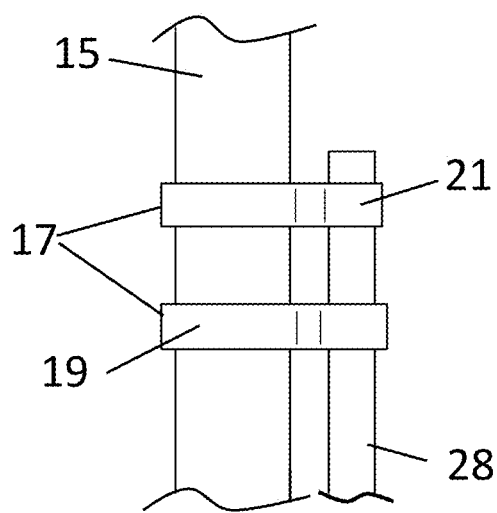
FIG. 6B is a partial plan view of an alternate mounting of a manipulation rod to an endotracheal tube according to one aspect of the invention.
Figure 6C:
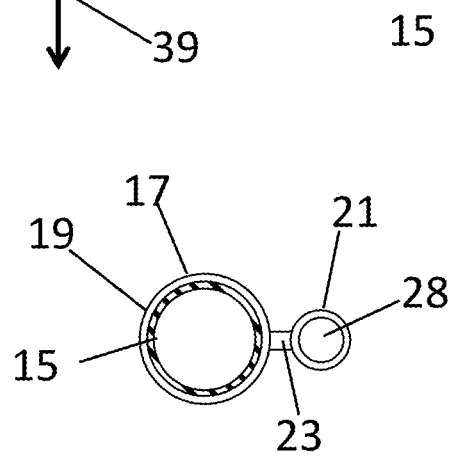
FIG. 6C is an end view, partially in cross section of the alternate mounting shown in FIG. 6B.

FIG. 6B is a partial plan view of an alternate mounting of rod 28 to tube 15 of ETT component 14 according to one aspect of the invention. FIG. 6C is an end view, partially in cross section, of the alternate mounting shown in FIG. 6B. As shown in FIGS. 6B and 6C manipulation bar or rod 28 may be mounted to tube 15 by one or more clamps or brackets 17, for example, a metal, plastic, or rubber bracket having lobes 19 and 21 attached to connecting bar 23 and appropriately sized to be clamped to, to be crimped on, or mounted with an adhesive to rod 28 and tube 15, respectively FIG. 7 is a bottom view of another intubation device 50 having a feed or extraction lumen, passage, or conduit 52, for example, a gastric drainage port, or an orogastric port, according to one aspect of the invention. According to this aspect, intubation device 50 may typically comprise an LMA component 54 having a body or tube portion 56 and a mask portion 58, and an ETT portion 60, having a tube 61, translatable within LMA component 54, for example, by means of a rod or bar 62, as discussed herein. In the aspect of the invasion shown in FIG. 7, intubation device 50 includes a conduit or lumen 52 having an open first end 64, or gastric orifice, located in the distal end of LMA component 54, for example, in mask portion 58, and an open second end 66 located in the proximal end of LMA component 54. According to aspects of the invention, conduit or lumen 52 is located in mask portion 56 so that, when inserted over the larynx (see FIG. 1), the open first end 64 of conduit or lumen 52 is positioned in fluid communication with the esophagus 20 of patient P (see FIG. 1), and is available to introduce or extract fluids, for example, gastric fluids, from esophagus 20, if needed. In one aspect, open second end 66 of conduit or lumen 52 may be exposed to vacuum, for example, via a conventional vacuum connector, to withdraw fluid from esophagus 20, for example, to withdraw gastric fluids. In one aspect, conduit or lumen 52 may be referred to as "a gastric drainage port," as known in the art, and functions accordingly.

FIG. 8 is a top view of another intubation device 70 having a tube inflation cuff 72 according to another aspect of the invention. According to this aspect, intubation device 70 may typically comprise an LMA component 74 having a body or tube portion 76 and a mask portion 78, and an ETT portion 80, having a tube 81, translatable within LMA component 74, for example, by means of a rod or bar 82, as discussed herein. In the aspect of the invention shown in FIG. 8, intubation device 70 includes an inflation balloon or cuff 72 mounted to tube 81 of ETT component 80 and an inflation conduit or lumen 84 in fluid communication with the inside of cuff 72. According to aspects of the invention, cuff 72 may operate and function as a conventional cuff as known in the art, for example, cuff 72 may inflate or expand when filled with a fluid, for example, pressurized gas, such as, air, and restrict or prevent the flow of fluid through the annular passage defined by tube 81 and the cavity in which tube 81 and cuff 72 are positioned, such as, a trachea.

As shown in FIG. 8, conduit or lumen 84 from cuff 72 may pass from cuff 72 along tube 81 and have an open end 86 in the proximal end of LMA component 74. As shown, in one aspect, conduit or lumen 84 may be connected to an external conduit or pipe 88 that can be connected to a source of pressurized gas, such as, air. As shown, in one aspect, conduit 88 may be operatively connected to a inflation pilot balloon 90, as known in the art, for inflating cuff 72, though any source of pressurized gas may be used.

According to an aspect of the invention, with ETT component 80 being translatable within LMA component 74, conduit or lumen 84 may be mounted on or in tube 81 of ETT component 80 and conduit or lumen 84 may translate with ETT component 80. For example, in one aspect, at least a portion of conduit or lumen 84 may be mounted on or in tube 81, for example, molded into tube 81, and then a least a portion of conduit or lumen 84 may detach from or disengage from tube 81 and be mounted to rod or bar 82. In one aspect, at least a portion of conduit or lumen 84 may be molded into rod or bar 82. Accordingly, in one aspect, conduit or tube 84 may exit LMA portion 74 through the same opening as the rod 82 exits LMA component 74.

Figure 9:
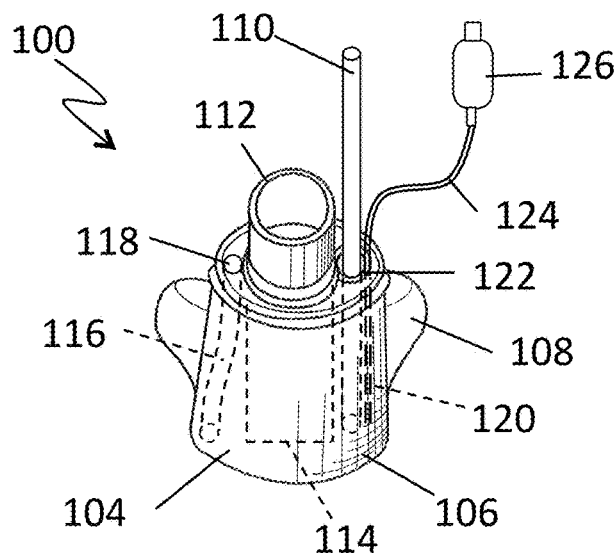
FIG. 9 is a front-end view of an intubation device according to one aspect of the invention.

FIG. 9 is a front end view of an intubation device 100 according to one aspect of the invention. As shown in FIG. 9, in this aspect, intubation device 100 may typically comprise an LMA component 104 having a body or tube portion 106 and a mask portion 108, and an ETT component (not shown) translatable within LMA component 104, for example, by means of a rod or bar 110, as discussed herein. As shown in FIG. 9, in a typical aspect, body portion 106 of LMA component 104 may include an appropriate connector 112 adapted to accept conventional conduits (not shown) and connector 112 may be placed in fluid communication with the internal passage 114 of LMA component 104.

As also shown in FIG. 9, LMA component 104 may include one or more lumen or conduits 116 having open ends 118. The one or more lumen or conduits 116 may communicate with an inflatable cuff, for example, cuff 72 shown in FIG. 8, or inflatable balloon 202 shown in FIGS. 16, 17, and 18, or an inflatable cuff associated with mask portion 108. According to aspects of the invention, open ends 118 of lumen or conduit 116 may be located anywhere on the proximal end of body 106, including on the sides of body 106 or anywhere about the end of body 106, for example, on any surface of body 106 outside of connector 112.

As also shown in FIG. 9, inflation lumen or conduit 120 may be associated with bar or rod 110 and exit body 106 via the same opening 122 through which bar or rod 110 exits body 106. However, in another aspect, inflation lumen or conduit 120 may exit body 106 via a different opening from which bar or rod 110 exits body 106. As also shown in FIG. 9, inflation lumen or conduit 120 may communicate with external conduit 124 and with an inflation pilot balloon 126, as known in the art.

Figure 10:
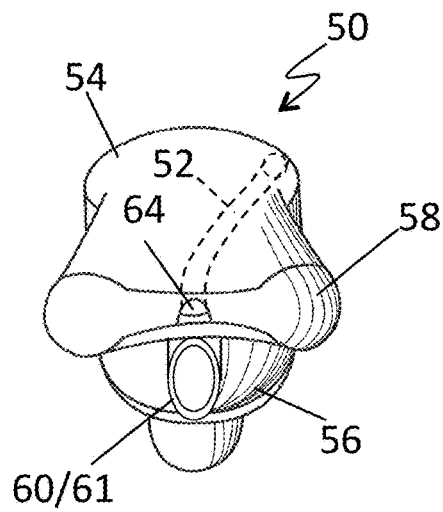
FIG. 10 is a rear end view of the intubation shown in FIG. 7 having a feed or extraction lumen, passage, or conduit according to one aspect of the invention.

FIG. 10 is a rear end view of the intubation device 50 shown in FIG. 7 having a feed or extraction lumen, passage, or conduit 52, for example, a gastric drainage port, according to one aspect of the invention. According to this aspect, intubation device 50 may typically comprise an LMA component 54 having a body or tube portion 56 and a mask portion 58, and an ETT portion 60, having a tube 61.

Figure 11:
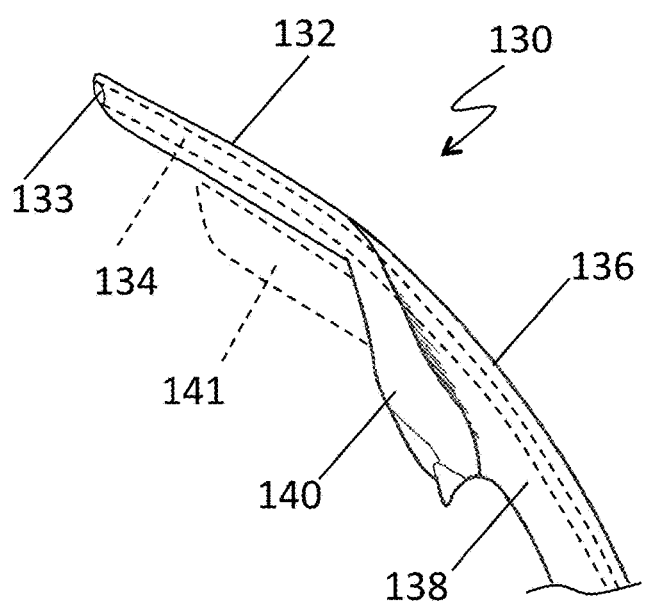
FIG. 11 is a partial right side elevation view of an intubation device having an extension having an extended feed or extraction lumen, passage, or conduit.
Figure 12:
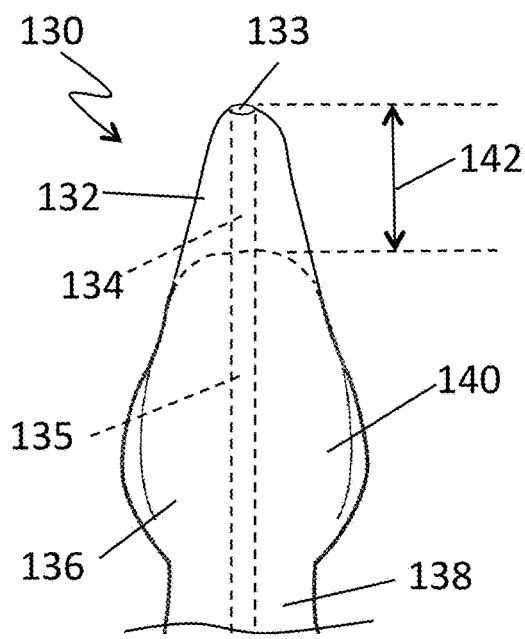
FIG. 12 is a partial bottom view of the intubation device shown in FIG. 11.

FIG. 11 is a partial right side elevation view of an intubation device 130 having an extension 132 having an extended feed or extraction lumen, passage, or conduit 134, for example, a gastric drainage port, according to another aspect of the invention. FIG. 12 is a partial bottom view of the intubation device 130 shown in FIG. 11.

According to this aspect, as is typical of aspects disclosed herein, intubation device 130 may typically comprise an LMA component 136 having a body or tube portion 138 and a mask portion 140, and an ETT component 141 (shown in phantom in FIG. 11) translatable within LMA component 136, as discussed herein.

As shown in FIGS. 11 and 12, in this aspect, the mask portion 140 of LMA component 136 of intubation device 130 may include an extension 132 having an orifice or opening 133, or orogastric orifice, and a lumen, passage, or conduit 134 in fluid communication with lumen or conduit 135 in LMA component 136. According to this aspect, the extension 132 having the opening 133 may be adapted to extend, for example, to extend from the location of conventional LMA mask, wherein, when inserted into a patient, extension 132 is capable of extending into the esophagus, for example, into the upper esophagus. It is envisioned that extension 132 may possibly extend near or into the stomach. In one aspect, the extension 132 having conduit 134 may provide closer access to the stomach than prior art intubation devices.

In one aspect, intubation device 130 may extend a distance 142 beyond the length or extent of a conventional LMA (shown in phantom in FIG. 12). Distance 142 may be at least 10 millimeters [mm] longer than the length of a conventional LMA. In one aspect, the distance 142 may be at least 20 mm longer, or at least 30 mm longer, or at least 50 mm longer than conventional devices.

In the aspect of the invention shown in FIGS. 11 and 12, extension 132 is generally depicted in the shape of a truncated frustum, that is, narrowing or tapering while extending from mask portion 140. However, it is envisioned that extension 132 having opening 133 and lumen, conduit, or passage 134 may assume a broad range of shapes and geometries while providing the desired function. In one aspect, extension 132 may be cylindrical in shape, for example, circular cylindrical, elliptical cylindrical, or polygonal cylindrical. In one aspect, the cylindrical shape of extension 132 may taper while extending from mask portion 140, as in the tapered shape shown in FIG. 12. For instance, in one aspect, extension 132 may comprise a hollow cylinder, for example, a circular or non-circular tube extending from, for example, mask portion 140, and into the esophagus, and possibly extending even to the stomach. Other shapes and geometries for extension 132 which provide the desired function will be apparent to those of skill in the art while not deviating from the operations and functions of the disclosed invention.

Figure 13:
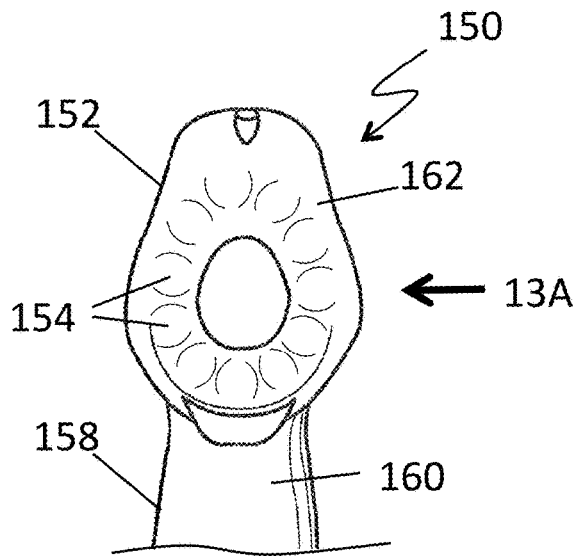
FIG. 13 is a partial top plan view of an intubation device having a mask portion with surface corrugations or projections according to another aspect of the invention.
Figure 14:
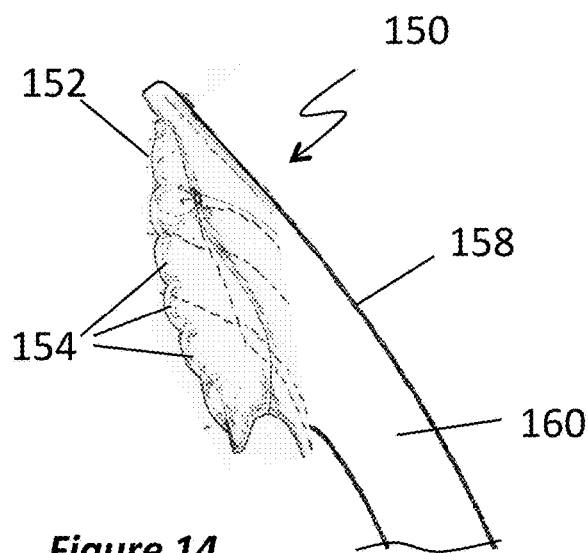
FIG. 14 is a partial right side elevation view of the intubation device shown in FIG. 13.
Figure 13A:
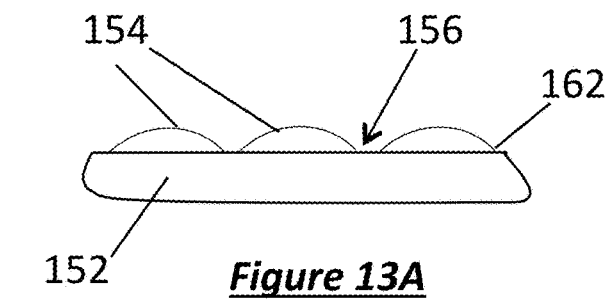
FIG. 13A is a partial side elevation view of the intubation device shown in FIG. 13 as viewed along view direction 13A shown in FIG. 13.

FIG. 13 is a partial top view of an intubation device 150 having a mask portion 152 with surface corrugations or projections 154 according to another aspect of the invention. FIG. 13A is a partial side elevation view of the intubation device 150 shown in FIG. 13 as viewed along view direction 13A shown in FIG. 13. FIG. 14 is a partial right side elevation view of the intubation device 150 shown in FIG. 13. Intubation device 150 may typically include an LMA component 158 having a body or tube portion 160 and mask portion 152, and an ETT component (not shown) translatable within LMA component 158, for example, by means of a rod, as disclosed herein.

As shown in FIGS. 13, 13A, and 14, in this aspect of the invention, at least a portion of a surface 162 of LMA mask portion 152 comprises a plurality of corrugations or projections 154 that extend above surface 162 and define a plurality of recesses, depressions, or "valleys" 156 between or about projections 154. According to one aspect of the invention, projections 154 and recesses 156 provide at least some reduction in the area of contact between the surface 162 of mask portion 152 and the surface of the tissue contacted by mask portion 152, for example, the laryngeal mucosa. According to aspects of the invention, it is believed that contact, for example, substantially uniform contact, between the surface 162 of mask portion 152 with the mating surface of the tissue and the consequent compression of the surface of the mating tissue may undesirably reduce blood circulation in the area contacted and compressed. For example, the potential for restricting blood flow may be exacerbated when a mask portion 152 contacts the tissue for an extended period of time, for example, while the patient is undergoing surgery. According to aspects of the invention, it is believed that the reduction of the contact area between surface 162 and the contacted tissue may limit or prevent restricting blood flow in or about the tissue contacted by intubation device 150. For example, it is believed that the depressions or "valleys" 156 between or around projections 154 may not expose the mating tissue surface to contact and compression, and thus desirably not limit blood flow in the areas of the depressions or valleys 156.

According to one aspect of the invention, projections or corrugations 152 may cover only a portion of the surface 162 of mask portion 152, for example, projections or corrugations 152 may extend over portions of surface 162 that are more likely to limit compression and not diminish blood flow in the mating tissue. In one aspect, projections or corrugations 152 may define an annular region about surface 162, for example, where a portion of surface 162 inside and/or outside the annular region of surface 162 is devoid of projections or corrugations 152.

As shown most clearly in FIG. 13A, in one aspect, projections or corrugations 154 may be curved, for example, circular or semicircular in shape, for example, having a radius ranging from about 1 mm to about 50 mm. In other aspects, projections or corrugations 154 may be curvilinear, for example, having planar and/or non-planar surfaces. For example, in one aspect, projections or corrugations 154 may be polygonal in cross section, for example, defining planar surfaces, converging points or apexes, rounded apexes, or pyramidal structures adapted to contact the mating tissue surface. Other effective shapes for projections 154 will be apparent to those of skill in the art.

The height or elevation of projections 154 above surface 162 may range from about 1 mm to about 25 mm, but may typically be between about 5 mm and about 15 mm in height above surface 162. The widths or diameters of projections 154 may range from about 1 mm to about 25 mm, but may typically be between about 5 mm and about 15 mm in width or diameter. In one aspect, the dimensions of projections or corrugations 154 may vary; for example, adjacent projections 154 may have varying heights above surface 162, and/or varying widths, and/or varying diameters, and/or varying radii.

Figure 15:
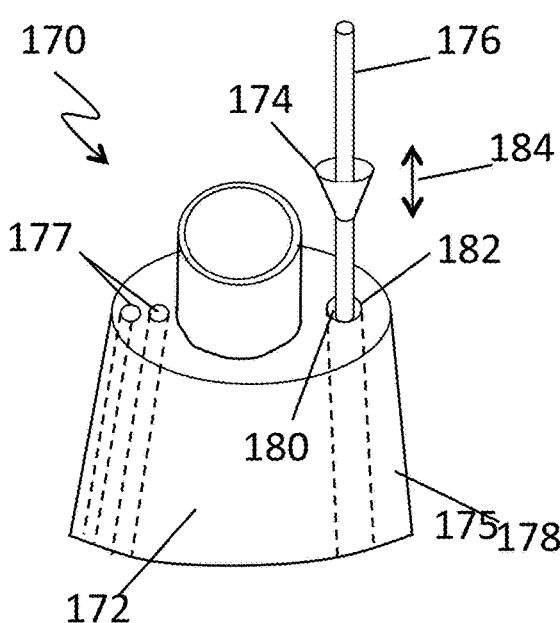
FIG. 15 is a front end perspective view of an intubation device having a sealing device for the tube-translating rod or bar according to another aspect of the invention.

FIG. 15 is a front end perspective view of an intubation device 170 having an LMA component 172 having a sealing device 174 for the manipulation or tube-translating rod or bar 176, as discussed herein, according to another aspect of the invention. Intubation device 170 may typically include an LMA component 172 having a body or tube portion 178 and passages or lumen 177 as disclosed herein, and a mask portion (not shown), and an ETT component (not shown) translatable within LMA component 172, for example, by means of a rod 176, as disclosed herein. In one aspect, two or more sealing devices or elements 174 may be provided on one or more rods 176.

As shown in FIG. 15, in this aspect, rod or bar 176 includes some form of sealing device or element 174 adapted to at least partially seal the annular space 180 about the outside surface of rod 176 and the inside surface of hole 182—through which rod 176 passes—to limit or prevent the passage of fluids. In one aspect, as indicated by double arrow 184, sealing element 174 may be adapted to translate along rod 176, for example, to vary the location of sealing element 174 while rod 176 is reciprocated within hole 182. In one aspect, sealing element 174 may also be rotatable about rod 176. In one aspect, sealing element 174 may be substantially fixed on rod 176, for example, to ensure engage of sealing element 174 with hole 182 when rod 176 is positioned in a predetermined position. In one aspect, sealing element 174 on rod 176 may be positioned within LMA component 172 and at least partially seal the annular space 180 between the inside surface of hole 182 and the outside surface of rod 176.

In the aspect of the invention shown in FIG. 15, sealing element 174 is frusto-conical in shape, for example, having a smaller diameter directed toward hole 182. However, according to aspects of the invention, sealing element 174 may comprise any conventional shape adapted to seal the annular space 180, for example, depending upon the shape of annular space 180. For example, in one aspect, sealing element 174 may not be circular and may not be conical and provide the desired sealing function.

In one aspect, sealing element 174 may be at least partially made from an elastomeric or "rubber" material, for example, where sealing element 174 may at least partially elastically deform when engaging hole 182 to provide a resilient seal. In one aspect, sealing element 174 may comprise at least a portion made from a natural polymer, such as, polyisoprene rubber, or a synthetic polymer, such as, a neoprene, a thermoplastic elastomer, a thermoplastic rubber, and a polyvinyl chloride, or an ethylene propylene diene monomer (EPDM) rubber, and the like. In one aspect, sealing element 174 may be fabricated entirely from an elastomeric material, for example, one or more of the above materials.

Figure 15A:
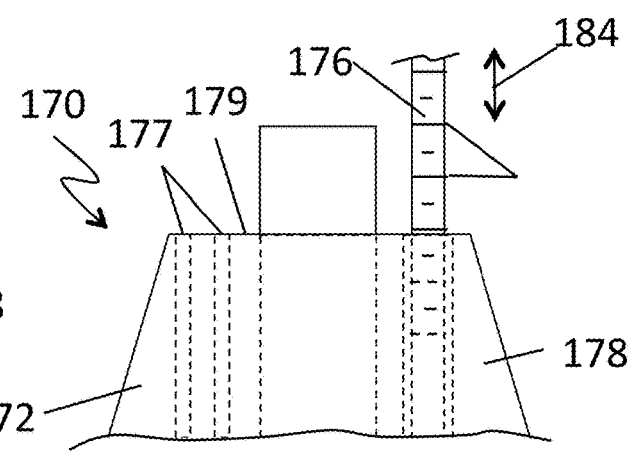
FIG. 15A is an elevation view of a front end of the intubation device shown in FIG. 15 having translation indicia on the tube-translating rod or bar according to another aspect of the invention.

FIG. 15A is an elevation view of a front end of intubation device 170 shown in FIG. 15 having translation indicia 175 on the tube-translating rod or bar 176 according to another aspect of the invention. As shown in FIG. 15A, in this aspect, intubation device 170 having an LMA component includes one or more indicia 175 reflecting or indicating the translation of the tube-translating rod or bar 176, as discussed herein. Intubation device 170 may typically include an LMA component 172 having a body or tube portion 178 and passages or lumen 177 as disclosed herein, and a mask portion (not shown), and an ETT component (not shown) translatable within LMA component 172, for example, by means of a rod 176, as disclosed herein.

As shown in FIG. 15A, indicia 175 may include lines or notches or other indicia in or on the surface of rod 176, wherein movement or translation of rod 176 (and thereby translation of an ETT component (not shown) to which rod 176 is mounted) is indicated by the relative deflection of indicia 175 on rod 176. Though the movement of indicia 175 may be visually detected in comparison to the position (for example, a relatively stationary position relative to rod 176) of any structure on LMA component 172, according to one aspect of the invention, the relative movement of rod 176 indicated by indicia 175 may be indicated relative to the end surface 179 of LMA component 172, or to a corresponding indicator mounted on or in end surface 179 of LMA component 172. Other indicia reflecting or indicating the translation of the tube-translating rod or bar 176 that may be used with aspects of the invention will be apparent to those of skill in the art.

FIG. 16 is a partial right side elevation view of an intubation device 200 having a tube deflecting balloon or cuff 202 according to another aspect of the invention. In FIG. 16, the cuff 202 is shown uninflated. FIG. 17 is a partial right side elevation view of intubation device 200 similar to FIG. 16 with the cuff 220 shown at least partially inflated. Intubation device 200 may typically include an LMA component 204 having a body or tube portion 206 and a mask portion 208, and an ETT component 210 having a tube 212 translatable within LMA component 204, for example, by means of a rod (not shown), as disclosed herein. In one aspect, tube 202 may include its own cuff, for example, cuff 72 as shown and described with respect to FIG. 8. As shown in FIGS. 16 and 17, mask portion 208 may include an extension 214 having an extended feed or extraction lumen, passage, or conduit 216 as disclosed in described with respect to FIGS. 11 and 12.

As shown in FIGS. 16 and 17, in one aspect, LMA component 204 includes one or more inflatable balloons 202 positioned and adapted to vary the position or orientation of tube 212 of ETT portion 210. According to this aspect, balloon 202 may be inflated by any conventional source of fluid, for example, pressurized air. In one aspect, as shown in FIG. 16, balloon 220 may be inflated via one or more passages, conduits, or lumen 203 operatively connected to a source of pressurized fluid, including a liquid or a gas. In one aspect, passage, conduit, or lumen 203 may communicate with an opening in the proximal end of tube portion 206 of LMA component 204, for example, one of the holes 177 shown in FIG. 15. In one aspect, balloon 202 and lumen 203 may be operatively connected to an inflation pilot balloon, for example, inflation pilot balloon 126 shown in FIG. 9.

As shown most clearly in FIG. 17, in one aspect, with the at least partial inflation of balloon 202, tube 212 may be re-positioned, for example, from a first position 218 (for example as shown in FIG. 16) to a second position 220 (as shown in FIG. 17), as indicated by arrow 222. FIG. 18 is a partial bottom view of intubation device 200 shown in FIG. 17 as viewed along view line 18 in FIG. 17.

As shown in FIGS. 17 and 18, when at least partially inflated, balloon 202 contacts and deflects tube 202, and according to one aspect, may also direct or orient tube 202 in a desired direction and/or orientation, for example, past the larynx and into the trachea. In one aspect, balloon 202 may include one or more depressions or recesses 205 positioned and shaped to guide the deflection of tube 212. As shown in FIG. 18, in one aspect, balloon 220 may be "kidney bean shaped" having two lobes and the recess 205 between the two lobes of the "kidney bean." For example, in one aspect, recess 205 in balloon 202 may be shaped to at least partially capture or retain tube 212 and direct tube 212 in a desired direction or orientation. It is also envisioned that in one aspect, two or more balloons 205 may be provided, and the two or more balloons 205 may be inflated individually or together through one or more lumen 203 to guide the positioning of tube 212. For example, in one aspect, the lobes of the kidney bean shaped balloon 202 shown in FIG. 18 may comprise individual, separate balloons 202A and 202B, each inflated by separate lumen 203 and separate sources of pressurized fluid. In this aspect, the separate balloons 202A and 202B may be separately inflated and/or their inflation varied to facilitate positioning of tube 212. It is envisioned that 3 or more balloons 202 having 1 or more feeding lumens and sources of pressurized fluid may also be used to facilitate positioning of tube 212.

FIG. 16A is a partial right side elevation view, partially in cross section, of an intubation device 201 having a tube guiding structure 207 according to another aspect of the invention. Intubation device 201 may typically include an LMA component 209 having a body or tube portion 211 and a mask portion 213, and an ETT component 215 having a tube 217 translatable within LMA component 209, for example, by means of a rod (not shown), as disclosed herein. According to this aspect of the invention, any one of the mask portions disclosed herein may include a structure 207, for example, an incline or a ramp, positioned and oriented to facilitate the passage of tube 217 through the opening in mask portion 213. In one aspect, structure 207 may be a plate or panel having a planar surface oriented to receive and direct tube 217 through mask portion 213. In another aspect, structure 207 may be a plate or panel having a curvilinear or radiused surface oriented to receive and direct tube 217 through mask portion. In a further aspect, structure 217 may comprise a surface of the internal passage through mask portion 213 that is a planer, a curvilinear, or a radiused surface oriented to receive and direct tube 217 through mask portion.

Figures 19, 20:
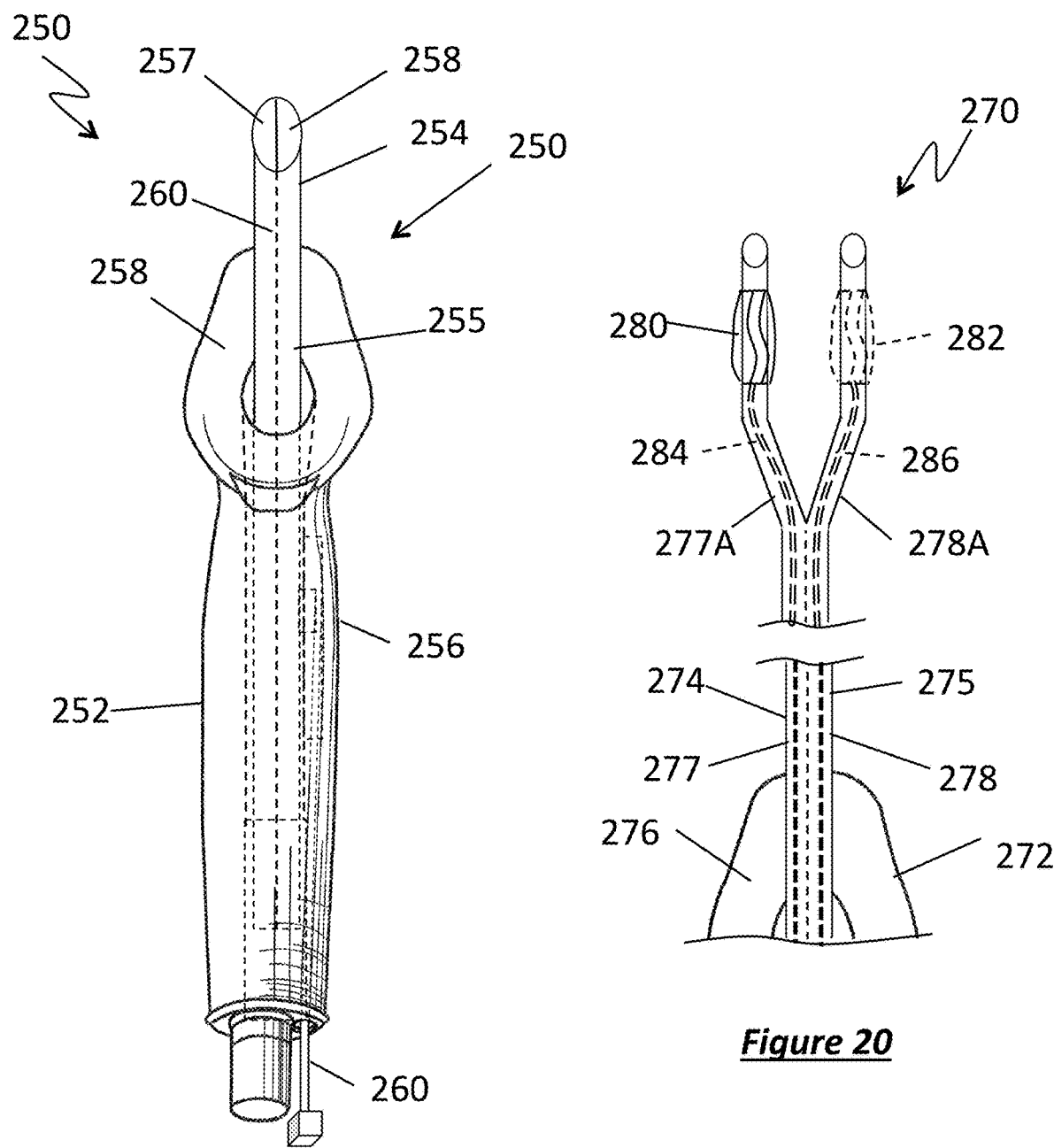
FIG. 19 is a top view of an intubation device an intubation device having an ETT component having multiple lumens according to another aspect of the invention.
FIG. 20 is a detail view of a top of an intubation device, similar to the intubation device shown in FIG. 19, having multiple lumens for, for example, bronchial isolation according to another aspect of the invention.

FIG. 19 is a top view of an intubation device 250 partially shown in cross section to illustrate details of the intubation device 250 having an ETT component 254 having multiple lumens according to another aspect of the invention. As shown in FIG. 19, intubation device 250 includes an LMA component 252 and an ETT component 254, and LMA component 252 includes a body or tube portion 256 and mask portion 258. As disclosed herein, ETT component 254 may be translatable within LMA component 252, for example, via rod 260. In the aspect shown in FIG. 19, ETT component 254 includes an elongated hollow tube 255 having multiple passages or lumens 257 and 258. In one aspect, tube 255 includes two lumens 257 and 258; however, other aspects may include 2 or more lumens, for example, 3 or more lumens, or 5 or more lumens. Though lumens 257 and 258 may be provided by individual conduits or passages, for example, conduits within or about tube 255, in one aspect, lumens 257 and 258 or more may be defined by one or more septa, for example, septum or wall 260 within tube 255.

According to aspects of the invention, the multiple lumens 257 and 258 associated with tube 255 may be in fluid communication with external fluid sources, for example, medication, handling, and/or treatment, such as, a source of fluid vacuum or fluid pressure. In one aspect, the multiple lumens 257 and 258 may access external fluid sources, treatment, or handling via one or more conduits associated with rod 260, for example, as disclosed and described with respect to FIGS. 21 and 22.

FIG. 20 is a detail view of a top of an intubation device 270, similar to intubation device 250 shown in FIG. 19, having multiple lumens for, for example, bronchial isolation according to another aspect of the invention. As shown in FIG. 20, intubation device 270 includes an LMA component 272 and an ETT component 274, and LMA component 272 includes a body or tube portion (not shown) and mask portion 276, as disclosed herein. ETT component 274 may be translatable within LMA component 272, as disclosed herein. In the aspect shown in FIG. 20, ETT component 274 includes an elongated hollow tube 275 (shown of indeterminate length to facilitate illustration of this aspect of the invention) having multiple passages or lumens 277 and 278.

Though 2 or more passages 277 and 278 may be provided, in this aspect, tube 275 may include two lumens 277 and 278, and, according to this aspect, lumens 277 and 278 may separate (for example, bifurcate) into two individual lumens 277A and 278A. As shown in FIG. 20, lumens 277A and/or 278A may have inflatable balloons or cuffs 280 and 282, respectively, which may be inflated via conduits 284 and 286, respectively. In one aspect, inflation conduits 284 and 286 may pass within or about lumen 277A and 277 and 278A and 278, respectively, to an external source of pressure, as disclosed herein, for example, to a pilot balloon (not shown).

According to aspects of the invention, the two-lumen intubation device 270 shown in FIG. 20 may be uniquely adapted for intubation with bronchial isolation. For example, in one aspect, lumen 277A having inflatable cuff 280 may be inserted into the trachea and into one of the bronchia of the lung of a patient, and then cuff 280 may be inflated to isolate the bronchus. While one bronchus may be isolated by lumen 277A and inflated cuff 280, the other bronchus may be accessed via lumen 278A to, for example, introduce or removal of fluids (including liquids and/or gases). In one aspect, both cuffs 280 and 282 may be inflated in separate bronchia to isolate both bronchia for treatment. In one aspect, lumen 277A and lumen 278A may be substantially the same length; however, in other aspects, lumens 277A and 278A may be of different lengths. In one aspect, when lumen 277A and 278A are of different lengths, different areas of the trachea and/or bronchia and/or esophagus may be isolated.

For example, in one aspect, lumen 277A having a shorter length may be positioned in the esophagus and cuff 280 may be inflated to isolate the esophagus, while lumen 278A having a longer length may be positioned in a bronchus and cuff 282 may be inflated to isolated the bronchus, for example, simultaneously, for instance, at substantially the same time. Other combinations of length of lumens and isolation of passages will be apparent to those of skill in the art.

FIG. 21 is a top view of an intubation device 300 partially shown in cross section to illustrate details of the device 300 having an ETT component 304 having a conduit according to another aspect of the invention. FIG. 22 is a detail view of the intubation device 300 shown in FIG. 21, as identified by Detail 22 shown in FIG. 21. As shown in FIGS. 21 and 22, intubation device 300 includes an LMA component 302 and an ETT component 304, and LMA component 302 includes a body or tube portion 306 and mask portion 308. As disclosed herein, ETT component 304 may be translatable within LMA component 302, for example, via rod 310.

In the aspect shown in FIGS. 21 and 22, ETT component 304 includes an elongated hollow tube 305 having one or more conduits or passages 312 and one or more open ends, holes, or orifices 314 in tube 305, for example, at the distal end of tube 305. According to aspects of the invention, the one or more orifices or holes 314 may be provided in tube 305 (for example, evenly distributed about and/or along the distal end of tube 305) and, for example, one or more of the orifices may communicate with one or more conduits 312. According to aspects of the invention, the one or more conduits or passages 312 and one or more open ends 314 may be used to introduce or extract one or more fluids to or from a trachea, a bronchus, an esophagus, or another cavity or passage into which tube 305 is placed. The one or more conduits or passages 312 may communicate with external sources, for example, sources of medication, or treatments, for example, vacuum or fluid pressure, by conventional means.

As shown most clearly in FIG. 22, in one aspect, the one or more conduits or passages 312 may communicate with external sources or treatments via one or more conduits that are associated with rod 310. In one aspect, rod 310 may be at least partially hollow and the internal opening in hollow rod 310 may be in fluid communication with conduits or passages 312.

As shown in FIG. 22, in one aspect, conduit 312 may communicate with a conduit, passage, or lumen 316 associated with rod 310, for example, mounted to rod 310, comprise a hollow rod 310, and/or extend along rod 310. In one aspect, conduit 316 may translate with rod 310, for instance, as rod 310 and rod projection 311 translate within slot or cavity 315 of tube portion 306 of LMA component 302. In another aspect, conduit 312 may translate with tube 305 and translate with rod 310. In one aspect, conduit 316 and rod 310 may exit tube portion 306 of LMA component 302 via the same opening in LMA component 302. As shown in FIG. 22, conduit 312 may communicate with conduit 316 via a transition conduit 318, for example, a conduit that conducts fluid from conduit 312 to conduit 316. In one aspect, conduits 312, 316, and 318 may be integrally formed, for example, integrally molded, when forming tube 305 and/or projection 311 and/or rod 310.

As shown in FIG. 21, conduit 316 may exit LMA component 302 and be directed and handled as needed. In one aspect, conduit 316 may be used as a pathway for introducing one or more medications, as indicated by syringe 320 shown in FIG. 20. In another aspect, conduit 316 may be used as a pathway for introducing or extracting a fluid or gas, for example, as indicated by pilot balloon 322 shown in FIG. 21.

In one aspect, the one or more conduits 316 may be in fluid communication with one or more open ends 314 of one or more conduits or lumens 312 and provide an indication of a vital sign of a patient. For example, in one aspect, pilot balloon 322 may comprise a sensor adapted to detect a condition within the patient, for example, a pressure within the trachea, bronchia, or esophagus of the patient. In another aspect, pilot balloon 322 may be respiration-indicating device, for example, a balloon or other membrane adapted to visually deflect or visually vary depending upon the respiration of the patient. In one aspect, pilot balloon 322 may be a balloon or a membrane adapted to deflect, or inflate and deflate, with the respiration of the patient to provide a visual indication of the respiration of the patient and, for example, the variation of the respiration of the patient. Other uses of one or more conduits 312, 316, and 318 and their fluid communication with one or more open ends 314 in the tube 305 will be apparent to those of skill in the art.

FIGS. 23 and 24 are schematic illustrations of cross-section views of an LMA component tube portion 330 and an ETT component tube 332 illustrating a restriction or stop to removing the ETT component tube 332 from LMA component tube portion 330 according to one aspect of the invention. LMA component tube portion 330 and an ETT component tube 332 may comprise components of any one of the intubation devices disclosed herein. Though not shown in FIGS. 23 and 24, LMA component 330 may typically have all the attributes of the LMA components disclosed herein, for example, a mask portion (not shown) and ETT component tube 332 may have all the attributes of the ETT components disclosed herein.

As disclosed herein, according to one aspect of the invention, the ETT component may be prevented from being removed from the LMA component. For example, in one aspect, one or more of ETT component tube 332 and LMA component tube 330 may include a "stop" or an "extraction stop" to physically prevent, or at least deter, removal of ETT component tube 332 from LMA component tube 330. FIGS. 23 and 24 illustrate another mechanism for preventing, or at least discouraging, removal of ETT component tube (or "ETT tube") 332 from LMA component tube (or "LMA tube") 330 according to one aspect of the invention.

As shown in FIG. 23, in this aspect, LMA tube 330 may have a varying or tapering internal dimension, for example, a varying inside diameter, that varies from a first, larger dimension at a first end 334 to a second, smaller dimension at a second end 336. Also, ETA tube 332 has a tapering external dimension, for example, a tapering outside diameter that varies from a first larger dimension at a first end 338 to a second smaller dimension at a second end 340. According to aspects of the invention, ETA tube 332 may typically be translatable within LMA tube 330, for example, by rod 342 mounted to ETT tube 332 via projection 344, as disclosed herein.

According to this aspect of the invention, removal of ETT tube 332 from LMA tube 330 is prevented, that is, prevented under expected condition of use, by interference between the external surface of ETT tube 332 with internal surface of LMA tube 330.

In the aspect of the invention shown in FIG. 23, ETT tube 332 is positioned in a first position relative to LMA tube 330, for example, where ETT tube 332 may freely translate within LMA tube 330. In FIG. 24, ETT tube 332 is positioned in a second position relative to LMA tube 330 where ETT 332 has been translated in the direction indicated by arrow 346, and the external surface of ETT tube 332 contacts the internal surface of LMA tube 330, as indicted at 348. According to aspects of the invention, this contact at 348 prevents the removal of ETT tube 322 from LMA tube 330 in the direction of arrow 346.

The dimensions of ETT tube 332 and LMA tube 330 to effect this desired aspect of the invention will be apparent to those of skill in the art in view of the typical dimensions of aspects of the invention disclosed herein.

FIG. 25 is a partial perspective view, partially in cross section, of an intubation device 400 having a rotatable endotracheal tube (ETT) component 402 mounted for translation and/or rotation within a laryngeal mask airway (LMA) component 404 according to another aspect of the invention. According to aspects of the invention, intubation device 400, ETT component 402, and LMA component 404, and any intubation device, ETT component, and LMA component disclosed herein, may have one or more of the attributes of the intubation devices, ETT components, and LMA components disclosed and described with respect to FIGS. 1 through 24. For example, intubation device 400 may have one or more of the features and functions of intubation device 10, 50, 70, 100, 130, 150, 170, 200, 250, 270, and 300 shown in FIGS. 1 through 24. Many details of intubation device 400 that are disclosed in FIGS. 1 through 24 are omitted here to avoid repetition and to facilitate disclosure of aspects of the invention.

As shown in FIG. 25, as is typical of the art, the laryngeal mask air way (LMA) component 404 is adapted to be inserted into a patient and "mask" the larynx of the patient to isolate the trachea, for example, as shown in FIG. 1. The isolation of the trachea (or "windpipe") then permits the ETT component 402 to pass into the trachea, and, for example, avoid the esophagus. The LMA component 404 may typically include a tube portion 406 and a mask portion (not shown in FIG. 25) having an opening, or internal opening, for passing ETT component 402 into, for example, the trachea.

According to aspects of the invention, the ETT component 402 of device 400 may be mounted for translation within the LMA component 404 of device 400, and the ETT component 402 of device 400 may be mounted for rotation within the LMA component 404. As disclosed and described with respect to FIGS. 1 through 24, according to aspects of the invention, ETT component 402 may be prevented, for example, substantially prevented during use, from being removed or extracted from the LMA component 404. As shown in FIG. 25, intubation device 400 may typically include one or more appropriate connectors 408 adapted to accept conventional conduits (not shown) and connector 408 may be placed in fluid communication with the internal passage of ETT component 402 and/or LMA component 404.

As disclosed herein, though many different means may be provided for translating, rotating, and substantially preventing extraction or removal of ETT component 402. In one aspect, as shown in FIG. 25, device 400 includes one or more bars or rods 410 operatively connected to ETT component 402, and providing a mechanism for rotating ETT component 402 in LMA component 404. Bar or rod 410 may include some form of handle or knob 411 adapted to facilitate manipulation, for instance, rotation and/or translation, for example, manual manipulation by an attending anesthesiologist. In one aspect, bar or rod 410 may be manipulated by an automated manipulator, for example, by an actuator or a robotic arm end, and the like. According to one aspect of the invention, one or more manipulation rods 410 may be mounted to ETT component 402 and when manipulation rod 404 is translated and/or rotated, for example, by an attending anesthesiologist, the ETT component 402 may be translated and/or rotated within LMA component 404, for example, to vary the alignment or orientation of the distal end (not shown) of ETT component 402. A typical rotation of rod 410 and ETT component 402 is illustrated schematically by double arrow 412 shown in FIG. 25. In one aspect, one or more manipulation bars or rods 410 may provide a mechanism for translating ETT component 402 in LMA component 404, for example, axially translating, for instance, translating the ETT component 402 into or extracting the distal end (not shown) of ETT component 402 from or out of the larynx and/or trachea of a patient. A typical translation of manipulation rod 410 and ETT component 402 is illustrated schematically be double arrows 414 shown in FIG. 25.

As shown in FIG. 25, the distal end of manipulation rod 410 is mounted to ETT component 402 whereby the ETT component 402 moves with the movement, rotation, and/or translation of rod 410. According to aspects of the invention, the mounting or attachment of rod 410 to ETT component 402 may be effected by any conventional means, for example, mechanical fasteners, an adhesive, or the like. In the aspect of the invention shown in FIG. 25, the distal end of rod 410 is mounted to ETT component 402 by means of a projection, a bar, a tab, a bracket, a clamp, or a plate 416 mounted to both rod 410 and to ETT component 402. In one aspect, bar 416 may be mounted to rod 410 and also mounted to ETT component 402 by any conventional means, for example, mechanical fasteners or an adhesive. In one aspect, bar 416 may be molded or formed with rod 410 or with ETT component 402, and then mounted to the corresponding component by conventional means. For example, in one aspect, rod 410 and bar 416 may be fabricated as a single integral component, for example, molded, and then bar 416 may be mounted to ETT component 402, for example with an adhesive. Other mountings of tab or bar 416 to rod 410 and to ETT component 402 will be apparent to those of skill in the art.

As shown in FIG. 25, LMA component 404 may include one or more passages or slots 418 through which rod 410 passes to engage ETT component 402. As shown in FIG. 25, slot 418 may extend an arcuate distance about the proximal end of LMA component 404, for example, subtending an angle of at least 5 degrees, but typically at least 15 degrees, or at least 45 degrees, or at least 90 degrees, or more. In one aspect, the arcuate length of slot 418 may be greater than 90 degrees, for example, at least 180 degrees, or at least 270 degrees, to provide appropriate freedom of the operator to rotate bar 410 and ETT component 402.

In one aspect, slot 418 may extend into the proximate end of LMA component 404 to provide support, for example, radial support, for rod 410 during manipulation by the user. Accordingly, in one aspect, slot 418 may have a depth or height sufficient to support rod 410 during manipulation, for example, slot 410 may have a depth at least 5 times the width or diameter of bar 410, or at least 10 times the width or diameter of bar 410. As shown in FIG. 25, slot 418 may have a width at least about as equal to the width or diameter of rod 410. For example, in one aspect, the width of slot 418 may be slightly greater than the diameter or width of rod 410. In another aspect, the width of slot 418 may be about equal to or slightly less than the diameter or width of rod 410, for example, to provide a relatively "snug" fit between rod 410 and slot 418, such that at least the user provides some resistance to the movement of rod 410 to enhance control and operation. In one aspect, detents or projections may be provided on the surface of rod 410 and/or on the internal surface of slot 418 to provide, for example, at least some tactile feedback to the user when rotating rod 410 in slot 418.

As also shown in FIG. 25, the proximal end of LMA component 404, and any LMA component disclosed herein, may typically include a conduit or tube 420 adapted to engage ETT component 402. For example, conduit 420 may be a conduit or tube in fluid communication with connector 408 and extend from connecter 408 into engagement with ETT component 402. In one aspect, as shown in FIG. 25, conduit 420 may be larger in dimension, for example, larger in internal diameter or internal width, than ETT component 402, where ETT component 402 fits into conduit 420. However, in other aspects, conduit 420 may be smaller in dimension, for example, smaller in external diameter or external width, than ETT component 402, where conduit 420 fits into ETT component 402. According to aspects of the invention, ETT component 402 typically may translate and/or rotate with respect to conduit 420, while minimizing or preventing fluid leakage from between conduit 420 and ETT component 402. One aspect of the invention for minimizing or prevention fluid leakage between conduit 420 and ETT component 402 is shown and describe with respect to FIGS. 30 and 31 below.

FIG. 26 is a partial perspective view, partially in cross section, similar to FIG. 25, where the rotatable ETT component 402 is rotated from the position shown in FIG. 25, for example, a first position, to the position shown in FIG. 26, for example, one or more second positions, according to one aspect of the invention. As shown in FIGS. 25 and 26, with the rotation of rod 410 within slot 418, for example, by manual manipulation of knob 411, the rotation of rod 410 rotates ETT component 402, including the distal end of ETT component 402 (not shown), from the first position shown in FIG. 25 to the two or more second positions shown in FIG. 26. According to aspects of the invention, it is understood that the rotation of ETT component 402 by aspects of the invention, with or without the translation of ETT component 402, may provide effective means of varying the orientation and/or position of the distal end of ETT component 402 to facilitate insertion and use of ETT component 402, for example, to avoid contact or obstruction from bodily structures, such as, the larynx.

Figures 27, 28:
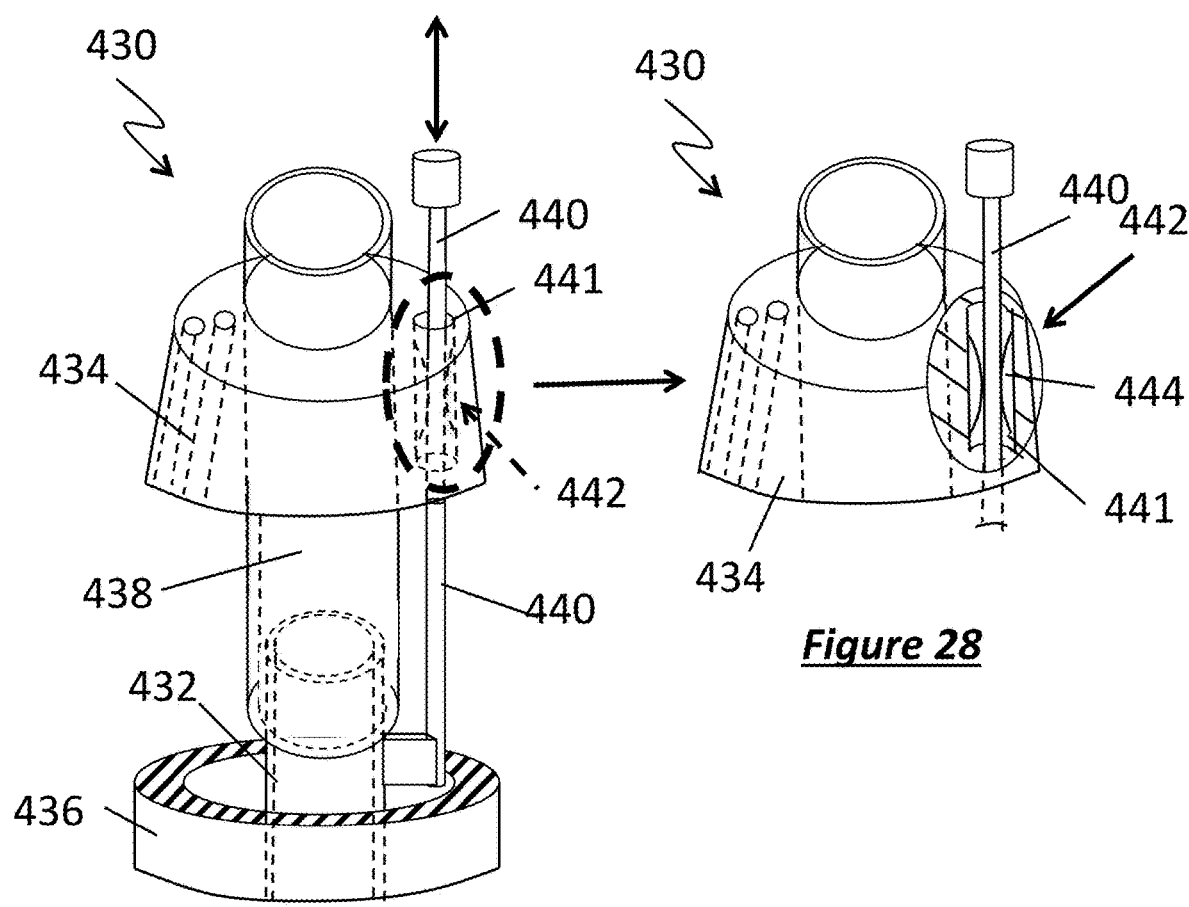
FIG. 27 is a partial perspective view, partially in cross section, of an intubation device having a translatable ETT component according to one aspect of the invention.
FIG. 28 is a partial perspective view, partially in cross section, of a portion of the intubation device shown in FIG. 27 illustrating a sealing device according to one aspect of the invention.

FIG. 27 is a partial perspective view, partially in cross section, of an intubation device 430 similar to intubation device 400 having a translatable endotracheal tube (ETT) component 432 according to one aspect of the invention. Similar to intubation device 430 shown in FIGS. 25 and 26, intubation device 430 includes an LMA component 434 having a tube portion 436 and a mask portion (not shown in FIG. 27), a conduit 438 adapted to engage (ETT) component 432, and one or more rods or bars 440 passing through one or more holes 441 of LMA component 434 and attached to ETT component 432. According to this aspect of the invention, manipulation of rod 440, for example, rotation and/or translation, effects corresponding rotation and/or translation of ETT component 432. In the aspect of the invention shown in FIG. 27, LMA component 434 includes some form of sealing device 442 adapted to minimize or prevent the leakage of fluid about manipulation rod 440.

FIG. 28 is a partial perspective view, partially in cross section, of a portion of the intubation device 430 shown in FIG. 27 illustrating one sealing device 442 according to one aspect of the invention. As shown in FIG. 28, according to one aspect of the invention, sealing device 442 comprises a barrier or structure 444 positioned in LMA component 434 to minimize or prevent leakage of fluid through the annular space between the outside dimension of rod 440 and the inside dimension of hole 441. In one aspect, barrier or structure 444 may be elastomeric, for example, a rubber ring positioned within hole 441 and allowing passage, translation, and/or rotation of rod 440. In one aspect, hole 441 may be an elongated slot, for example, as shown in slot 418 in FIG. 25, and provide a sealing function about rod 440 as rod 440 is rotated within arcuate slot 418.

FIG. 29 is a partial perspective view, partially in cross section, of another intubation device 450 having a translatable and/or rotatable endotracheal tube (ETT) component 452 with a sealing device 460 according to one aspect of the invention. Similar to intubation device 430 shown in FIGS. 25 and 26, intubation device 450 includes an LMA component 454 having a tube portion 456 and a mask portion (not shown in FIG. 29), a conduit 458 adapted to engage ETT component 452, and, though not shown in FIG. 29, intubation device 450 may include one or more rods or bars passing through LMA component 454 and attached to ETT component 452 for translation and/or rotating ETT component 452, as disclosed herein. According to this aspect of the invention, the engagement of ETT component 452 with conduit 458 includes some form of sealing device 460 adapted to minimize or prevent leakage of fluid about the engagement of ETT component 452 with conduit 458.

According to one aspect of the invention, the sealing device 460 may comprise any structure adapted to minimize or prevent fluid leakage through the mating surfaces of ETT component 452 with conduit 458. According to this aspect, the sealing device 460 may be adapted to sealing the mating surfaces of ETT component 452 with conduit 458 when ETT component 452 is smaller than and is received by a larger conduit 458, as shown in FIG. 29, or when ETT component 452 is larger than and receives a smaller conduit 458, as disclosed herein.

FIG. 30 is a cross-sectional view of the engagement of translatable and/or rotatable ETT component 452 with conduit 458 having sealing device 460 as identified by Detail 30 in FIG. 29 according to one aspect of the invention. FIG. 31 is a detailed cross-sectional view of the engagement of translatable and/or rotatable ETT component 452 with conduit 458 having sealing device 460 as identified by Detail 31 in FIG. 30.

As shown in FIGS. 30 and 31, sealing device 460 may be any barrier mounted between ETT component 452 and conduit 458 adapted to minimize or prevent fluid leakage between the mating surfaces. In one aspect, sealing device 460 may be mounted on ETT component 452 and bear against conduit 458; in another aspect, sealing device 460 may be mounted on conduit 458 and bear against ETT component 452. In one aspect, sealing device 460 may be elastomeric, for example, a "wiper"-type seal, for instance, made from one or more of the following elastomeric materials: a natural polymer, such as, polyisoprene rubber, or a synthetic polymer, such as, a neoprene, a thermoplastic elastomer, a thermoplastic rubber, and a polyvinyl chloride, or an ethylene propylene diene monomer (EPDM) rubber, and the like.

FIG. 32 is a front elevation view, partially in cross section, of another intubation device 470 having translatable and/or rotatable ETT component 472 having an indicator balloon 480 according to one aspect of the invention. In one aspect, intubation device 470 may have a manipulation bar or rod (not shown), for example, a "push rod." According to this aspect of the invention, indicator balloon 480 is in fluid communication with the distal end of ETT component 472 whereby variations in pressure at the distal end of ETT component 472, for example, due to patient respiration or breathing pattern, are reflected in variations of the shape of indicator balloon 480.

Similar to intubation devices disclosed herein, intubation device 470 includes an LMA component 474 having a tube portion 476 and a mask portion 477, a conduit 478 adapted to engage ETT component 472, and, though not shown in FIG. 32, may include one or more rods or bars passing through LMA component 474 and attached to ETT component 472 for translating and/or rotating ETT component 472, as disclosed herein. According to this aspect of the invention, the engagement of ETT component 472 with conduit 478 may include some form of sealing device (not shown) adapted to minimize or prevent leakage of fluid about the engagement of ETT component 472 with conduit 478, as disclose herein.

According to the aspect shown in FIG. 32, indicator balloon 480 may be in fluid communication with some location on or about ETT component 472 and/or in fluid communication with some location on or about LMA component 474, for example, in fluid communication with the distal end of ETT component 472, wherein variations in a condition, such as, pressure, within or about ETT component 472 and/or within or about LMA component 474, for example, at the distal end 473 of ETT component 472 and/or in the mask portion 477 of LMA component 474, are reflected in variations of the shape of indicator balloon 480. Though in one aspect, variations in a condition, for example, pressure, may be indicated by variations in the shape of balloon 480, variations in a condition may also be detected by other forms of mechanical and/or electrical transducers, such as, an appropriate sensor. As shown in FIG. 32, indicator balloon 480 may be in fluid communication with intubation device 470 and/or LMA component 474 via one or more conduits or hoses 482. According to aspects of the invention, conduit 482 is in fluid commutation with passages or conduits within intubation device 470, for example, with conduit 484 shown in FIG. 32 having an open end 486 in the distal end 473 of ETT component 472.

FIG. 33 is a detailed cross-sectional view of a portion of the intubation device 470 shown in FIG. 32 as identified by Detail 33 in FIG. 32. As shown in FIG. 33, conduit 482 from balloon 480, or a conduit or passage within intubation device 470 in fluid communication with conduit 482, is in fluid communication with conduit 484 in ETT component 472. According to aspects of the invention, conduit 482 may be directed directly to conduit 484, or conduit 482 may be directed to conduit 484 via one or more conduits or passages 485 in intubation device 470, for example, one or more conduits 485 within ETT component 472 and/or within LMA component 474.

FIG. 34 is a front elevation view, partially in cross section, of another intubation device 500 having translatable and/or rotatable ETT component 502 having one or more inflatable cuffs 503 and/or 505 (shown in phantom), one or more manipulation bars or rods 510, and one or more cuff inflation balloons 520 according to one aspect of the invention. According to this aspect of the invention, intubation device 500 may have one or more inflation cuffs 503 adapted to inflate and assist the operator in positioning and/or orienting the distal end of the ETT component 502 within the patient and/or to at least partially seal a cavity into which ETT component 502 is inserted. Intubation device 500 may also have one or more inflation cuffs 505 adapted to inflate and assist the operator in positioning and/or orienting the ETT component 502 within the patient, and/or adapted to seal or restrict fluid flow through the annular cavity between the outside of the ETT component 520 and the inside of LMA component 504.

Similar to intubation devices disclosed herein, intubation device 500 includes an LMA component 504 having a tube portion 506 and a mask portion 507, and a conduit 508 adapted to engage ETT component 502. The one or more bars or rods 510 may pass through LMA component 504 and attach to ETT component 502 for translating and/or rotating ETT component 502, as disclosed herein. According to this aspect of the invention, the engagement of ETT component 502 with conduit 508 may include some form of sealing device (not shown) adapted to minimize or prevent leakage of fluid about the engagement of ETT component 502 with conduit 508, as disclosed herein.

As shown in FIG. 34, the one or more manipulation rods 510 may engage LMA component 504 via one or more conduits or sleeves 512. According to one aspect, at least one of rod 510 and/or sleeve 512 may be flexible; however, in another aspect, both rod 510 and sleeve 512 may be flexible, that is, made from a bendable or pliable material, such as, a rubber or a plastic. According to one aspect, the flexibility of rod 510 and/or sleeve 512 can facilitate the manipulation and accessibility of rod 510 by the operator.

As also shown in FIG. 34, the one or more cuff inflation balloons 520 may be in fluid communication with LMA component 504 via one or more conduits or tubes 522 which may be in fluid communication with the one or more inflatable cuffs 503 and/or 505 on ETT component 502 via passages or conduits within intubation device 500, for example, via conduit 514 which communicates with cuff 503 in the distal end of ETT component 502 and/or with cuff 505 positioned along ETT component 502 at a location within LMA component 504. In one aspect, sleeve 512 of rod 510 and conduit 522 of cuff inflation balloon 520 may engage LMA component 504 via a common opening or via separate openings. In one aspect, sleeve 512 and conduit 522 be mounted or attached to each other.

FIG. 35 is a detailed cross-sectional view of a portion of the intubation device 500 shown in FIG. 34 as identified by Detail 35 in FIG. 34. As shown in FIG. 35, the one or more manipulation rods 510 may access LMA component 504 via sleeve 512, or one or more sleeves or conduits attached to sleeve 512. As also shown in FIG. 35, in a fashion similar to the access of conduit 482 shown in FIGS. 32 and 33, conduit 522 from cuff inflation balloon 520, or a conduit or passage within intubation device 500 in fluid communication with conduit 522, is in fluid communication with conduit 514 in or on ETT component 502. According to aspects of the invention, conduit 522 may be directed directly to conduit 514, or conduit 522 may be directed to conduit 514 via one or more conduits or passages 516 in intubation device 500, for example, one or more conduits 516 within ETT component 502 and/or within LMA component 504.

In one aspect, manipulation rod 510 may be attached to ETT component 502 as disclosed herein, for example, as shown in FIGS. 25 and 26. For example, manipulation rod 510 may be attached to ETT component 502 via projection, bar, tab, or plate 518 mounted to both rod 510 and ETT component 502, as disclosed herein.

Figure 36:
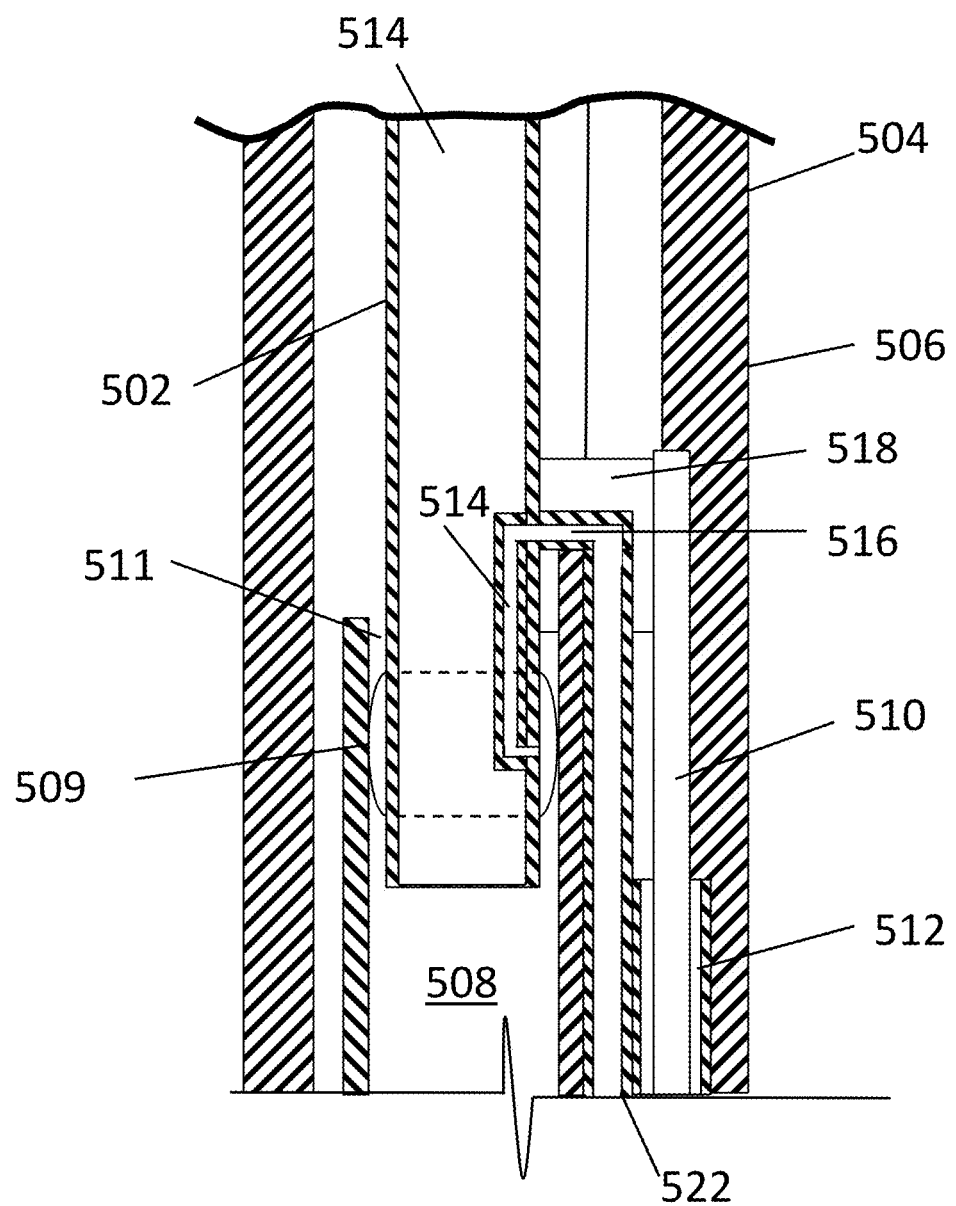
FIG. 36 is another detailed cross-sectional view, similar to FIG. 35, of a portion of the intubation device shown in FIG. 34 as identified by Detail 35 in FIG. 34 according to another aspect of the invention.

FIG. 36 is another detailed cross-sectional view, similar to FIG. 35, of a portion of the intubation device 500 shown in FIG. 34 as identified by Detail 35 in FIG. 34 according to another aspect of the invention. As shown in FIG. 36, the one or more manipulation rods 510 may access LMA component 504 via sleeve 512, or one or more sleeves or conduits attached to sleeve 512. As also shown in FIG. 36, in a fashion similar to the access of conduit 482 shown in FIGS. 32 and 33 and similar to the access of conduit 516 shown in FIG. 36, conduit 522 from cuff inflation balloon 520, or a conduit or passage within intubation device 500 in fluid communication with conduit 522, is in fluid communication with conduit 514 in or on ETT component 502 and inflation cuff 509. According to this aspect of the invention, the inflation of inflation cuff 509 seals or restricts fluid flow through the annular cavity between the outside of the ETT component 502 and the inside of LMA conduit 508.

According to aspects of the invention, conduit 522 may be directed directly to conduit 514 and inflation cuff 509, or conduit 522 may be directed to conduit 514 via one or more conduits or passages 516 in intubation device 500, for example, one or more conduits 516 within ETT component 502 and/or within LMA component 504.

In one aspect, the structure illustrated by inflation cuff 509 in FIG. 36 may comprise any restriction or sealing element adapted to seal or restrict fluid flow through the annular cavity 511 between the outside of the ETT component 502 and the inside of LMA conduit 508. For example, in one aspect, the structure identified as inflation cuff 509 may not be an inflation cuff but may be a flexible sealing element, for example, similar or identical to sealing device 460 shown in FIGS. 30 and 31 and/or an O-ring type seal, as known in the art. In another aspect, the structure identified, as inflation cuff 509 may be a flexible fluid-filled device adapted to seal or restrict fluid flow through the annular cavity 511, for example, a viscous fluid or a gel-like fluid adapted to provide at least some restriction to the flow of fluid through the annular cavity 511.

In one aspect, manipulation rod 510 may be attached to ETT component 502 as disclosed herein, for example, as shown in FIGS. 25 and 26. For example, manipulation rod 510 may be attached to ETT component 502 via projection, bar, tab, or plate 518 mounted to both rod 510 and ETT component 502, as disclosed herein.

Figure 37:
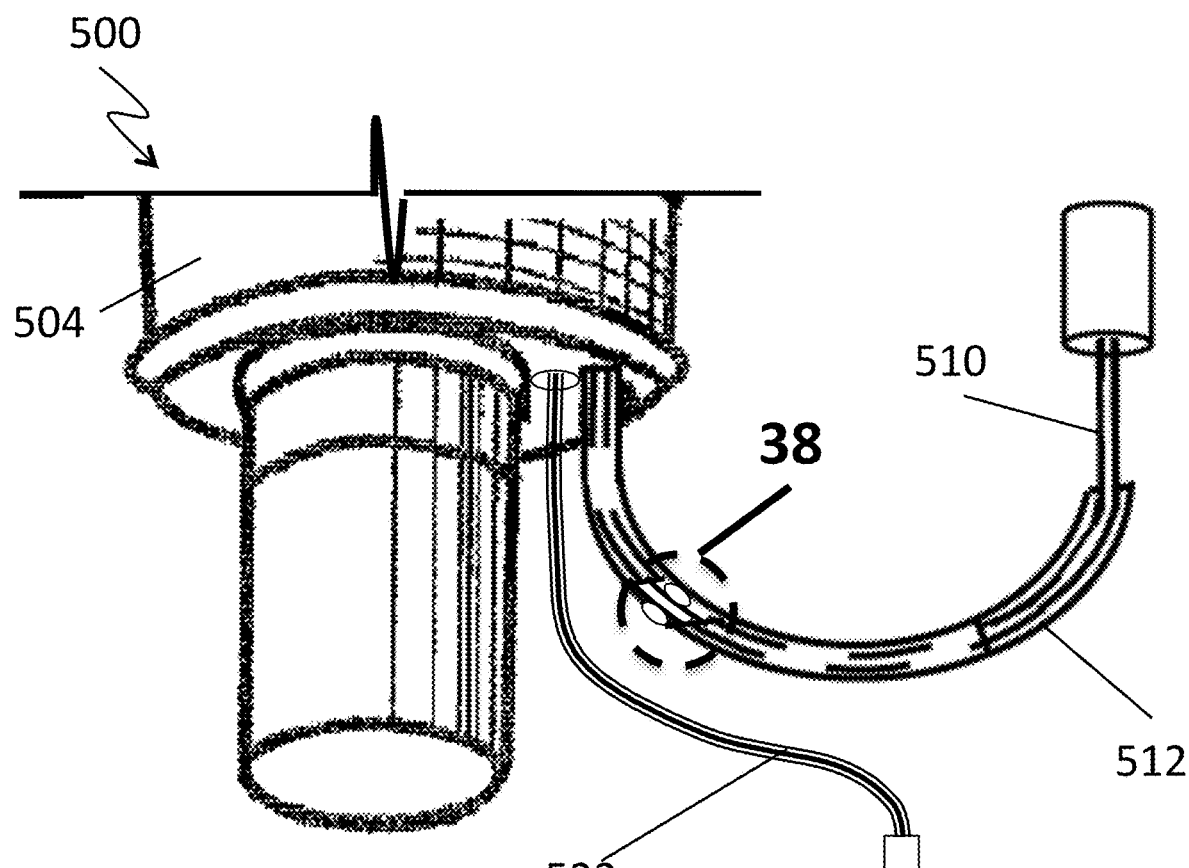
FIG. 37 is a perspective view of an end portion of the intubation device shown in FIG. 34 showing the engagement of the manipulation rod and the cuff inflation balloon with the intubation device according to one aspect of the invention.

FIG. 37 is a perspective view of an end portion of the intubation device 500 shown in FIG. 34 showing the engagement of the manipulation rod 510 and the cuff inflation balloon 520 with the intubation device 500 according to one aspect of the invention. As shown in FIG. 37, the one or more manipulation rods 510 may access LMA component 504 via manipulation rod sleeve, or "guide sleeve," 512 and conduit 522 from cuff inflation balloon 520 is in fluid communication with conduit 514 (not shown).

Figure 38:
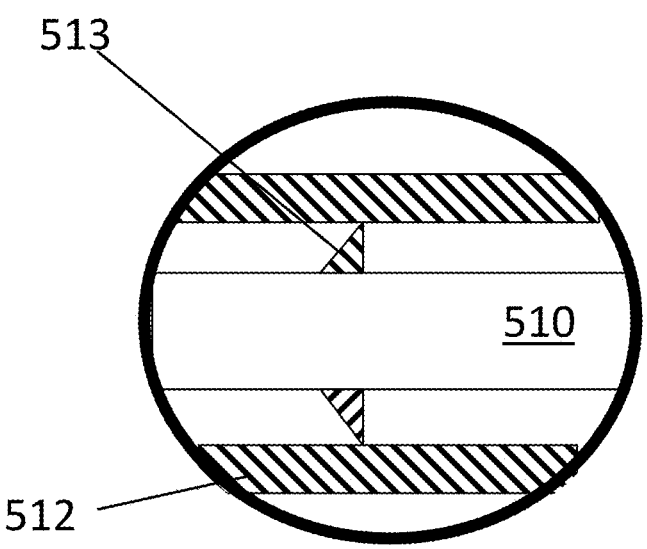
FIG. 38 is a detailed cross-sectional view of a portion of the manipulation rod sleeve having a sealing device shown in FIG. 37 as identified by Detail 38 in FIG. 12.

FIG. 38 is a detailed cross-sectional view of a portion of the manipulation rod sleeve, or "guide sleeve," 512 having a sealing device 513 shown in FIG. 37 as identified by Detail 38 in FIG. 37. As shown in FIG. 38, in one aspect, sleeve 512 and/or rod 510 may include some form of sealing device 513 adapted to minimize or prevent the passage of fluids between the inside diameter of sleeve 512 and the outside diameter of rod 510.

As shown in FIG. 38, sealing device 513 may be any barrier mounted between rod 510 and sleeve 512 adapted to minimize or prevent fluid leakage there between. In one aspect, sealing device 513 may be mounted on rod 510 and bear against sleeve 512; in another aspect, sealing device 513 may be mounted on sleeve 512 and bear against rod 512. In one aspect, sealing device 513 may be elastomeric, for example, a "wiper"-type seal, for instance, made from one or more of the following elastomeric materials: a natural polymer, such as, polyisoprene rubber, or a synthetic polymer, such as, a neoprene, a thermoplastic elastomer, a thermoplastic rubber, and a polyvinyl chloride, or an ethylene propylene diene monomer (EPDM) rubber, and the like.

Figure 39:
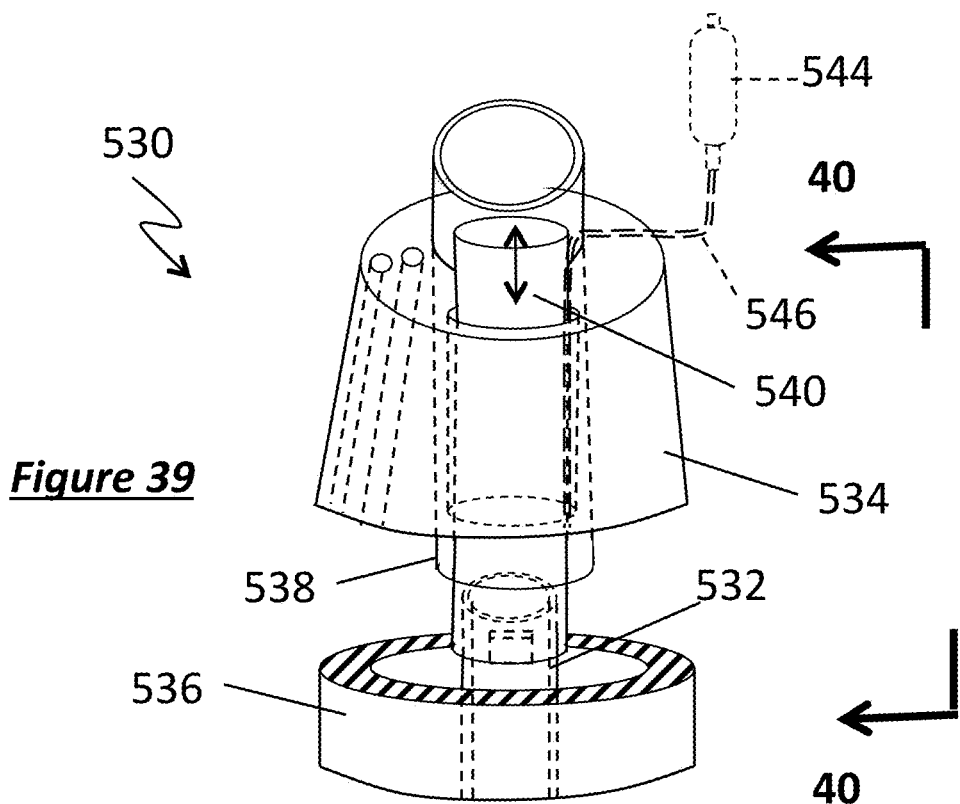
FIG. 39 is a partial perspective view, partially in cross section, of another intubation device having a translatable and/or rotatable ETT component and having a manipulation rod according to one aspect of the invention.
Figure 40:
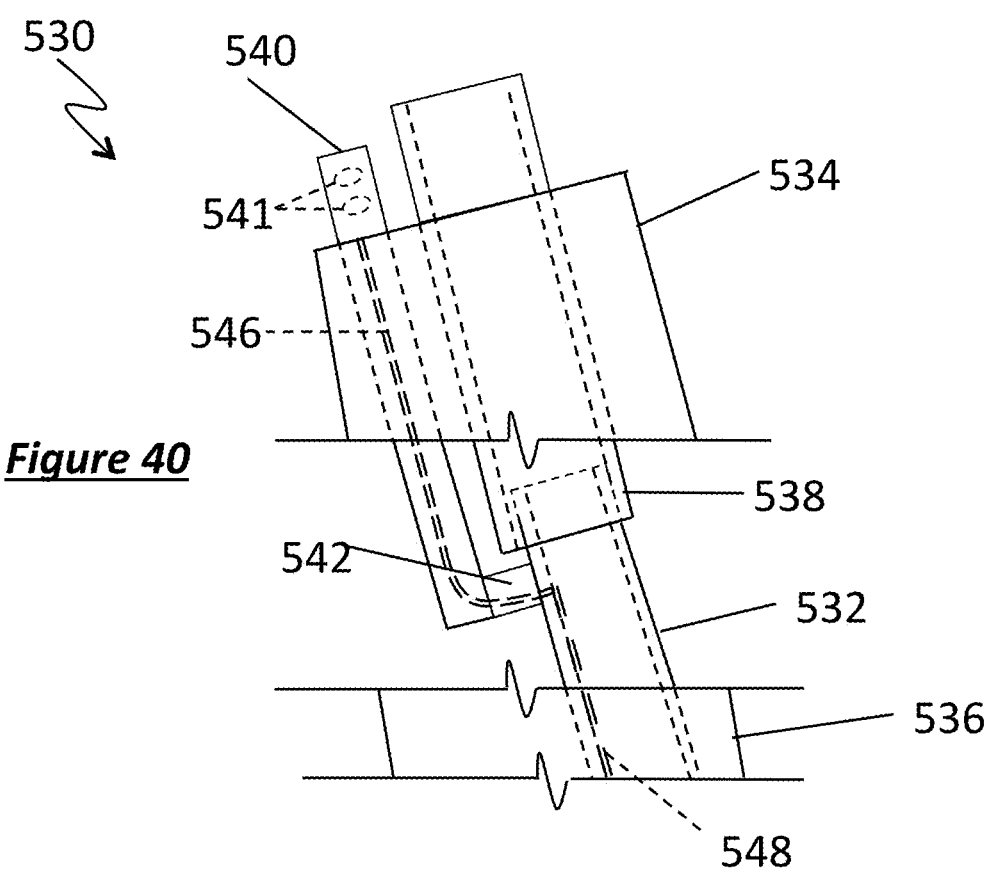
FIG. 40 is a side elevation view of the partial perspective view of the intubation device shown in FIG. 39 as viewed along view lines 40-40 shown in FIG. 39.

FIG. 39 is a partial perspective view, partially in cross section, of another intubation device 530 having a translatable and/or rotatable ETT component 532 and having a manipulation rod 540 according to one aspect of the invention. FIG. 40 is a side elevation view of the partial perspective view of the intubation device 530 shown in FIG. 39 as viewed along view lines 40-40 shown in FIG. 39.

As shown in FIGS. 39 and 40, as in similar aspects disclosed herein, intubation device 530 includes an LMA component 534 having a tube portion 536 and a mask portion (not shown), and a conduit 538 adapted to engage ETT component 532. In the aspect shown in FIGS. 39 and 40, instead of one or more relatively thin bars or rods adapted to may pass through LMA component 534 and attach to ETT component 532 for translating and/or rotating ETT component 532, intubation device 530 includes one or more larger rods or "buttons" 540 adapted to pass through LMA component 534 and attach to ETT component 532 for translating and/or rotating ETT component 532. According to this aspect of the invention, the relatively larger rods or "buttons" 540 may facilitate access and manipulation, for example, "push button" manipulation, for example, translation, of ETT component 532 within LMA component 534. Though not shown FIGS. 39 and 40, the larger rod or "button" 540 may include some form of sealing device (not shown) adapted to minimize or prevent leakage of fluid about the engagement of rod 540 within LMA component 534, as disclose herein, for example, in a fashion similar to the sealing device shown in FIGS. 30 and 31. In one aspect, rod 540 may be elliptical in cross section, as shown in FIGS. 39 and 40; however, it is envisioned that rod 540 may comprise any cylindrical shape, including elliptical cylindrical, circular cylindrical, and polygonal cylindrical, among other cylindrical shapes.

As shown must clearly in FIG. 40, rod 540 may be an elongated rod and be mounted for deflection within LMA component 534 and engage ETT component 532. Consistent with other aspects of the invention disclosed herein, deflection of rod 540, for example, deflection into LMA component 534 or extraction from LMA component 534, correspondingly deflects ETT component 532 wherein the distal end (not shown) of ETT component 532 can be inserted into or extracted from the throat of the patient. In one aspect, one or more structures 541 (shown in phantom), for example projections, recesses, or indentations, may be provided on rod 540 to facilitate handling and/or manipulation of rod 540, for example, to facilitate extraction of rod 540 from LMA component 534.

According to aspects of the invention, the mounting or attachment of rod 540 to ETT component 532 may be effected by any conventional means, for example, mechanical fasteners or an adhesive, and the like. In the aspect of the invention shown in FIGS. 39 and 40, the distal end of rod 540 may be mounted to ETT component 532 by means of a projection, a bar, a tab, a bracket, a clamp, or a plate 542 mounted to both rod 540 and ETT component 532. In one aspect, bar 542 may be mounted to rod 540 and to ETT component 532 by any conventional means, for example, mechanical fasteners or an adhesive. In one aspect, bar 542 may be molded or formed with rod 540 or with ETT component 532, and then mounted to the corresponding component by conventional means. For example, in one aspect, rod 540 and bar 542 may be fabricated as a single integral component, for example, molded, and then bar 542 may be mounted to ETT component 532, for example, with an adhesive. Other mountings of bar 542 to rod 540 and to ETT component 432 will be apparent to those of skill in the art.

In one aspect, as shown in FIGS. 39 and 40, intubation device 530 may include one or more inflation cuffs and one or more corresponding cuff inflation balloons and/or one or more indicator balloons, as indicated by phantom by balloon 544 (shown in phantom) in FIG. 39. Balloon 544 may be similar in design and function to cuff inflation balloon 520 shown in FIG. 34. Balloon 544 may be similar in design and function to indicator balloon 480 shown in FIG. 32. Whether balloon 544 is a cuff inflation balloon or a indicator balloon, balloon 544 may typically be in fluid communication with LMA component 434 via conduit or conduit 546 (shown in phantom), and, depending upon the function of balloon 544, conduit 546 may be in fluid communication with a passage or conduit 548 of ETT component 532 or a passage in LMA component 534. Passage or conduit 548 of ETT component 532 may extend to an inflatable cuff (not shown) on ETT component 531 and/or to an open end, for example, at the distal end (not shown) of ETT component, depending upon the function of balloon 540. As shown most clearly in FIG. 40, passage or conduit 546 may communicate with passage or conduit 548 across plate 542 as disclosed herein.

Figure 41:
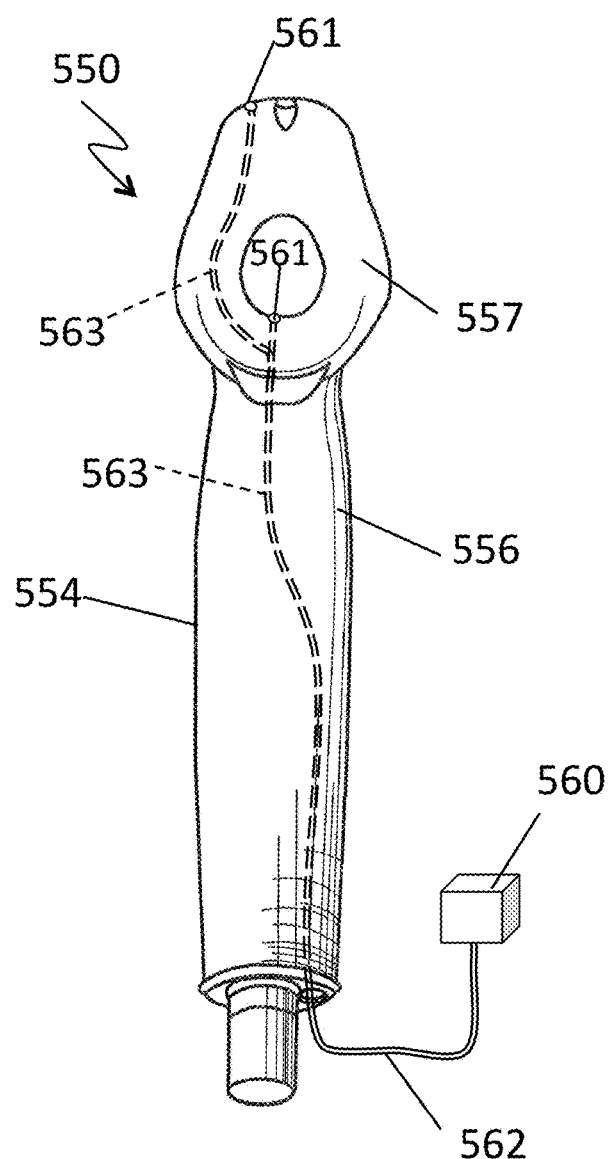
FIG. 41 is a front view of an intubation device having an image-capturing device and an image-capturing device access passage according to an aspect of the invention.

FIG. 41 is a front view of an intubation device 550 having an image-capturing device 560 and an image-capturing device access conduit or tube 562 according to an aspect of the invention. As in similar aspects disclosed herein, intubation device 550 includes an ETT component (not shown), an LMA component 554 having a tube portion 556 and a mask portion 557, and a conduit (not shown) adapted to engage the ETT component, as disclosed herein.

As shown in FIG. 41, intubation device 550 may typically include one or more image capturing apertures 561, one or more wires or cables 562, for example, a fiber optic cable, adapted to transmit signals corresponding to the images captured by the aperture 561 to image capturing device 560, and one or more passages or conduits 563 adapted to receive wire or cable 562. The images captured may be still or moving images. Image capturing device 560 may be any device adapted to receive and store, locally or remotely, signals associated with the images captured by cable 561. Image capturing aperture 561, cables 562, and image capturing device 560 may be adapted to capture images in the visual spectrum, or in any range of the electromagnetic spectrum desired, including x-ray images, infrared images, and microwave images, and the like.

According to aspects of the invention shown in FIG. 41, intubation device 550 may include one or more image capturing apertures 561 and one or more passages 563 positioned anywhere images are desired to be captured. Image capturing apertures 561 and passages or conduits 563 may be located in the ETT component (not shown) and/or may be located within LMA component 554, as desired.

According to aspects of the invention one or more image-capturing apertures 561 may be positioned in the distal end of the LMA component 544 and/or positioned in the distal end of an ETT component (not shown). The images captured may be transmitted wirelessly or by wire to image capturing device 560. The images captured may be displayed locally for immediate feedback on treatment or operation of aspects of the invention, or stored locally or remotely for future review.

Figure 42:
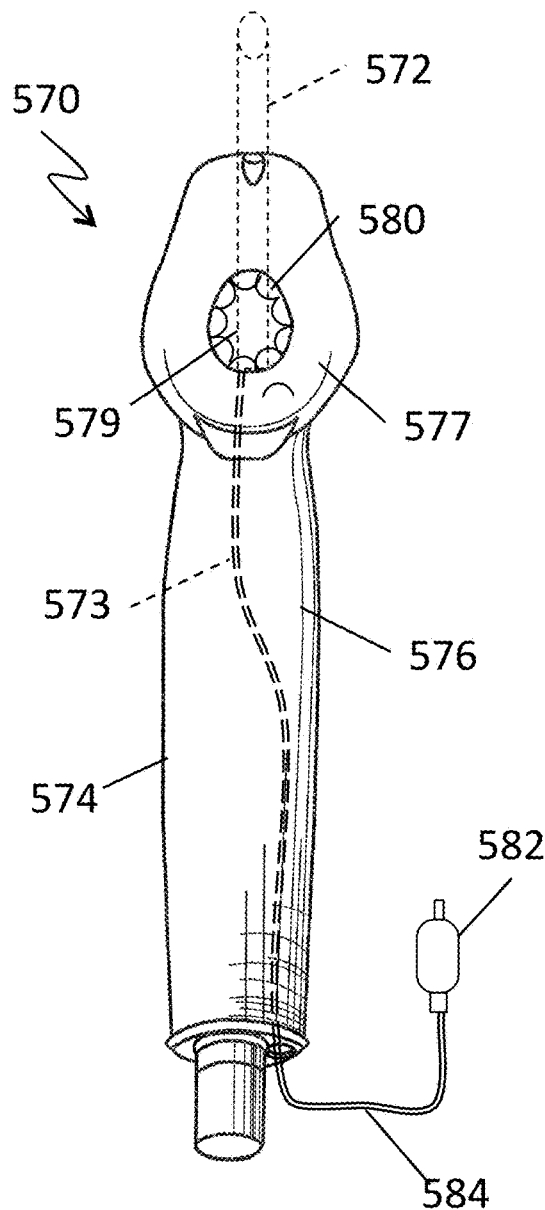
FIG. 42 is a front view of an intubation device having an inflatable ETT balloon cuff and a cuff inflation balloon according to an aspect of the invention.

FIG. 42 is a front view of an intubation device 570 having an inflatable endotracheal tube (ETT) balloon cuff 580 and a cuff inflation balloon 582 according to an aspect of the invention. As in similar aspects disclosed herein, intubation device 570 includes an ETT component 572 (shown in phantom), an LMA component 574 having a tube portion 576 and a mask portion 577 having a mask portion opening 579, and a conduit (not shown) adapted to engage the ETT component 572, as disclosed herein. According to this aspect of the invention, inflatable balloon cuff 580 positioned within or about mask portion opening 579 provides a means for manipulating the passage of the ETT component 572 through or about inflatable balloon cuff 580. For example, in one aspect, inflation of inflatable balloon cuff 580 or inflation of a portion of inflatable balloon cuff 580 may assist the anesthesiologist in properly and/or accurately positioning the distal end of ETT component 572 within the patient.

As shown in FIG. 42, intubation device 570 may typically include one or more inflation balloons 582 adapted to inflate one or more balloon cuffs 580 and/or one or more portions of balloon cuff 580 to assist in positioning the ETT component 572. The one or more inflation balloons 582 may each typically be in fluid communication with balloon cuff 580 or a portion of balloon cuff 580 via one or more tubes or conduits 584. Conduit 584 may communicate directly with balloon cuff 580 or with a portion of balloon cuff 580, or communicate with balloon cuff 580 or with a portion of balloon cuff 580 via one or more conduits or passages 573 within intubation device 570, for example, within LMA component 574. For example, in one aspect, two or more cuff inflation balloons 582 may be in fluid communication with two or more balloon cuff 580 or two or more portions of balloon cuff 580 to allow the user to vary the inflation of the two or more balloon cuff 580 or the two or more portions of balloon cuff 580 to vary the position and/or orientation of ETT component 572 within opening 579 and correspondingly within the patient.

Figure 43:
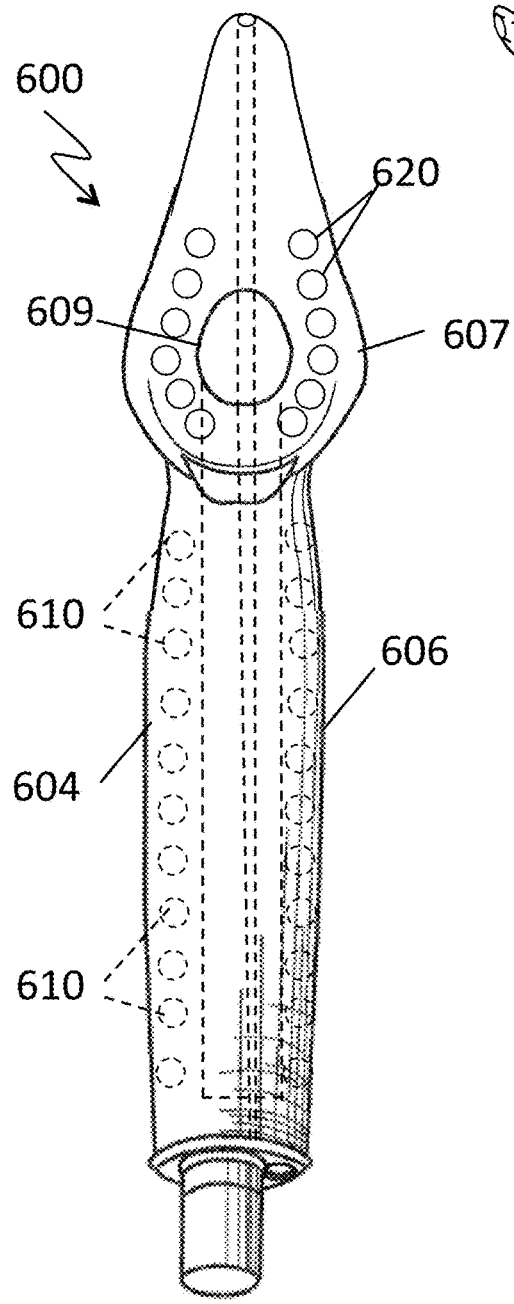
FIG. 43 is a front view of an intubation device having body cavities and surface protrusions according to an aspect of the invention.
Figure 44:
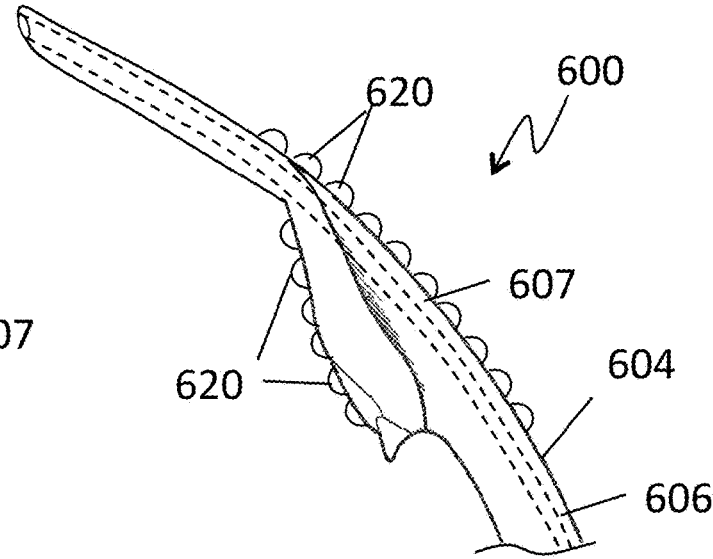
FIG. 44 is a partial side elevation view of the intubation device shown in FIG. 43.

FIG. 43 is a front view of an intubation device 600 having body cavities 610 and surface protrusions 620 according to an aspect of the invention. According to this aspect of the invention, body cavities 610 may reduce the weight of intubation device 600 and/or the amount of material of intubation device 600 compared to an intubation device not having body cavities 610. In addition, surface protrusions or surface "corrugations" 620 may provide a means for stimulating or "massaging" body surfaces to facilitate insertion and removal of intubation device 600. FIG. 44 is a partial side elevation view of the intubation device 600 shown in FIG. 43, and FIG. 45 is a partial rear elevation view of the intubation device 600 shown in FIGS. 43 and 44.

Figure 45:
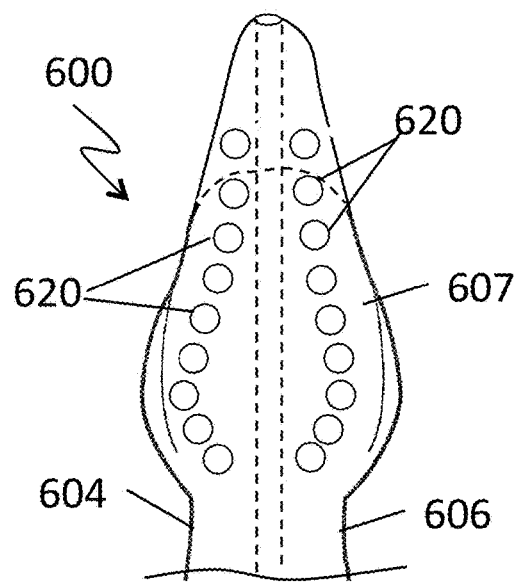
FIG. 45 is a partial rear elevation view of the intubation device shown in FIGS. 43 and 44.

As shown in FIGS. 43-45, intubation device 600 may include an ETT component (not shown), an LMA component 604 having a tube portion 606 and a mask portion 607 having a mask portion opening 609, and a conduit (not shown) adapted to engage the ETT component, as disclosed herein. According to this aspect of the invention, LMA component 604 includes a plurality of internal cavities or voids 610 that may be located within LMA component 604 to limit the amount of material, for example, the amount of silicone rubber, required to fabricate LMA component 604, and, possibly, reduce the weight of LMA component 604, while not negatively affecting the desired structural strength and/or stiffness of LMA component 604.

Internal cavities or voids 610 may be located within tube portion 606 and/or within mask portion 607, and may vary in shape and size to provide the desired weight reduction and/or material reduction. As shown in FIG. 43, internal cavities or voids 610 may be spherical in shape, but any three dimension shape that is conducive to the size and strength of LMA component 604 is envisioned, including elongated rounded voids, among others.

As shown in FIGS. 43-45, intubation device 600 may include a plurality of projections 620 on the surface of intubation device 600, for example, on the surface of the body portion 606 and/or on the surface of the mask portion 607. According to aspects of the invention, projections 620 may be hollow or non-hollow projections, for example, with or without an internal void. As shown in FIGS. 43-45, projections 620 may be round or hemispherical in shape, though it is envisioned that aspects of the invention may include projections 620 that are polygonal in shape, or example, geodesic in shape, with rounded corners, and provide the desired function.

Projections 620 may project from the surface of LMA component 604 from 0.1 millimeters [mm] to 25 mm, but may typically project from 1 mm to 5 mm from the surface of LMA component 604. The dimensions of projections 620 may vary depending upon the size and function of projections 620. For example, the width, diameter, or sector length of projections 620 may vary from 0.1 mm to 25 mm, but may typically having a width dimension from 1 mm to 5 mm.

Figures 46, 47:
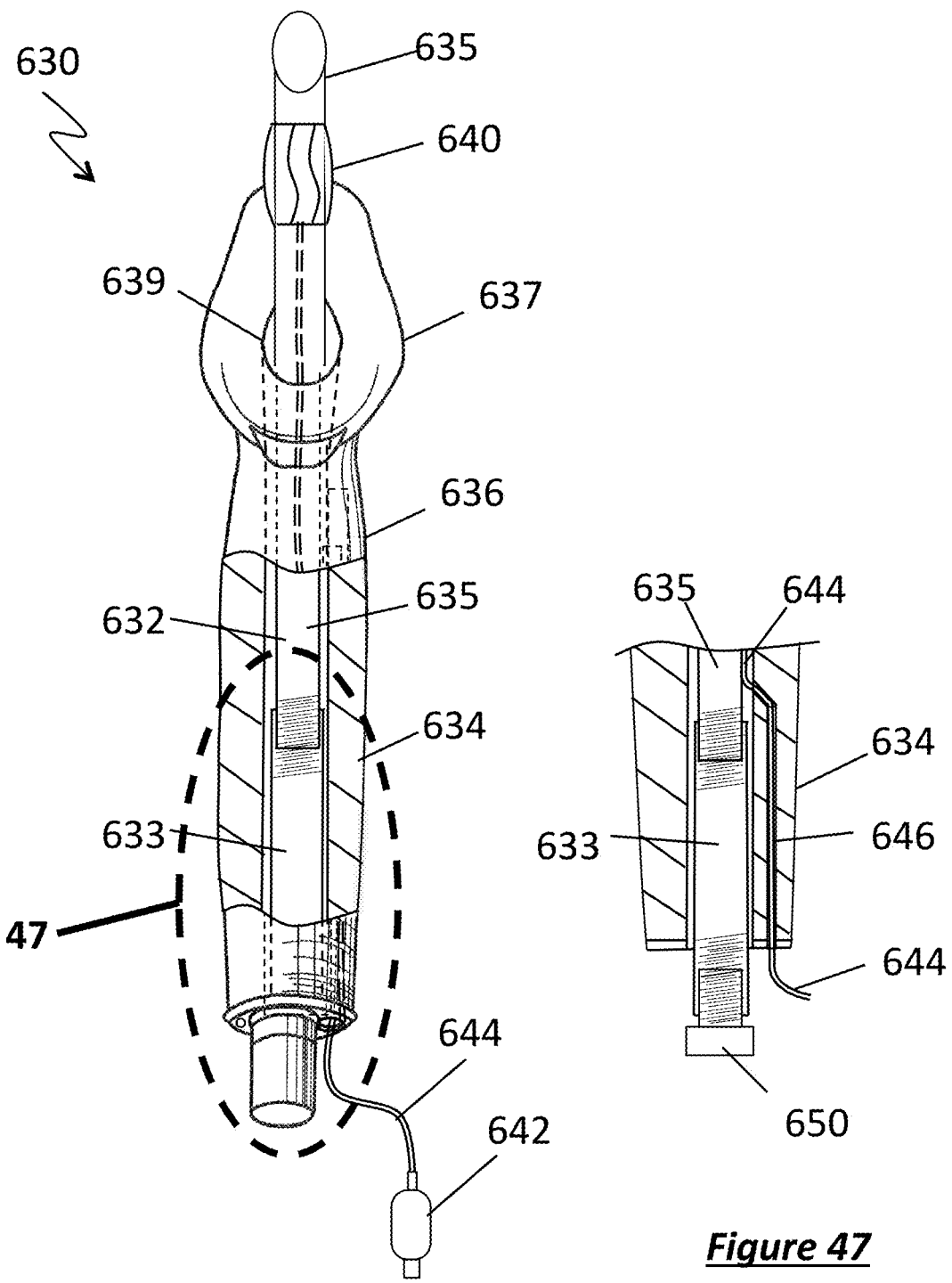
FIG. 46 is a front view of an intubation device having a multipart endotracheal tube (ETT) component, a balloon cuff, and balloon cuff inflation balloon according to an aspect of the invention.
FIG. 47 is a detailed cross-sectional view of the intubation device shown in FIG. 46, as identified by Detail 47 in FIG. 46, according to one aspect of the invention.

FIG. 46 is a front view of an intubation device 630 having a multipart endotracheal tube (ETT) component 632, a balloon cuff 640, and balloon cuff inflation balloon 642 according to an aspect of the invention. According to this aspect of the invention, the ETT component 632 may comprise multiple interconnected components, 633, 635, for example, 2 or more interconnected components, that can be engaged and disengaged as needed to facilitate assembly, insertion, and/or adjustment of ETT component 632.

Similar to other aspects of the invention disclosed herein, intubation device 630 includes an ETT component 632, an LMA component 634 having a tube portion 636 and a mask portion 637 having a mask portion opening 639, and a conduit (not shown) adapted to engage the ETT component 632, as disclosed herein. Balloon cuff inflation balloon 642 is operatively connected, for example, in fluid communication with, inflation cuff 640 via one or more tubes, conduits, or passages 644. According to this aspect of the invention, inflatable balloon cuff 640 positioned on ETT subcomponent 635 provides a means for manipulating the positioning of the distal end of ETT subcomponent 635. For example, in one aspect, at least partial inflation of inflatable balloon cuff 640 or inflation of a portion of inflatable balloon cuff 640 may assist the anesthesiologist in properly and accurately positioning the distal end of ETT subcomponent 635 within the patient.

According to this aspect of the invention, the subcomponents 633, 635 of ETT component 632 may be adapted to engage and disengage by any conventional means, for example, via mechanical fasteners and/or interference fit, among other means. In the aspect shown in FIG. 46, subcomponents 633 and 635 may engage and/or disengage by threaded connections, for example, internal threaded connections and/or external threaded connections. For example, in the aspect shown in FIG. 46, subcomponent 633 may be larger in size, for instance, larger in diameter, than subcomponent 635 wherein a distal end of subcomponent 633 is internally threaded and the proximal end of subcomponent 635 is correspondingly externally threaded. The pitch and size of the thread may vary while providing the desired engagement and/or disengagement of subcomponents 633, 635, and any other subcomponents present.

The size of subcomponents 633 and 635 may vary depending upon the size and application of aspects of the invention. In one aspect, the diameter, for example, outer diameter of subcomponents 633, 635 may range from 1 to 100 mm, but typically, may range from 5 to 15 mm, for example, about 9-10 mm in diameter.

FIG. 47 is a detailed cross-sectional view of the intubation device 630 shown in FIG. 46 as identified by Detail 47 in FIG. 46, according to one aspect of the invention. In the aspect of the invention shown in FIG. 47, ETT subcomponents 633 and 635 are threadably engaged within LMA component 634 in a fashion similar to that shown in FIG. 46. In the aspect of the invention shown in FIG. 47, ETT subcomponent 635 also engages coupling 650, for example, a conventional 15 mm connector. As is conventional, coupling 650 can be provided to operatively connect ETT subcomponent 635 to a source of treatment fluid (not shown), for example, an oxygen-containing gas.

As also shown FIG. 47, tube or conduit 644 from cuff inflation balloon 642 may typically be introduced to intubation device 630 and be operatively connected to inflation cuff 640 via one or more passages or channels 646 in LMA component 634. As shown in FIG. 47, passage 646 may extend within LMA component 634 and exit LMA component 643 to allow tube or conduit 644 to access inflation cuff 640, for example, by attaching to and/or extending along subcomponent 635 to inflation cuff 640.

FIG. 48 is a front view of an intubation device 660 having a multipart endotracheal tube (ETT) component 662, a balloon cuff 670, and a balloon cuff inflation balloon 672 according to another aspect of the invention. According to this aspect of the invention, the ETT component 662 may comprise a multiple interconnected components, 663, 665, for example, 2 or more interconnected components, that can be engaged and disengaged as needed to facilitate assembly, insertion, and/or adjustment of ETT component 662.

Similar to other aspects of the invention disclosed herein, intubation device 660 includes an ETT component 662, an LMA component 664 having a tube portion 666 and a mask portion 667 having a mask portion opening 669, and a conduit (not shown) adapted to engage the ETT component 662, as disclosed herein. Balloon cuff inflation balloon 672 is operatively connected, for example, in fluid communication with, inflation cuff 670 via one or more tubes, conduits, or passages 674. According to this aspect of the invention, inflatable balloon cuff 670 positioned on ETT subcomponent 635 provides a means for manipulating the position of the distal end of ETT subcomponent 665 and/or to at least partially seal a cavity into which ETT component 662 is inserted. For example, in one aspect, at least partial inflation of inflatable balloon cuff 670 or inflation of a portion of inflatable balloon cuff 670 may assist the anesthesiologist in properly and accurately positioning the distal end of ETT subcomponent 665 within the patient.

According to this aspect of the invention, the subcomponents 663, 665 of ETT component 652 may be adapted to engage and disengage in a fashion similar to that shown in FIG. 46. However, in the aspect of the invention shown in FIG. 48, subcomponents 663, 665 engage and/or disengage via an interlocking mechanism 676.

FIG. 49 is a detailed cross-sectional view of the intubation device 660 shown in FIG. 48 showing the engagement of portions of the multipart ETT component 662 via interlocking mechanism 676 as identified by Detail 49 shown in FIG. 48.

FIGS. 50 through 58 are views of engineering drawings of one intubation device 700 having one or more of the aspects disclosed and described with respect to FIGS. 1-49, according to aspects of the invention.

Figure 50:
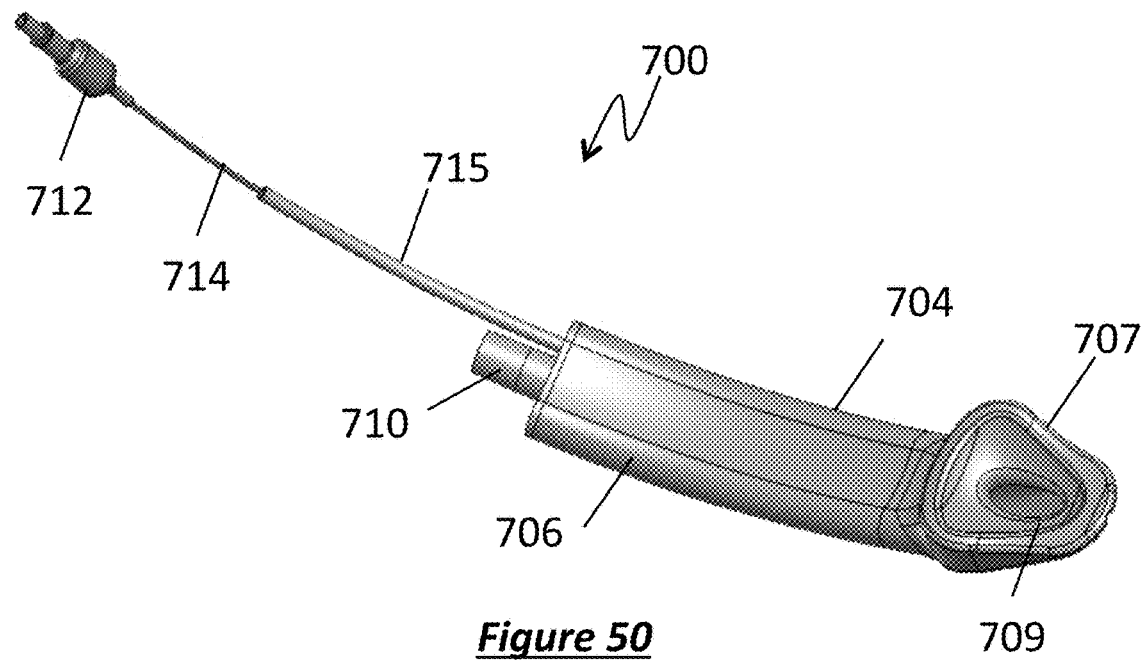
FIG. 50 is a perspective view of an intubation device having a translatable ETT component (not shown) within a LMA component according to an aspect of the invention.
Figure 51:
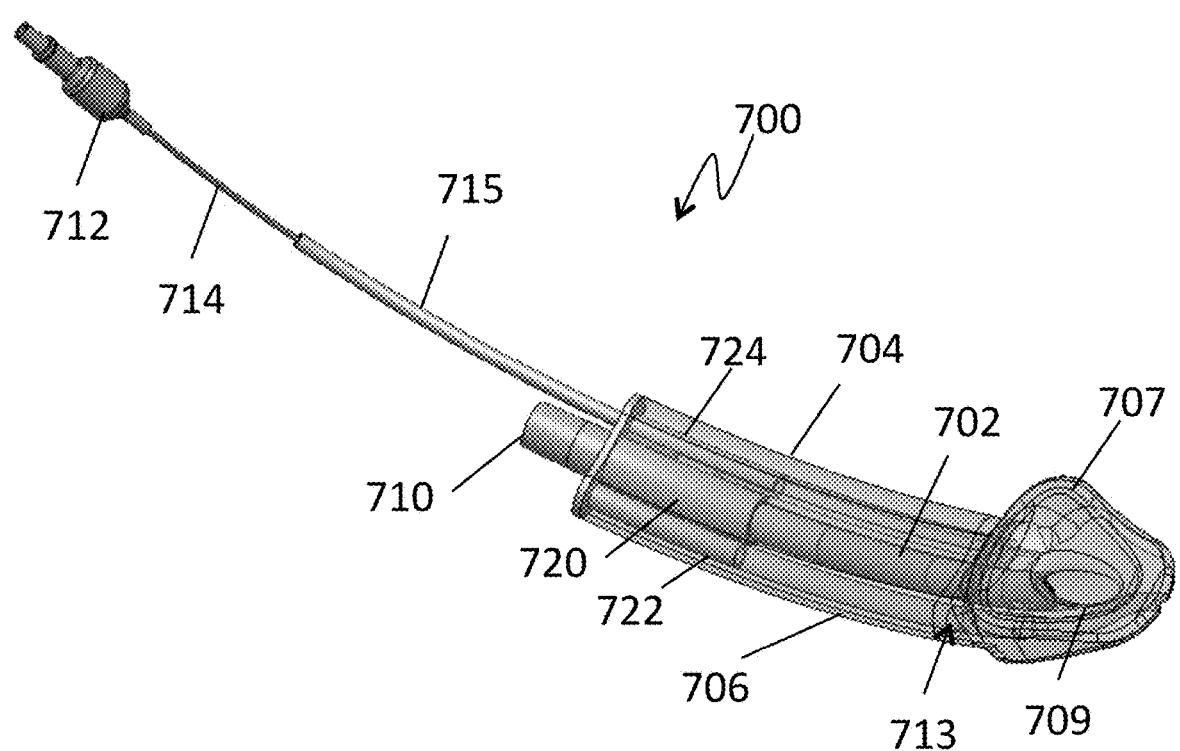
FIG. 51 is a perspective view of the intubation device shown in FIG. 50 with the LMA component shown in phantom to facilitate illustration of the translatable ETT component.
Figure 52:
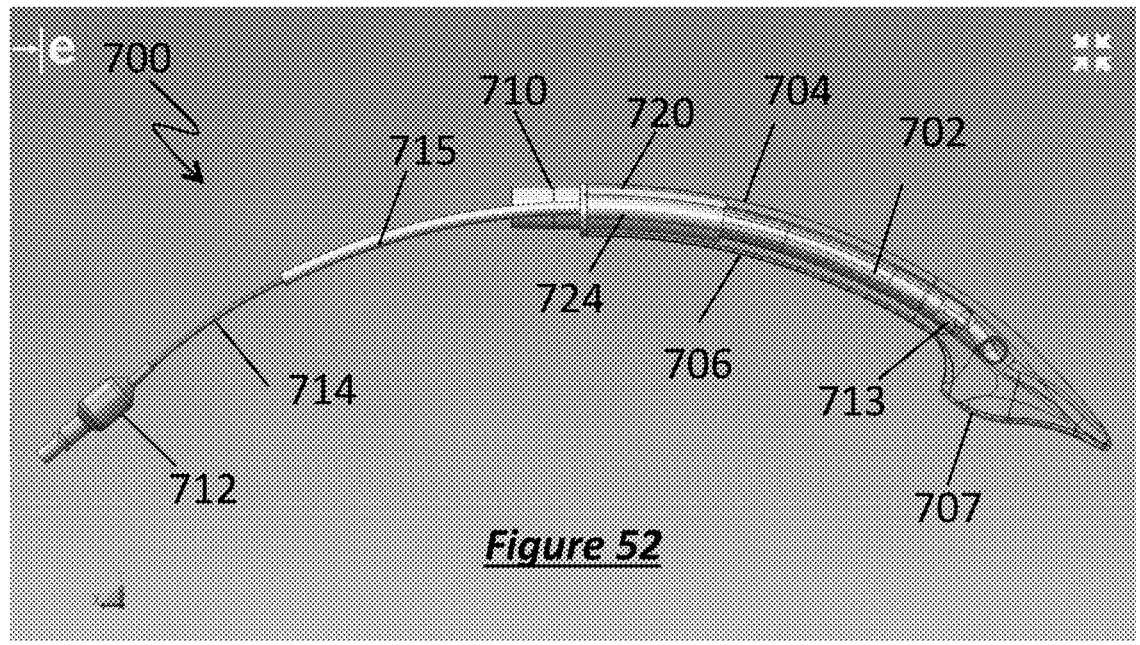
FIG. 52 is a side view of the intubation device shown in FIG. 51 with the LMA component shown in phantom to facilitate illustration of the translatable ETT component.
Figure 53:
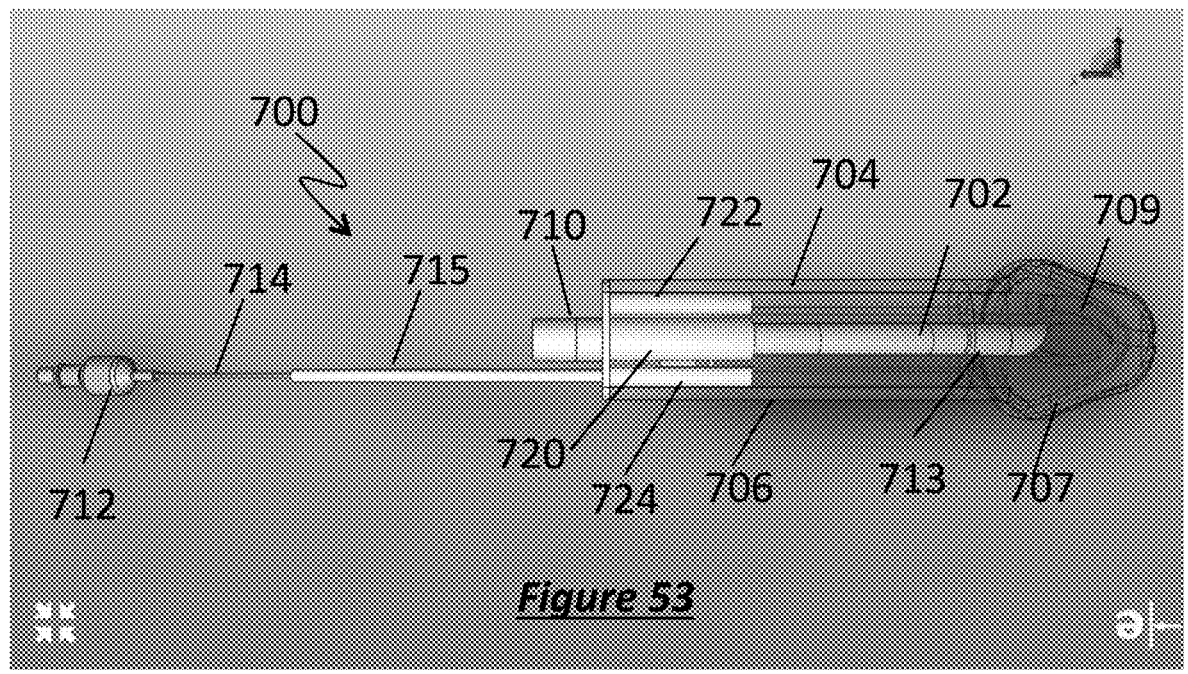
FIG. 53 is a top view of the intubation device shown in FIG. 52 with the LMA component shown in phantom to facilitate illustration of the translatable ETT component.

FIG. 50 is a perspective view of intubation device 700 having a translatable endotracheal tube (ETT) component (not shown) within a laryngeal mask airway (LMA) component 704 according to an aspect of the invention. FIG. 51 is a perspective view of intubation device 700 shown in FIG. 50 with the LMA component 704 shown in phantom to facilitate illustration of the translatable ETT component 702. FIG. 52 is a side view of intubation device 700 shown in FIG. 51 with the LMA component 704 shown in phantom to facilitate illustration of the translatable ETT component 702. FIG. 53 is a top view of intubation device 700 shown in FIG. 52 with the LMA component 704 shown in phantom to facilitate illustration of the translatable ETT component 702.

Similar to other aspects of the invention disclosed herein, intubation device 700 includes a translatable ETT component 702, an LMA component 704 having a tube portion 706 and a mask portion 707 having a mask portion opening 709, and a connector 710 adapted to engage the ETT component 702, as disclosed herein. As shown, intubation device 700 also includes a balloon cuff inflation balloon 712 operatively connected, for example, in fluid communication with, one or more inflation cuffs 713 and inflation balloon 712 is adapted to inflate inflation cuff 713 or a portion of inflation cuff 713 via one or more tubes, conduits, or passages 714. Consistent with the aspects of the invention disclosed herein, the one or more inflatable balloon cuffs 713 are positioned on ETT component 702 and provide a means for manipulating the positioning of the distal end of ETT component 702 and/or to at least partially seal a cavity into which ETT component 702 is located.

As shown in FIGS. 50 through 53, tube or conduit 714 may engage LMA component 704 via a conduit or sleeve 715, for example, a flexible sleeve. As also shown in FIGS. 51 through 53, connector 710 adapted to engage the ETT component 702 may include a central conduit or passage 720 adapted to communicate with an external source of fluid (not shown), for example, treatment fluid, such as, oxygen-containing gas, and one or more lateral conduits or passages 722 and 724 adapted to receive sleeve tube 714 or other conduits, tubes, and/or instruments introduced to intubation device 700. Further details of connector 710 are provided below with respect to FIGS. 54 through 58.

According to one aspect of the invention, conduit or sleeve 715 may be operatively connected to ETT component 702, for example, attached to ETT component 702, wherein conduit or sleeve 715 may provide a means for manipulating ETT component 702, for example, translating and/or rotating ETT component 702, in a fashion substantially identical to the function of the manipulation rods or bars disclosed herein. In one aspect, the insertion and/or extraction of sleeve 715 may axially translate ETT component 702 within LMA component 706; in another aspect, the arcuate movement of sleeve 715, for example, in an arcuate slot (not shown) in connector 710, may rotate the ETT component 702 within LMA component 706.

Figure 54:
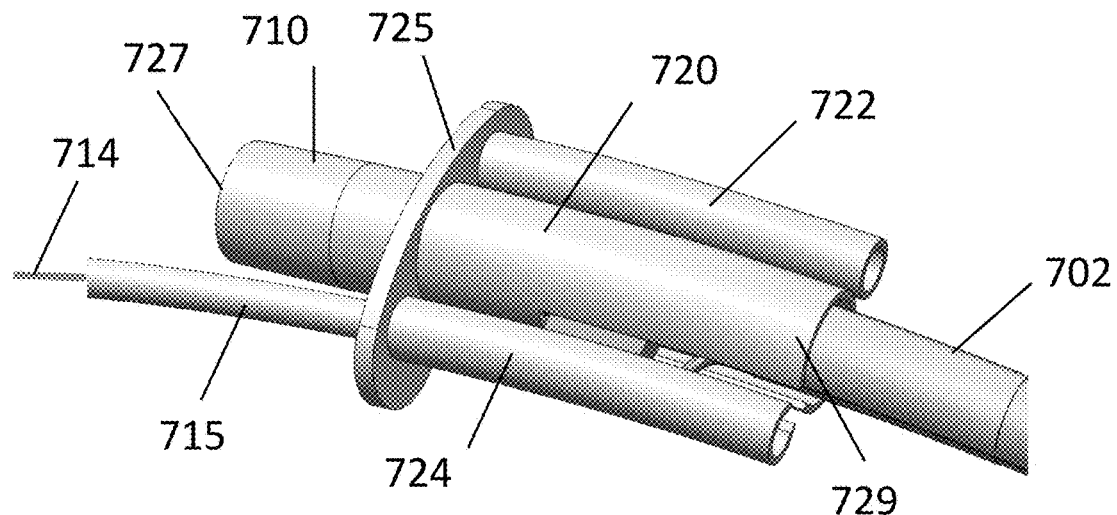
FIG. 54 is a perspective view of portions of the connector and related components of the intubation device shown in FIGS. 50 through 53 to illustrate the relationship of the components.

FIG. 54 is a perspective view of portions of the connector 710 and related components of intubation device 700 shown in FIGS. 50 through 53 to illustrate the relationship of these components. As shown in FIG. 54, connector 710 may include a central conduit or passage 720, one or more lateral conduits or passages 722 and 724, and a plate or flange 725. Central conduit 720 may include a first end 727 adapted to communicate with an external source of fluid (not shown) and a second end 729 adapted to receive ETT component 702. As discussed herein, second end 729 may include some form of sealing device (not shown) adapted to minimize or prevent leakage between second end 729 and ETT component 702.

Figure 55:
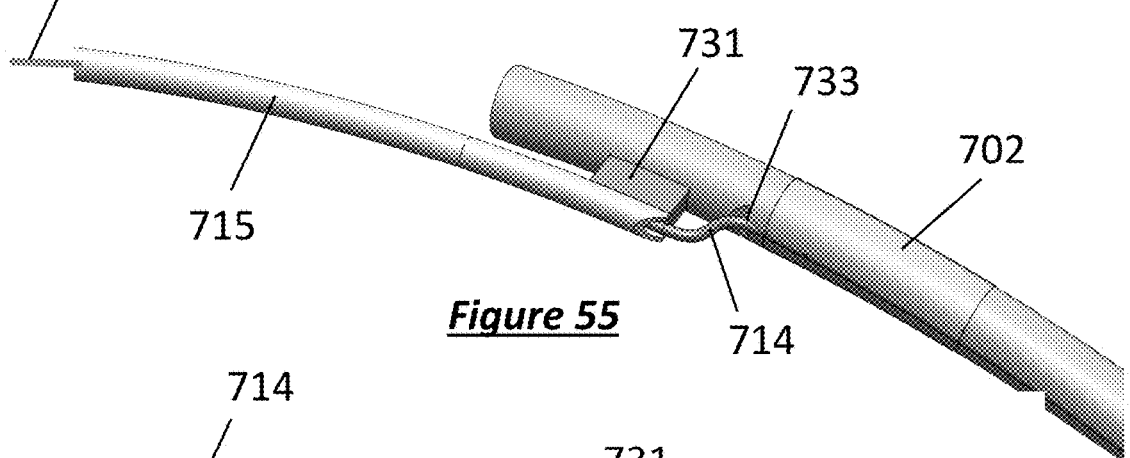
FIG. 55 is a perspective view of portions of the ETT component, an inflation balloon conduit, and manipulation rod sleeve, with the connector remove, to illustrate the relationship of these components.

As also shown in FIG. 54, lateral conduits 724 may be adapted to receive inflation balloon conduit 714 and/or sleeve 715. FIG. 55 is a perspective view of portions of ETT component 702, inflation balloon conduit 714, and sleeve 715, similar to FIG. 54 but with connector 710 removed, to facilitate the illustration of the relationship of these components. As shown in FIG. 55, sleeve 715 containing conduit 714 may pass through lateral conduit 724 (not whom in FIG. 55) and engage ETT conduit 702 via one or more projections, bars, tabs, brackets, clamps, or plates 731, for example, in a fashion as disclosed herein.

Figure 56:
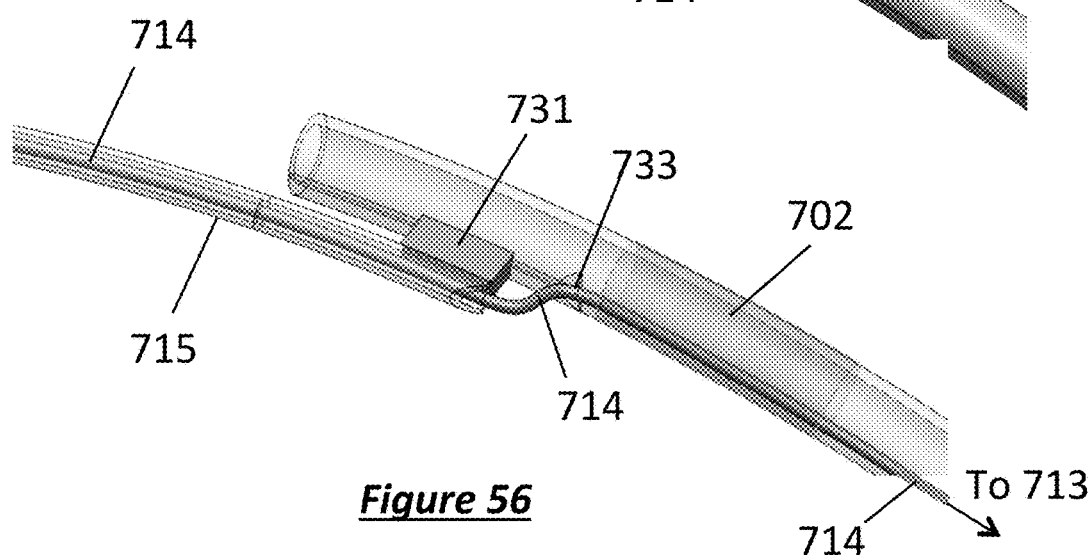
FIG. 56 is a perspective view of portions of the ETT component, the inflation balloon conduit, and the manipulation rod sleeve, with connector removed, similar to FIG. 55, but with the sleeve and the ETT component shown in phantom to illustrate aspects of the invention.

FIG. 56 is a perspective view of portions of the ETT component 702, inflation balloon conduit 714, and sleeve 715, with connector 710 removed, similar to FIG. 55, but with sleeve 715 and ETT component 702 shown in phantom to facilitate the illustration of aspects of the invention. As shown most clearly in FIGS. 55 and 56, inflation balloon conduit 714 may pass through sleeve 715 and mount to or be inserted into ETT component 702 and then pass along ETT component 702 to inflatable balloon cuff 713 (see FIGS. 50-53). In one aspect, conduit 714 may pass through an opening or hole 733 in ETT component 702 prior to extending to balloon cuff 713.

Figure 57:
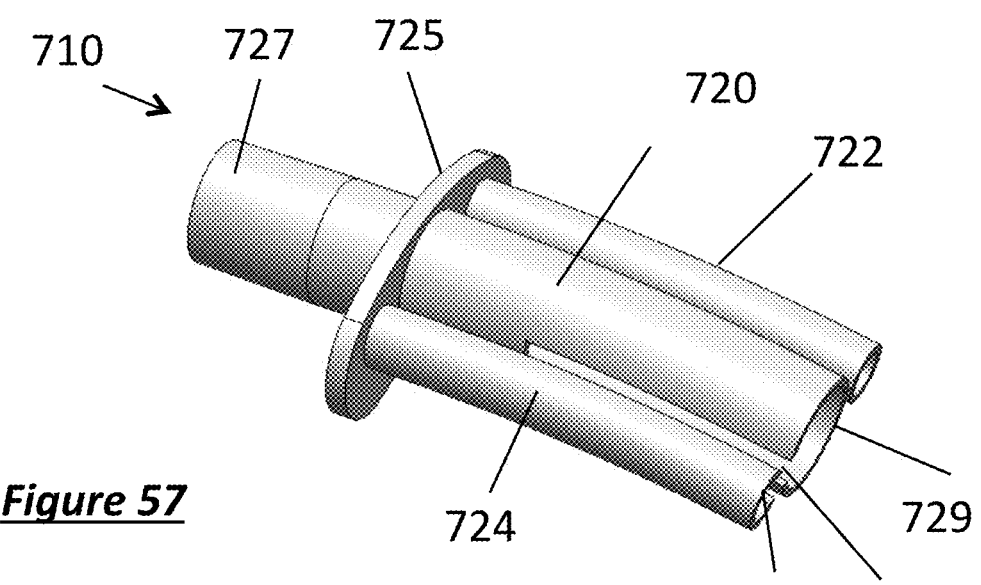
FIG. 57 is a front perspective view of the connector shown in FIG. 54, according to one aspect of the invention.
Figure 58:
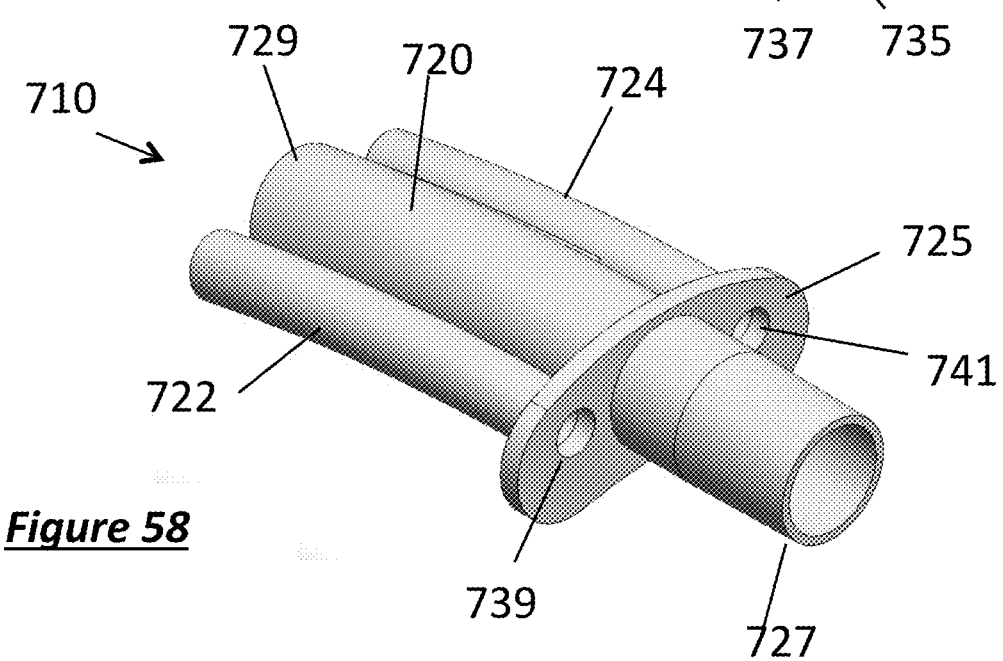
FIG. 58 is a rear perspective view of the connector shown in FIG. 57.

FIG. 57 is a front perspective view of connector 710 shown in FIG. 54, according to one aspect of the invention. FIG. 58 is a rear perspective view of connector 710 shown in FIG. 57. As shown in FIGS. 57 and 58, connector 710 includes a central conduit or passage 720, one or more lateral conduits or passages 722 and 724, and a plate or flange 725. Central conduit 720 includes a first end 727 adapted to communicate with an external source of fluid (not shown) and a second end 729 adapted to receive ETT component 702. Central conduit 720 may also include an opening or slot 735 sized and positioned to receive tab or plate 731 and conduit 714, as shown in FIG. 54. Lateral conduit 724 may also include an opening or slot 737, opposite opening or slot 737, sized and positioned to receive tab or plate 731 and conduit 714, as disclosed herein.

As shown in FIG. 58, flange or plate 725 may include one or more openings or holes 739 and 741 according to one aspect of the invention. Openings or holes 739 and 741 may be used to introduce conduits, tubes, instruments, and/or structures to connector 710 and intubation device 700. For example, as shown in FIG. 54, opening 741 may provide a means for introducing conduit 714 and/or sleeve 715 to connector 710, though opening 739 may be used in a similar fashion. In addition, openings 739 and/or 741 may be used to access intubation device 700 with other conduits or instruments, for example, for cuff inflation conduits, pressure indicator conduits, image capturing cables, and/or other sensor related conduits and/or cables.

The use of any one of the intubation devices disclosed herein may be practiced with or without the use of a guidance device, that is, a device used to assist the user in guiding the insertion and placement of the intubation devices disclosed herein. According to aspects of the invention, any conventional guidance device may be used, including a thin surgical instrument, or "bougie," as known in the art, that is, a "hard bougie" or a "soft bougie"; a bronchoscope, for example, a fiber optic bronchoscope; or any elongated rod, tube, or structure that can be used to assist the user in guiding the insertion and placement of the intubation devices disclosed herein. According to one aspect of the invention, the guidance device may be placed within the airway of the patient, and, while in place, any one of the intubation devices disclosed herein may be inserted into the airway while threading the guidance device through, for example, the endotracheal tube (ETT) component of an intubation device disclosed herein. Guidance devices that may be used when practicing aspects of the invention may include an Eschmann-style tracheal tube introducer or bougie provided by various manufactures, such as, Teleflex Inc. Insertion of aspects of the invention into an airway may be facilitated by lubricating the intubation device prior to insertion.

Though many different aspects of the present invention have been presented disclosed individually or in combination herein for the sake of facilitating disclosure, it is envisioned that any one or more of the aspects or features disclosed herein may be combined with any one or more other aspects of features disclosed herein.

The intubation devices and their subcomponents disclosed herein may be fabricated from any conventional material, for example, any conventional plastic material, elastomeric material, and even wood or metal. In one aspect, the LMA components and ETT components disclosed herein may be fabricated from any one or more the elastomeric materials disclosed herein or any plastic material. For example, the LMA components and ETT components disclosed herein may be fabricated from, for example, a polyamide (PA), for example, nylon; a polyethylene (PE), both high-density polyethylene (HDPE) and low-density polyethylene (LDPE); a polyethylene terephthalate (PET); a polypropylene (PP); a polyester (PE); a polytetrafluoroethylene (PTFE); a polystyrene (PS); an acrylonitrile butadiene styrene (ABS); a polycarbonate (PC); or a polyvinylchloride (PVC); among other plastics.

The intubation devices disclosed herein may also be provided in a broad range of sizes and dimensions, for example, depending upon the size or age of the patient being treated. Aspects of the invention may be adapted for use with adults, children, infants, and neonates. In one aspect, embodiments of the invention may be used for veterinary treatment, for example, with animals. For example, the intubation devices may have an overall length ranging from about 3 inches to about 2 feet, but may typically range in length from about 6 inches to about 12 inches, for example, about 10 inches in length. Similarly, the intubation devices disclosed herein may have an overall width ranging from about 1 inch to about 1 foot, but may typically range in width from about 2 inches to about 3 inches, for example, about 2½ inches in width.

In support of the development and optimization of the present invention, the effectiveness and ease of use of aspects of the invention were evaluated using medical training mannequins. Specifically, the ease of use and effectiveness of aspects of the present invention were investigated and evaluated using a Laerdal airway management training mannequin (model no. 25000033) and a TruCorp intubation-training mannequin (model AirSim Combo Bronchi X 1021550).

Aspects of the invention were evaluated with and without the use of guidance devices, that is, with and without the uses of a "bougie," as disclosed herein. In one set of evaluations a bronchoscope, for example, a fiber optic bronchoscope, was used as a guidance device.

The specific testing investigated whether aspects of the invention could effectively be inserted and positioned within the airway of the patient and whether the ETT component could be advanced in the airway using the manipulation rods mounted to the ETT component as disclosed herein. The positioning of aspects of the invention was evaluating using a fiber-optic bronchoscope inserted into the intubation device.

The testing revealed that aspects of the present invention could be effectively inserted and positioned within the airways of the mannequins with and without guidance devices, for example, with or without a bougie or with a bronchoscope. In addition, once placed in the airway of the mannequins the ETT component could be effectively advanced, for example, into the trachea, using the manipulation rods disclosed herein. Also, this testing revealed that the insertion of the ETT component into the airway may be improved by 1) removing the bevel on the distal end of the ETT component tube and/or 2) selectively locating the direction of the bevel, for example, to direct the face of the bevel toward the anterior direction. Based upon the insights and success of this preliminary testing, further testing and evaluation are planned.

Accordingly, in one aspect of the invention, any one of the distal ends of the ETT component tubes disclosed herein may be substantially non-beveled, for example, having an exposed cross-section substantially perpendicular to the axis of the tube.

In another aspect, any one of the distal ends of the ETT component tubes disclosed herein may have a bevel, directed in a predetermined direction, for example, having a bevel directed in an anterior direction of the patient. The bevel may have a bevel angle ranging from 30 degrees to 60 degrees, for example, a 45 degree bevel.

Though various aspects and embodiments of the invention are disclosed herein that can be used or adapted for intubation during surgery, it is envisioned that aspects of the invention may be adapted for any application where patient or victim intubation is advantageous, that includes in the emergency room (ER), in the operating room (OR), or by first responders, paramedics, and emergency medical technicians (EMTs) at accidents or other calamities. It is envisioned that aspects of the invention may be particularly advantageous for neurosurgery and/or brain surgery where the prevention of coughing, which may undesirably induce intra-cranial pressure (ICP) during extubation, is desired. Other applications of aspects of the invention are bronchoscopy thoracic surgery, obstetrics, cardiac catheterization, laparoscopic procedures, and plastic surgery, among other medical procedures, and training, for example, training of anesthesiologists.

As disclosed herein, aspects of the invention include intubation devices and their method of use that address many of the disadvantages of prior art devices and methods.

While various embodiments have been described above, it should be understood that these embodiments and their many aspects have been presented by way of example, and not limitation. It will be apparent to persons skilled in the relevant art that various changes in form and detail can be made therein without departing from the spirit and scope of the invention. Moreover, it is to be understood that the various embodiments of the invention, although different, are not necessarily mutually exclusive. Furthermore, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The detailed description presented herein, therefore, is not to be taken in a limiting sense, and the scope of the present invention is defined only by the appended claims, appropriately interpreted, along with the full range of equivalents to which the claims are entitled.

Although the term "at least one" may often be used in the specification, claims and drawings, the terms "a", "an", "the", "said", etc. also signify "at least one" or "the at least one" in the specification, claims and drawings.

While several aspects of the present invention have been described and depicted herein, alternative aspects may be affected by those skilled in the art to accomplish the same objectives. Accordingly, it is intended by the appended claims to cover all such alternative aspects as fall within the true spirit and scope of the invention.

The invention claimed is:

1. An intubation device comprising: a laryngeal mask airway (LMA) component comprising a mask portion having an internal opening, and an elongated tube mounted to the mask portion, the elongated tube having an internal passageway in fluid communication with the internal opening of the mask portion; a movable endotracheal tube (ETT) component comprising an elongated tube positioned and movable within the elongated tube of the LMA component; and a manipulation rod mounted for translation through a passage in the LMA component, the manipulation rod extending longitudinally substantially parallel to a longitudinal axis of the LMA component, the manipulation rod having a first end operatively mounted to the ETT component and a second end, opposite the first end, positioned outside the LMA component to allow an operator to manipulate the second end of the manipulation rod to translate the ETT component within and along the LMA component.

2. The intubation device as recited in claim 1, wherein the passage substantially parallel to the axis of the LMA component comprises a passage through a body of the LMA component.

3. The intubation device as recited in claim 1, wherein the passage comprises a slot.

4. The intubation device as recited in claim 1, wherein the manipulation rod is further adapted to allow the operator to rotate the ETT component within the LMA component.

5. The intubation device as recited in claim 1, wherein the device further comprises at least one inflatable cuff mounted to the elongated tube of the ETT component and at least one cuff inflation device operatively connected to the at least one inflatable cuff, wherein when at least partially inflated, the at least one inflatable cuff at least partially restricts fluid flow about the elongated tube of the ETT component.

6. The intubation device as recited in claim 5, wherein the at least one cuff inflation device is operatively connected to the at least one inflatable cuff via a conduit passing through the manipulation rod.

7. The intubation device as recited in claim 6, wherein the manipulation rod comprises a translatable sleeve having an internal passage through which the inflatable cuff conduit passes.

8. The intubation device as recited in claim 1, wherein the device further comprises a sealing device adapted to minimize fluid leakage about the manipulation rod.

9. The intubation device as recited in claim 8, wherein the sealing device comprises an elastomeric material.

10. The intubation device as recited in claim 1, wherein the mask portion of the LMA component further comprises a structure adapted to receive and orient the passage of the elongated tube of the ETT component.

11. The intubation device as recited in claim 10, wherein the structure adapted to receive and orient the elongated tube of the ETT component comprises one of an incline and a ramp.

12. The intubation device as recited in claim 1, wherein the LMA component further comprises a conduit operatively connected to the elongated tube of the ETT component.

13. The intubation device as recited in claim 12, wherein the device further comprises a sealing device between the conduit of the LMA component and the elongated tube of the ETT component.

14. The intubation device as recited in claim 1, wherein the LMA component further comprises a stop preventing extraction of the ETT component from the LMA component.

15. The intubation device as recited in claim 1, wherein the first end of the manipulation rod is mounted to a side of the elongated tube of the ETT component.

16. The intubation device as recited in claim 1, wherein the LMA component comprises a connector adapted to engage the ETT component.

17. The intubation device as recited in claim 16, wherein the connector adapted to engage the ETT component comprises a central passage adapted to connect to a source of fluid and the passage through which the manipulation rod translates.

18. The intubation device as recited in claim 17, wherein the central passage comprises a first end adapted to communicate with the source of fluid and a second end adapted to receive the ETT component.

19. The intubation device as recited in claim 18, wherein the device further comprises a sealing device between second end of the central passage of and the ETT component.

20. The intubation device as recited in claim 1, wherein the ETT component is prevented from being removed from the LMA component.

21. The intubation device as recited in claim 20, wherein the ETT component is prevented from being removed from the LMA component by an extraction stop in the LMA component.

22. The intubation device as recited in claim 21, wherein the extraction stop comprises an obstruction within the internal passageway of the LMA component.

23. An intubation device comprising:
a laryngeal mask airway (LMA) component comprising a mask portion having an internal opening, a slot, and an elongated tube mounted to the mask portion, the elongated tube having an internal passageway in fluid communication with the internal opening of the mask portion;
a movable endotracheal tube (ETT) component comprising an elongated tube positioned and movable within the elongated tube of the laryngeal mask airway component; and
a manipulation rod passing through the slot of the LMA component and operatively mounted in the ETT component, the manipulation rod adapted to allow an operator to rotate the ETT component within the LMA component.

24. The intubation device as recited in claim 23, wherein the manipulation rod is further adapted to allow the operator to rotate translate the ETT component within the LMA component.

25. The intubation device as recited in claim 23, wherein the device further comprises at least one inflatable cuff mounted to the elongated tube of the ETT component and at least one cuff inflation device operatively connected to the at least one inflatable cuff, wherein when at least partially inflated, the at least one inflatable cuff at least partially restricts fluid flow about the elongated tube of the ETT component.

26. The intubation device as recited in claim 25, wherein the at least one cuff inflation device is operatively connected to the at least one inflatable cuff via a conduit passing through the manipulation rod.

27. The intubation device as recited in claim 26, wherein the manipulation rod comprises a translatable sleeve having an internal passage through which the inflatable cuff conduit passes.

28. The intubation device as recited in claim 23, wherein the device further comprises a sealing device adapted to minimize fluid leakage about the manipulation rod.

29. The intubation device as recited in claim 28, wherein the sealing device comprises an elastomeric material.

30. The intubation device as recited in claim 23, wherein the mask portion of the LMA component further comprises a distal end having an orifice.

31. The intubation device as recited in claim 23, wherein the mask portion of the LMA component further comprises a structure adapted to receive and orient the passage of the elongated tube of the ETT component.

32. The intubation device as recited in claim 31, wherein the structure adapted to receive and orient the elongated tube of the ETT component comprises one of an incline and a ramp.

33. The intubation device as recited in claim 23, wherein the LMA component further comprises a conduit operatively connected to the elongated tube of the ETT component.

34. The intubation device as recited in claim 33, wherein the device further comprises a sealing device between the conduit of the LMA component and the elongated tube of the ETT component.

35. The intubation device as recited in claim 23, wherein the LMA component further comprises a stop preventing extraction of the ETT component from the LMA component.

\* \* \* \* \*

UNITED STATES PATENT AND TRADEMARK OFFICE
CERTIFICATE OF CORRECTION

PATENT NO. : 10,596,339 B2
APPLICATION NO. : 16/255983
DATED : March 24, 2020
INVENTOR(S) : Musuku et al.

Page 1 of 1

It is certified that error appears in the above-identified patent and that said Letters Patent is hereby corrected as shown below:

In the Claims

Column 38, Claim 24, Line 58: Delete "rotate"

Signed and Sealed this
Second Day of June, 2020

Andrei Iancu
*Director of the United States Patent and Trademark Office*